(12) United States Patent
Cheng et al.

(10) Patent No.: US 7,553,825 B2
(45) Date of Patent: Jun. 30, 2009

(54) ANTI-PROLIFERATIVE COMPOUNDS, COMPOSITIONS, AND METHODS OF USE THEREOF

(75) Inventors: Xiaoqin Cheng, Broomfield, CO (US);
Gary P. Cook, Westford, MA (US);
Manoj C. Desai, Pleasant Hill, CA (US);
Edward Doerffler, San Mateo, CA (US); Gong-Xin He, Fremont, CA (US);
Choung U. Kim, San Carlos, CA (US);
William A. Lee, Los Altos, CA (US);
John C. Rohloff, Boulder, CO (US);
Jianying Wang, Foster City, CA (US);
Zheng-Yu Yang, Foster City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 321 days.

(21) Appl. No.: 11/026,303

(22) Filed: Dec. 29, 2004

(65) Prior Publication Data

US 2005/0222090 A1    Oct. 6, 2005

Related U.S. Application Data

(60) Provisional application No. 60/606,595, filed on Sep. 1, 2004, provisional application No. 60/590,987, filed on Jul. 26, 2004, provisional application No. 60/533,745, filed on Dec. 30, 2003.

(51) Int. Cl.
C07F 9/6561 (2006.01)
A61K 31/675 (2006.01)
A61P 31/20 (2006.01)

(52) U.S. Cl. .................. 514/81; 544/244
(58) Field of Classification Search .............. 514/81; 544/244
See application file for complete search history.

(56) References Cited

U.S. PATENT DOCUMENTS

| | | | |
|---|---|---|---|
| 4,816,570 A | 3/1989 | Farquhar | |
| 4,968,788 A | 11/1990 | Farquhar | |
| 5,663,159 A | 9/1997 | Starrett, Jr. et al. | |
| 5,792,756 A | 8/1998 | Starrett, Jr. et al. | |
| 5,977,061 A * | 11/1999 | Holy et al. | 514/7 |
| 6,312,662 B1 | 11/2001 | Erion et al. | |
| 2002/0119443 A1* | 8/2002 | Becker et al. | 435/5 |
| 2003/0072814 A1* | 4/2003 | Maibach et al. | 424/722 |
| 2003/0187261 A1* | 10/2003 | Havlicek et al. | 544/276 |
| 2003/0219727 A1 | 11/2003 | Becker et al. | |
| 2005/0222090 A1 | 10/2005 | Cheng et al. | |
| 2006/0046981 A1 | 3/2006 | Shibata | |

FOREIGN PATENT DOCUMENTS

| | | |
|---|---|---|
| WO | WO 91/19721 | 12/1991 |
| WO | WO 01/49688 | 7/2001 |
| WO | WO 2005/066189 | 7/2005 |

OTHER PUBLICATIONS

Holy, Collection of Czechoslovak Chemical Communications (2001), 66(10), 1545-1592.*

(Continued)

Primary Examiner—Mark L Berch
(74) Attorney, Agent, or Firm—Cynthia H. Zhang

(57) ABSTRACT

Compounds and compositions of Formula I are described, useful as anti-proliferative agents, and in particular anti-HPV,

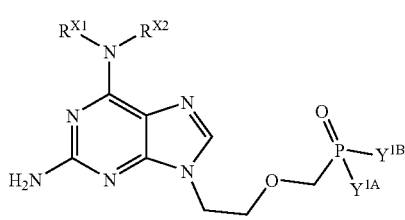

wherein:
$Y^{1A}$ and $Y^{1B}$ are independently $Y^1$;
$R^{X1}$ and $R^{X2}$ are independently $R^X$;
$Y^1$ is =O, —O($R^X$), =S, —N($R^X$), —N(O)($R^X$), —N(O$R^X$), —N(O)(O$R^X$), or —N(N($R^X$) ($R^X$));
$R^X$ is independently $R^1$, $R^2$, $R^4$, $W^3$, or a protecting group;
$R^1$ is independently —H or alkyl of 1 to 18 carbon atoms;
$R^2$ is independently $R^3$ or $R^4$ wherein each $R^4$ is independently substituted with 0 to 3 $R^3$ groups or taken together at a carbon atom, two $R^2$ groups form a ring of 3 to 8 carbons and the ring may be substituted with 0 to 3 $R^3$ groups;
$R^3$ is $R^{3a}$, $R^{3b}$, $R^{3c}$ or $R^{3d}$, provided that when $R^3$ is bound to a heteroatom, then $R^3$ is $R^{3c}$ or $R^{3d}$;
$R^{3a}$ is —H, —F, —Cl, —Br, —I, —CF$_3$, —CN, N$_3$, —NO$_2$, or —OR$^4$;
$R^{3b}$ is =O, —O($R^4$), =S, —N($R^4$), —N(O)($R^4$), —N(OR$^4$), —N(O)(OR$^4$), or —N(N($R^4$) ($R^4$));
$R^{3c}$ is —$R^4$, —N($R^4$)($R^4$), —S$R^4$, —S(O)$R^4$, —S(O)$_2R^4$, —S(O)(OR$^4$), —S(O)$_2$(OR$^4$), —OC(R$^{3b}$)$R^4$, —OC(R$^{3b}$)OR$^4$, —OC(R$^{3b}$)(N($R^4$)($R^4$)), —SC(R$^{3b}$)$R^4$, —SC(R$^{3b}$)OR$^4$, SC(R$^{3b}$)(N($R^4$)($R^4$)), —N($R^4$)C(R$^{3b}$)$R^4$, —N($R^4$)C(R$^{3b}$)OR$^4$, N($R^4$)C(R$^{3b}$)(N($R^4$)($R^4$)), $W^3$ or —$R^5W^3$;
$R^{3d}$ is —C(R$^{3b}$)$R^4$, —C(R$^{3b}$)OR$^4$, —C(R$^{3b}$)$W^3$, —C(R$^{3b}$)OW$^3$ or —C(R$^{3b}$)(N($R^4$)($R^4$));
$R^4$ is —H, or an alkyl of 1 to 18 carbon atoms, alkenyl of 2 to 18 carbon atoms, or alkynyl of 2 to 18 carbon atoms;
$R^5$ is alkylene of 1 to 18 carbon atoms, alkenylene of 2 to 18 carbon atoms, or alkynylene of 2 to 18 carbon atoms;
$W^3$ is $W^4$ or $W^5$;
$W^4$ is $R^6$, —C(R$^{3b}$)$R^6$, —C(R$^{3b}$)$W^5$, —SO$_{M2}R^6$, or —SO$_{M2}W^5$, wherein $R^6$ is $R^4$ wherein each $R^4$ is substituted with 0 to 3 $R^3$ groups;
$W^5$ is carbocycle or heterocycle wherein $W^5$ is independently substituted with 0 to 3 $R^2$ groups; and
M2 is 0, 1 or 2;
and pharmaceutically acceptable salts thereof.

9 Claims, No Drawings

OTHER PUBLICATIONS

Zidek, et al., European Journal of Pharmacology (2003), 475(1-3), 149-159.*

Benzaria et al. "Synthesis, In Vitro Antiviral Evaluation, and Stability Studies of Bis(S-acyl-2-thioethyl) Ester . . . " 39:4958-4965; J Med Chem., 1996.

Bundgaard et al. "Design and Application of Prodrugs."p. 113-191; Textbook of Drug Design and Development., 1991.

Christensen et al."In Vivo anti-papilomavirus Activity of Nucleoside Analogues Including Cidofovir on CRPV-induced Rabbit . . . " 48:131-142; Antiviral Resjournal., 2000.

De Lombaert et al. "N-Phosphonomethyl Dipeptides and heir Phosphonate Prodrugs, a New Generation of Neutral Endopeptidase . . . " 37:498-511; J Med Chem., 1994.

Draize et al. "Methods for the Study of Irritation and Toxicity of Substances Applied Topically to the Skin and Mucous Membranes." 82:377-390; J Pharm Pharmacol., 1944.

Farquhar et al. "Biologically Reversible Phosphate-Protective Groups."72:324-325; J Pharm Sci., 1983.

Keith et al."Evalution of Nucleoside Phosphonates and Their Analogs and Prodrugs for Inhibition of Orthopozvirus Replication." 47(7): 2193-2198; Antimicro AG & Chemo., 2003.

Khamnei et al. "Neighboring Group Catalysis in the Design of Nucleotide Prodrugs."39:4109-4115; J Med Chem., 1996.

Mitchell et al. "Bioreversible Protection for the Phospho Group: Bioactivation of the Di(4 acyloxybenzyl) and . . . " 2345;J Chem Soc Perkin Trans I., 1992.

Paquette, Leo A. "Three-Membered Rings with One Hetero Atom. "Chptr:1;Principals of Modern Heterocyclic Chemistry., 1968.

Paquette, Leo A. "The Four-Membered Heterocyles. "Chptr:3;Principals of Modern Heterocyclic Chemistry., 1968.

Paquette, Leo A. "Furan, Pyrrole, and Thiophene."Chptr:4;Principals of Modern Heterocyclic Chemistry., 1968.

Paquette, Leo A. "The Azoles."Chptr:6;Principals of Modern Heterocyclic Chemistry., 1968.

Paquette, Leo A. "The Pyridine Group."Chptr:7;Principals of Modern Heterocyclic Chemistry., 1968.

Paquette, Leo A. "The Diazines and S-Triazine."Chptr:9;Principals of Modern Heterocyclic Chemistry., 1968.

Puech et al. "Intracellular delivery of nucleoside monophosphates through a reuctase-mediated activation process." 22:155-174; Antiviral Res., 1993.

Snoeck et al."Antivaccinia Activities of Acyclic Nucleoside Phosphonate Derivatives in Epithelial Cells and Organotypic Cultures." 46(11):3356-3361;Antimicro AG & Chemo., 2002.

Stuttgart, Georg Thieme Verlag"An Overview."p. 1-20; Protecting Groups., 1994.

Stuttgart, Georg Thieme Verlag"Hydroxyl Protecting Groups."p. 21-94; Protecting Groups., 1994.

Stuttgart, Georg Thieme Verlag "Diol Protecting Groups."p. 95-117; Protecting Groups., 1994.

Stuttgart, Georg Thieme Verlag "Carboxyl Protecting Groups."p. 118-154;Protecting Groups., 1994.

Stuttgart, Georg Thieme Verlag "Carbonyl Protecting Groups."p. 155-184;Protecting Groups., 1994.

Valerianova et al. "Antitumour Activity of N6-Substituted PMEDAP Derivatives Against T-Cell Lymphoma."21(3):2057-2064;Anticancer Rsrch, Helenic Anticancer Inst., Athens., 2001.

Valerianova et al. "PMEDAP and it's N6-Substituted Derivatives: Genotoxic Effect and . . . "23(6):4933-4940;Anticancer Rsrch, Helenic Anticancer Inst., Athens.,2003.

Zidek et al. "Immunobiological Activity of N-[2-(phosphonomethoxy)alkyl] Derivatives of N6-Substituted Adenines, and 2,6-diaminopurines."475:149-159;European Journ of Pharmacol.

Compton, et al. "9-(2-Phosphonylmethoxyethyl)-$N^6$—cyclopropyl-2,6-diaminopurine (cpr-PMEDAP) as a Prodrug of 9-(2-Phosphonylmethoxyethyl)guanine (PMEG)", *Biochemical Pharmacology*, (1999) 58:709-714.

Hatse et al. "$N^6$ Cyclopropyl-PMEDAP: A Novel Derivative of 9-(2-Phosphonylmethoxyethyl)- 2,6-diaminopurine (PMEDAP) with Distinct Metabolic, Antiproliferative, and Differentiation—Inducing Properties," *Biochemicla Pharmacology*, (1999) 58:311-323.

Rose et al. "In Vivo Antitumor Activity of 9-[2-Phosphonylmethpxy)ethyl]-guanine and Related Phosphonate Nucleotide Analogues," *Journal of National Cancer Institute* (1990) 82(6):510-512.

* cited by examiner

ANTI-PROLIFERATIVE COMPOUNDS, COMPOSITIONS, AND METHODS OF USE THEREOF

This application claims the benefit of U.S. Provisional Application Nos:
60/533,745 filed Dec. 30, 2003;
60/590,987 filed Jul. 26, 2004;
60/606,595 filed Sep. 1, 2004;

BACKGROUND OF THE INVENTION

1. Field of the Invention

The present invention relates to compounds and compositions and methods of use thereof, useful for treating viral infections, in particular human papillomavirus.

2. Background

Human papillomavirus (HPV) is one of the most prevalent sexually transmitted infections in the world. There are more than 100 different types of HPV, the majority of which are harmless. However, there are about 30 types that are spread through sexual contact. Some types of HPV cause genital warts, which appear as single or multiple bumps in the genital areas of men and women including the vagina, cervix, vulva (area outside of the vagina), penis, and rectum. Although many people infected with HPV have no symptoms.

While most HPV subtypes result in benign lesions, certain subtypes can lead to more serious lesions. Anogenital infections arising from HPV-16 and HPV-18, while less common than HPV-6 and HPV-11, are most often associated with precancerous lesions in cervical and anal tissues called dysplasias. Patients with dysplasias are often asymptomatic and may only discover their lesion after screening. High-grade dysplasias, if left untreated, may transform into cancerous tissues. Low-grade lesions may spontaneously regress, while others may progress to high-grade lesions. HPV-16 and HPV-18 are most often associated with dysplasias, though several other transforming HPV subtypes are also associated with dysplasias. Recent studies indicate that up to 89% of HIV positive homosexual males may be infected with these high-risk subtypes of HPV. HIV positive patients are also more likely to be infected with multiple subtypes of HPV at the same time, which is associated with a higher risk of dysplasia progression.

Genital warts are the most common sexually transmitted disease in the world and are most prevalent in people 17-33 years of age. HPV-6 and HPV-11 are responsible for nearly 90% of all genital warts, but are rarely associated with neoplastic growths. According to the American Social Health Association, at least 20 million people in the US are currently infected with HPV, with 5.5 million new cases of sexually transmitted HPV infections occurring annually. Genital warts usually produce painless-itchy bumps located on or near the genitalia, but without treatment, may progress to larger more pronounced cauliflower-like growths. Roughly two-thirds of people who have sexual contact with a person infected with genital warts will develop warts within three months of contact. Spontaneous regression of genital warts occurs in 10-20% of genital wart cases. However, even if a lesion regresses, recurrence of genital warts is common with 50% recurrence after one year. As a result of the unsightly lesions, treatment of genital warts is common.

Evidence over the last two decades has led to a broad acceptance that HPV infection is necessary, though not sufficient, for the development of cervical cancer. The presence of HPV in cervical cancer is estimated at 99.7%. Anal cancer is thought to have a similar association between HPV infection and the development of anal dysplasia and anal cancer as is the case with cervical cancer. In one study of HIV negative patients with anal cancer, HPV infection was found in 88% of anal cancers. In the U.S. in 2003, 12,200 new cases of cervical cancer and 4,100 cervical-cancer deaths are predicted along with 4,000 new cases of anal cancer and 500 anal-cancer deaths. While the incidence of cervical cancer has decreased in the last four decades due to widespread screening, the incidence of anal cancer is increasing. The increase in anal cancer incidence may be attributed in part to HIV infection since HIV positive patients have a higher incidence of anal cancer than the general population. While anal cancer has an incidence of 0.9 cases per 100,000 in the general population, anal cancer has an incidence of 35 cases per 100,000 in the homosexual male population and 70-100 cases per 100,000 in the HIV positive homosexual male population. In fact, due to the high prevalence of anal dysplasia among HIV-infected patients and a growing trend of anal cancers, the 2003 USPHA/IDSA Guidelines for the Treatment of Opportunistic Infections in HIV Positive Patients will include treatment guidelines for patients diagnosed with anal dysplasia.

There is no known cure for HPV. There are treatments for genital warts, though they often disappear even without treatment. The method of treatment depends on factors such as the size and location of the genital warts. Among the treatments used are, Imiquimod cream, 20 percent podophyllin antimitotic solution, 0.5 percent podofilox solution, 5 percent 5-fluorouracil cream, and Trichloroacetic acid. The use of podophyllin or podofilox is not recommended for pregnant women because they are absorbed by the skin and may cause birth defects. The use of 5-fluorouracil cream is also not recommended for pregnant women. Small genital warts can be physically removed by freezing (cryosurgery), burning (electrocautery) or laser treatment. Large warts that do not responded to other treatment may have to be removed by surgery. Genital warts have been known to return following physical removal, in these instances α-interferon have been used to directly inject into these warts. However, α-interferon is expensive, and its use does not reduce the rate of return of the genital warts.

As such there exists an unmet need for effective HPV treatment. It has now been surprisingly discovered compounds that meet this need, and provide other benefits as well.

SUMMARY OF THE INVENTION

A compound of formula I,

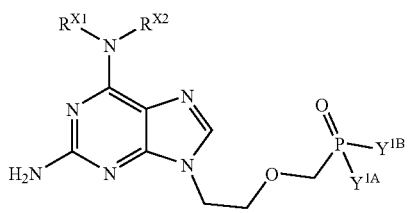

wherein:
$Y^{1A}$ and $Y^{1B}$ are independently $Y^1$;
$R^{X1}$ and $R^{X2}$ are independently $R^X$;
$Y^1$ is =O, —O($R^X$), =S, —N($R^X$), —N(O)($R^X$), —N(O$R^X$), —N(O)(O$R^X$), or —N(N($R^X$) ($R^X$));
$R^X$ is independently $R^1$, $R^2$, $R^4$, $W^3$, or a protecting group;
$R^1$ is independently —H or alkyl of 1 to 18 carbon atoms;

R$^2$ is independently R$^3$ or R$^4$ wherein each R$^4$ is independently substituted with 0 to 3 R$^3$ groups or taken together at a carbon atom, two R$^2$ groups form a ring of 3 to 8 carbons and the ring may be substituted with 0 to 3 R$^3$ groups;

R$^3$ is R$^{3a}$, R$^{3b}$, R$^{3c}$ or R$^{3d}$, provided that when R$^3$ is bound to a heteroatom, then R$^3$ is R$^{3c}$ or R$^{3d}$;

R$^{3a}$ is —H, —F, —Cl, —Br, —I, —CF$_3$, —CN, N$_3$, —NO$_2$, or —OR$^4$;

R$^{3b}$ is =O, —O(R$^4$), =S, —N(R$^4$), —N(O)(R$^4$), —N(OR$^4$), —N(O)(OR$^4$), or —N(N(R$^4$) (R$^4$));

R$^{3c}$ is —R$^4$, —N(R$^4$)(R$^4$), —SR$^4$, —S(O)R$^4$, —S(O)$_2$R$^4$, —S(O)(OR$^4$), —S(O)$_2$(OR$^4$), —OC(R$^{3b}$)R$^4$, —OC(R$^{3b}$)OR$^4$, —OC(R$^{3b}$)(N(R$^4$)(R$^4$)), —SC(R$^{3b}$)R$^4$, —SC(R$^{3b}$)OR$^4$, —SC(R$^{3b}$)(N(R$^4$)(R$^4$)), —N(R$^4$)C(R$^{3b}$)R$^4$, —N(R$^4$)C(R$^{3b}$)OR$^4$, —N(R$^4$)C(R$^{3b}$)(N(R$^4$)(R$^4$)), W$^3$ or —R$^5$W$^3$;

R$^{3d}$ is —C(R$^{3b}$)R$^4$, —C(R$^{3b}$)OR$^4$, —C(R$^{3b}$)W$^3$, —C(R$^{3b}$)OW$^3$ or —C(R$^{3b}$)(N(R$^4$)(R$^4$);

R$^4$ is —H, or an alkyl of 1 to 18 carbon atoms, alkenyl of 2 to 18 carbon atoms, or alkynyl of 2 to 18 carbon atoms;

R$^5$ is alkylene of 1 to 18 carbon atoms, alkenylene of 2 to 18 carbon atoms, or alkynylene of 2 to 18 carbon atoms;

W$^3$ is W$^4$ or W$^5$;

W$^4$ is R$^6$, —C(R$^{3b}$)R$^6$, —C(R$^{3b}$)W$^5$, —SO$_{M2}$R$^6$, or —SO$_{M2}$W$^5$, wherein R$^6$ is R$^4$ wherein each R$^4$ is substituted with 0 to 3 R$^3$ groups;

W$^5$ is carbocycle or heterocycle wherein W$^5$ is independently substituted with 0 to 3 R$^2$ groups; and M2 is 0, 1 or 2;

and pharmaceutically acceptable salts thereof.

DETAILED DESCRIPTION OF THE INVENTION

The present invention provides a compound of the formula,

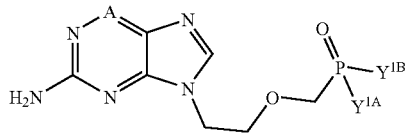

wherein:

A is

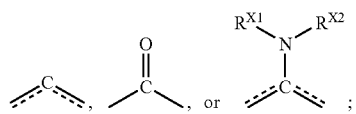

Y$^{1A}$ and Y$^{1B}$ are independently Y$^1$;

R$^{X1}$ and R$^{X2}$ are independently R$^X$;

Y$^1$ is =O, —O(R$^X$), =S, —N(R$^X$), —N(O)(R$^X$), —N(OR$^X$), —N(O)(OR$^X$), or —N(N(R$^X$)(R$^X$));

R$^X$ is independently R$^1$, R$^2$, R$^4$, W$^3$, or a protecting group;

R$^1$ is independently —H or alkyl of 1 to 18 carbon atoms;

R$^2$ is independently R$^3$ or R$^4$ wherein each R$^4$ is independently substituted with 0 to 3 R$^3$ groups or taken together at a carbon atom, two R$^2$ groups form a ring of 3 to 8 carbons and the ring may be substituted with 0 to 3 R$^3$ groups;

R$^3$ is R$^{3a}$, R$^{3b}$, R$^{3c}$ or R$^{3d}$, provided that when R$^3$ is bound to a heteroatom, then R$^3$ is R$^{3c}$ or R$^{3d}$;

R$^{3a}$ is —H, —F, —Cl, —Br, —I, —CF$_3$, —CN, N$_3$, —NO$_2$, or —OR$^4$;

R$^{3b}$ is =O, —O(R$^4$), =S, —N(R$^4$), —N(O)(R$^4$), —N(OR$^4$), —N(O)(OR$^4$), or —N(N(R$^4$)(R$^4$));

R$^{3c}$ is —R$^4$, —N(R$^4$)(R$^4$), —SR$^4$, —S(O)R$^4$, —S(O)$_2$R$^4$, —S(O)(OR$^4$), —S(O)$_2$(OR$^4$), —OC(R$^{3b}$)R$^4$, —OC(R$^{3b}$)OR$^4$, —OC(R$^{3b}$)(N(R$^4$)(R$^4$)), —SC(R$^{3b}$)R$^4$, —SC(R$^{3b}$)OR$^4$, —SC(R$^{3b}$)(N(R$^4$)(R$^4$)), —N(R$^4$)C(R$^{3b}$)R$^4$, —N(R$^4$)C(R$^{3b}$)OR$^4$, —N(R$^4$)C(R$^{3b}$)(N(R$^4$)(R$^4$)), W$^3$ or —R$^5$W$^3$;

R$^{3d}$ is —C(R$^{3b}$)R$^4$, —C(R$^{3b}$)OR$^4$, —C(R$^{3b}$)W$^3$, —C(R$^{3b}$)OW$^3$ or —C(R$^{3b}$)(N(R$^4$)(R$^4$));

R$^4$ is —H, or an alkyl of 1 to 18 carbon atoms, alkenyl of 2 to 18 carbon atoms, or alkynyl of 2 to 18 carbon atoms;

R$^5$ is alkylene of 1 to 18 carbon atoms, alkenylene of 2 to 18 carbon atoms, or alkynylene of 2 to 18 carbon atoms;

W$^3$ is W$^4$ or W$^5$;

W$^4$ is R$^6$, —C(R$^{3b}$)R$^6$, —C(R$^{3b}$)W$^5$, —SO$_{M2}$R$^6$, or —SO$_{M2}$W$^5$, wherein R$^6$ is R$^4$ wherein each R$^4$ is substituted with 0 to 3 R$^3$ groups;

W$^5$ is carbocycle or heterocycle wherein W$^5$ is independently substituted with 0 to 3 R$^2$ groups; and M2 is 0, 1 or 2;

and pharmaceutically acceptable salts thereof.

A compound of formula I,

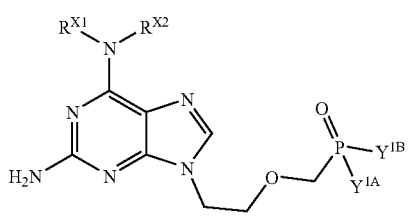

wherein;

Y$^{1A}$ and Y$^{1B}$ are independently Y$^1$;

R$^{X1}$ and R$^{X2}$ are independently R$^X$;

Y$^1$ is —NH(R$^X$);

R$^X$ is independently R$^1$, R$^2$, R$^4$, W$^3$, or a protecting group;

R$^1$ is independently —H or alkyl of 1 to 18 carbon atoms;

R$^2$ is independently R$^3$ or R$^4$ wherein each R$^4$ is independently substituted with 0 to 3 R$^3$ groups or taken together at a carbon atom, two R$^2$ groups form a ring of 3 to 8 carbons and the ring may be substituted with 0 to 3 R$^3$ groups;

R$^3$ is R$^{3a}$, R$^{3b}$, R$^{3c}$ or R$^{3d}$, provided that when R$^3$ is bound to a heteroatom, then R$^3$ is R$^3$ or R$^{3d}$;

R$^{3a}$ is —H, —F, —Cl, —Br, —I, —CF$_3$, —CN, N$_3$, —NO$_3$, or —OR$^4$;

$^{3b}$ is —O(R$^4$);

R$^{3c}$ is —R$^4$, —N(R$^4$)(R$^4$), —SR$^4$, —S(O)R$^4$, —S(O)$_2$R$^4$, —S(O)(OR$^4$), —S(O)$_2$(OR$^4$), —OC(R$^{3b}$)R$^4$, —OC(R$^{3b}$)OR$^4$, —OC(R$^{3b}$)(N(R$^4$)(R$^4$)), —SC(R$^{3b}$)R$^4$, —SC(R$^{3b}$)OR$^4$, —SC(R$^{3b}$)(N(R$^4$)(R$^4$)), —N(R$^4$)C(R$^{3b}$)R$^4$, —N(R$^4$)C(R$^{3b}$)OR$^4$, —N(R$^4$)C(R$^{3b}$)(N(R$^4$)(R$^4$)), W$^3$ or —R$^5$W$^3$;

R$^{3d}$ is —C(R$^{3b}$)R$^4$, —C(R$^{3b}$)OR$^4$, —C(R$^{3b}$)W$^3$, —C(R$^{3b}$)OW$^3$ —C(R$^{3b}$)(N(R$^4$)(R$^4$));

R$^4$ is —H, or an alkyl of 1 to 18 carbon atoms, alkenyl of 2 to 18 carbon atoms, or alkynyl of 2 to 18 carbon atoms;

R$^5$ is alkylene of 1 to 18 carbon atoms, alkenylene of 2 to 18 carbon atoms, or alkynylene of 2 to 18 carbon atoms; W$^3$ is W⁴ or W⁵; W⁴ is R⁶, —C(R³ᵇ)R⁶, —C(R³ᵇ)W⁵, —SO$_{M2}$R⁶, or —SO$_{M2}$W⁵, wherein R⁶ is R⁴;

W⁵ is carbocycle or heterocycle; and retips; and

M2 is 0, 1 or 2; and pharmaceutically acceptable salts thereof.

An embodiment of the present invention provides a compound of the Formula IA,

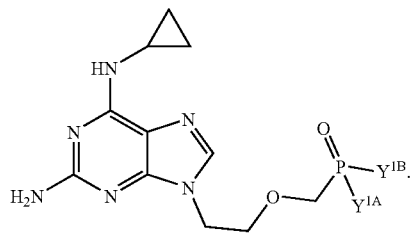

where $Y^{1A}$ and $Y^{1B}$ are as defined above.

An embodiment of the present invention provides a compound of the formula,

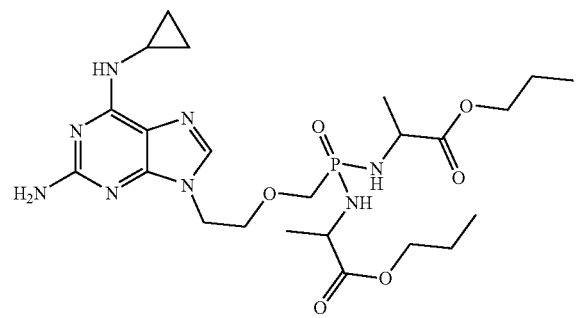

An embodiment of the present invention provides a compound of the formula,

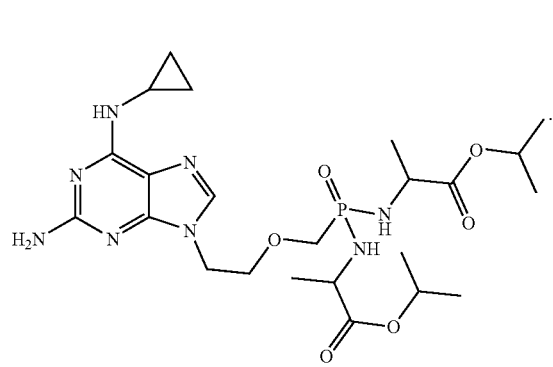

An embodiment of the present invention provides a compound of the formula,

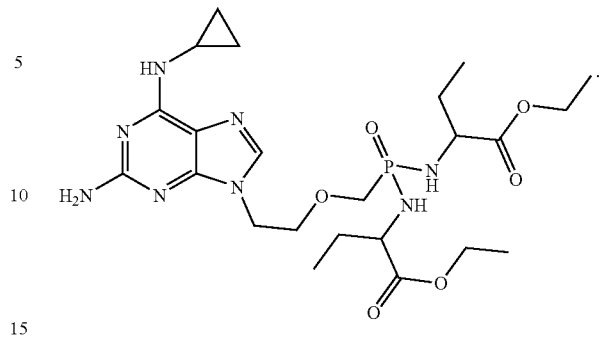

An embodiment of the present invention provides a compound of the formula,

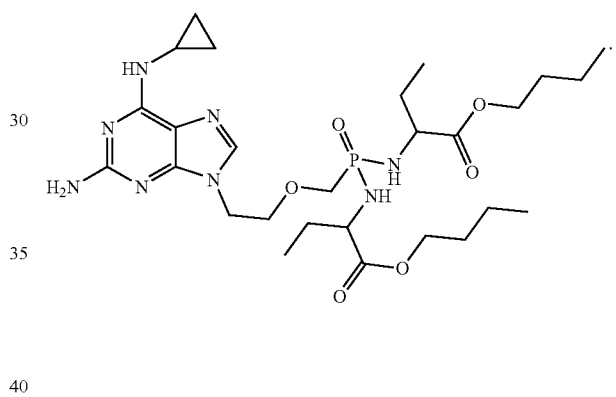

An embodiment of the present invention provides a compound of the formula,

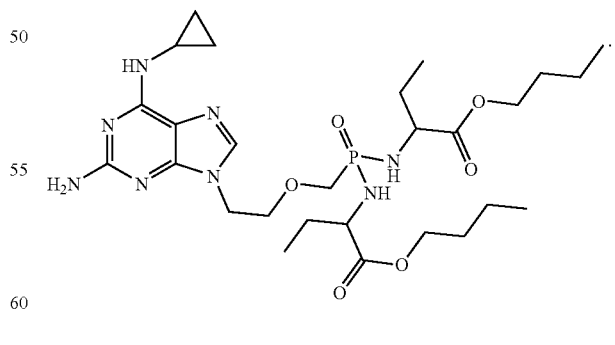

An embodiment of the present invention provides a compound of the formula,

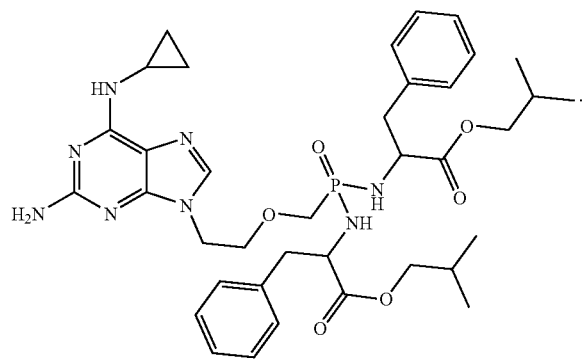

An embodiment of the present invention provides a compound of the formula,

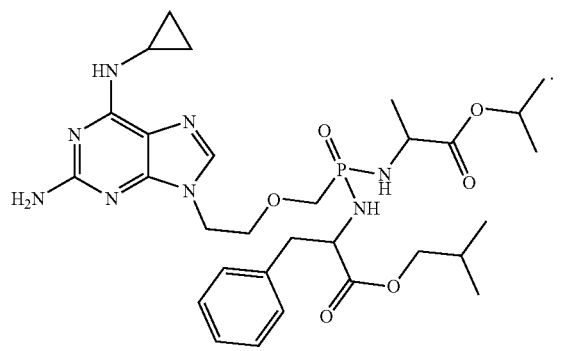

An embodiment of the present invention provides a compound of the formula,

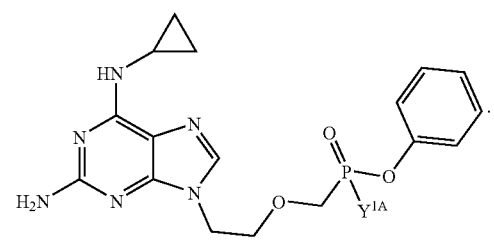

An embodiment of the present invention provides a compound of the formula,

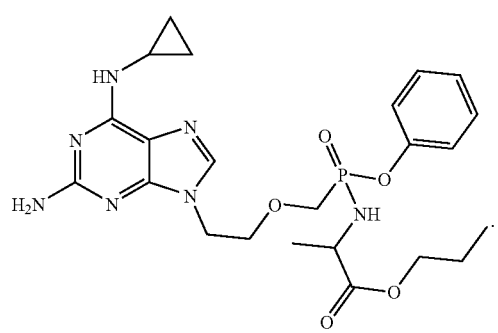

An embodiment of the present invention provides a compound of the formula,

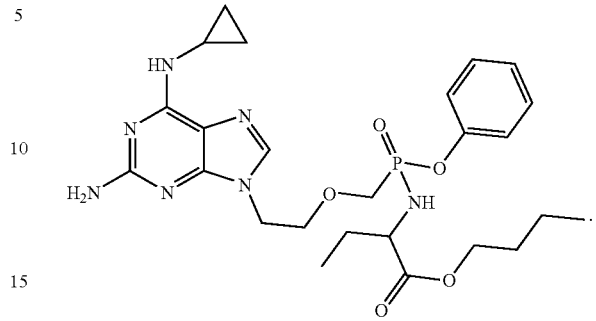

An embodiment of the present invention provides a compound of the formula,

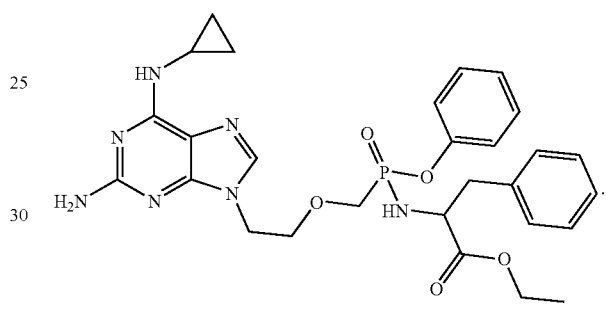

An embodiment of the present invention provides a compound useful as an antiproliferative agent.

An embodiment of the present invention provides a compound useful as an apoptotic agent.

An embodiment of the present invention provides a compound useful as an anti-HPV agent.

An aspect of the present embodiment provides a compound useful as a topical anti-HPV agent.

An embodiment of the present invention provides a pharmaceutical composition comprising an effective amount of a compound of Formula 1 or a pharmaceutically acceptable salt thereof, and a pharmaceutically acceptable carrier.

An aspect of the present embodiment provides a pharmaceutical composition, where the composition is a gel composition.

Another aspect of the present embodiment provides a pharmaceutical composition, where the composition is an ointment composition.

An embodiment of the present invention provides a pharmaceutical composition comprising an effective amount of a compound of Formula 1 or a pharmaceutically acceptable salt thereof, and an effective amount of at least one antiviral agent, and a pharmaceutically acceptable carrier.

An aspect of the present embodiment provides a pharmaceutical composition, where the composition is a gel composition.

Another aspect of the present embodiment provides a pharmaceutical composition, where the composition is an ointment composition.

DEFINITIONS

The term "PMEG" refers to the compound 9-(2-phosphonylmethoxyethyl)guanine,

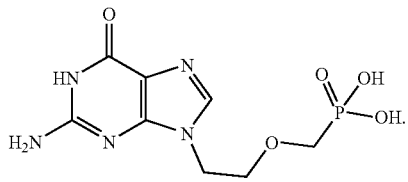

The term "PMEDAP" refers to the compound 9-(2-phosphonylmethoxyethyl)-2,6-diaminopurine,

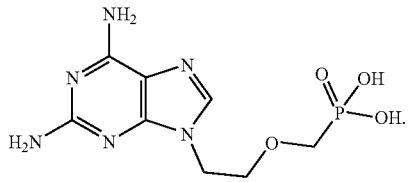

The term "cprPMEDAP" refers to the compound 9-(2-phosphonylmethoxyethyl)-2-amino-6-(cyclopropyl)purine,

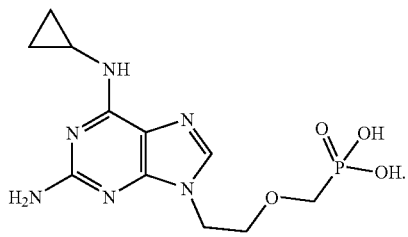

"Bioavailability" is the degree to which the pharmaceutically active agent becomes available to the target tissue after the agent's introduction into the body. Enhancement of the bioavailability of a pharmaceutically active agent can provide a more efficient and effective treatment for patients because, for a given dose, more of the pharmaceutically active agent will be available at the targeted tissue sites.

The terms "phosphonate" and "phosphonate group" include functional groups or moieties within a molecule that comprises a phosphorous that is 1) single-bonded to a carbon, 2) double-bonded to a heteroatom, 3) single-bonded to a heteroatom, and 4) single-bonded to another heteroatom, wherein each heteroatom can be the same or different. The terms "phosphonate" and "phosphonate group" also include functional groups or moieties that comprise a phosphorous in the same oxidation state as the phosphorous described above, as well as functional groups or moieties that comprise a prodrug moiety that can separate from a compound so that the compound retains a phosphorous having the characteristics described above. For-example, the terms "phosphonate" and "phosphonate group" include phosphonic acid, phosphonic monoester, phosphonic diester, phosphonamidate, and phosphonthioate functional groups. In one specific embodiment of the invention, the terms "phosphonate" and "phosphonate group" include functional groups or moieties within a molecule that comprises a phosphorous that is 1) single-bonded to a carbon, 2) double-bonded to an oxygen, 3) single-bonded to an oxygen, and 4) single-bonded to another oxygen, as well as functional groups or moieties that comprise a prodrug moiety that can separate from a compound so that the compound retains a phosphorous having such characteristics. In another specific embodiment of the invention, the terms "phosphonate" and "phosphonate group" include functional groups or moieties within a molecule that comprises a phosphorous that is 1) single-bonded to a carbon, 2) double-bonded to an oxygen, 3) single-bonded to an oxygen or nitrogen, and 4) single-bonded to another oxygen or nitrogen, as well as functional groups or moieties that comprise a prodrug moiety that can separate from a compound so that the compound retains a phosphorous having such characteristics.

Recipes and methods for determining stability of compounds in surrogate gastrointestinal secretions are known. Compounds are defined herein as stable in the gastrointestinal tract where less than about 50 mole percent of the protected groups are deprotected in surrogate intestinal or gastric juice upon incubation for 1 hour at 37° C. Such compounds are suitable for use in this embodiment. Note that simply because the compounds are stable to the gastrointestinal tract does not mean that they cannot be hydrolyzed in vivo. Prodrugs typically will be stable in the digestive system but are substantially hydrolyzed to the parental drug in the digestive lumen, liver or other metabolic organ, or within cells in general.

The compounds of the invention can also exist as tautomeric isomers in certain cases. For example, ene-amine tautomers can exist for imidazole, guanidine, amidine, and tetrazole systems and all their possible tautomeric forms are within the scope of the invention.

The term "prodrug" as used herein refers to any compound that when administered to a biological system generates the drug substance, i.e. active ingredient, as a result of spontaneous chemical reaction(s); enzyme catalyzed chemical reaction(s), photolysis, and/or metabolic chemical reaction(s). A prodrug is thus a covalently modified analog or latent form of a therapeutically-active compound.

"Prodrug moiety" refers to a labile functional group which separates from the active inhibitory compound during metabolism, systemically, inside a cell, by hydrolysis, enzymatic cleavage, or by some other process (Bundgaard, Hans, "Design and Application of Prodrugs" in *A Textbook of Drug Design and Development* (1991), P. Krogsgaard-Larsen and H. Bundgaard, Eds. Harwood Academic Publishers, pp. 113-191). Enzymes which are capable of an enzymatic activation mechanism with the phosphonate prodrug compounds of the invention include, but are not limited to, amidases, esterases, microbial enzymes, phospholipases, cholinesterases, and phosphases. Prodrug moieties can serve to enhance solubility, absorption and lipophilicity to optimize drug delivery, bioavailability and efficacy. A prodrug moiety may include an active metabolite or drug itself.

Exemplary prodrug moieties include the hydrolytically sensitive or labile acyloxymethyl esters —$CH_2OC(=O)R$ and acyloxymethyl carbonates —$CH_2OC(=O)OR$ where R in this instance is $C_1$-$C_6$ alkyl, $C_1$-$C_6$ substituted alkyl, $C_6$-$C_{20}$ aryl or $C_6$-$C_{20}$ substituted aryl. The acyloxyalkyl ester was first used as a prodrug strategy for carboxylic acids and then applied to phosphates and phosphonates by Farquhar et al. (1983) *J. Pharm. Sci.* 72: 324; also U.S. Pat. Nos. 4,816,570, 4,968,788, 5,663,159 and 5,792,756. Subsequently, the acyloxyalkyl ester was used to deliver phosphonic acids across cell membranes and to enhance oral bioavailability. A close variant of the acyloxyalkyl ester, the alkoxycarbonyloxyalkyl ester (carbonate), may also enhance oral bioavailability as a prodrug moiety in the compounds of the combinations of the invention. An exemplary acyloxymethyl ester is isopropyl-carbonyloxymethoxy, —OCH$_2$OC(=O)C(CH$_3$)$_2$. An exemplary acyloxymethyl carbonate prodrug moiety is isopropyl-carbonyloxymethyl carbonate, HOC(=O)OCH$_2$OC(=O)C(CH$_3$)$_2$.

The phosphonate group may be a phosphonate prodrug moiety. The prodrug moiety may be sensitive to hydrolysis, such as, but not limited to a isopropylcarbonyl-oxymethoxy or isopropylcarbonyloxymethyl carbonate group. Alternatively, the prodrug moiety may be sensitive to enzymatic potentiated cleavage, such as a lactate ester or a phosphonamidate-ester group.

Aryl esters of phosphorus groups, especially phenyl esters, are reported to enhance oral bioavailability (De Lombaert et al. (1994) *J. Med. Chem.* 37:498). Phenyl esters containing a carboxylic ester ortho to the phosphate have also been described (Khamnei and Torrence, (1996) *J. Med. Chem.* 39:4109-4115). Benzyl esters are reported to generate the parent phosphonic acid. In some cases, substituents at the ortho-or para-position may accelerate the hydrolysis. Benzyl analogs with an acylated phenol or an alkylated phenol may generate the phenolic compound through the action of enzymes, e.g., esterases, oxidases, etc., which in turn undergoes cleavage at the benzylic C—O bond to generate the phosphoric acid and the quinone methide intermediate. Examples of this class of prodrugs are described by Mitchell et al. (1992) *J. Chem. Soc. Perkin Trans. II* 2345; Glazier WO 91/19721. Still other benzylic prodrugs have been described containing a carboxylic ester-containing group attached to the benzylic methylene (Glazier WO 91/19721). Thio-containing prodrugs are reported to be useful for the intracellular delivery of phosphonate drugs. These proesters contain an ethylthio group in which the thiol group is either esterified with an acyl group or combined with another thiol group to form a disulfide. Deesterification or reduction of the disulfide generates the free thio intermediate which subsequently breaks down to the phosphoric acid and episulfide (Puech et al. (1993) *Antiviral Res.,* 22: 155-174; Benzaria et al. (1996) *J. Med. Chem.* 39: 4958). Cyclic phosphonate esters have also been described as prodrugs of phosphorus-containing compounds (Erion et al., U.S. Pat. No. 6,312,662).

"Protecting group" refers to a moiety of a compound that masks or alters the properties of a functional group or the properties of the compound as a whole. Chemical protecting groups and strategies for protection/deprotection are well known in the art. See e.g., *Protective Groups in Organic Chemistry,* Theodora W. Greene, John Wiley & Sons, Inc., New York, 1991. Protecting groups are often utilized to mask the reactivity of certain functional groups, to assist in the efficiency of desired chemical reactions, e.g., making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive.

Protected compounds may also exhibit altered, and in some cases, optimized properties in vitro and in vivo, such as passage through cellular membranes and resistance to enzymatic degradation or sequestration. In this role, protected compounds with intended therapeutic effects may be referred to as prodrugs.

Another function of a protecting group is to convert the parental drug into a prodrug, whereby the parental drug is released upon conversion of the prodrug in vivo. Because active prodrugs may be absorbed more effectively than the parental drug, prodrugs may possess greater potency in vivo than the parental drug. Protecting groups are removed either in vitro, in the instance of chemical intermediates, or in vivo, in the case of prodrugs. With chemical intermediates, it is not particularly important that the resulting products after deprotection, e.g., alcohols, be physiologically acceptable, although in general it is more desirable if the products are pharmacologically innocuous.

Any reference to any of the compounds of the invention also includes a reference to a physiologically acceptable salt thereof. Examples of physiologically acceptable salts of the compounds of the invention include salts derived from an appropriate base, such as an alkali metal (for example, sodium), an alkaline earth (for example, magnesium), ammonium and NX$_4^+$ (wherein X is C$_1$-C$_4$ alkyl). Physiologically acceptable salts of an hydrogen atom or an amino group include salts of organic carboxylic acids such as acetic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, sulfuric, phosphoric and sulfamic acids. Physiologically acceptable salts of a compound of a hydroxy group include the anion of said compound in combination with a suitable cation such as Na$^+$ and NX$_4^+$ (wherein X is independently selected from H or a C$_1$-C$_4$ alkyl group).

As used herein, the term "gel" refers to semisolid systems consisting of either suspensions made up of small inorganic particles or large organic molecules enclosing and interpenetrated by a liquid. Where the gel mass consists of floccules of small particles, the gel is classified as a two-phase system and is sometimes called a magma. Aluminum Hydroxide Gel and Bentonite Magma are examples of two-phase systems. Single-phase gels consist of organic macromolecules uniformly distributed throughout a liquid in such a manner that no apparent boundaries exist between the dispersed macromolecules and the liquid. Examples of such gels are Carboxymethylcellulose Sodium and Tragacanth. Although gels are commonly aqueous, alcohols and oils may be used as a continuous phase.

As used herein the term "ointment" refers to a semisolid preparation for external application of such consistency that they may be readily applied to skin by inunction. They should be of such composition that they soften but not necessarily melt when applied to the body. They serve as vehicles for the topical application of medicinal substances and also function as protectives and emollients for the skin.

For therapeutic use, salts of active ingredients of the compounds of the invention will be physiologically acceptable, i.e. they will be salts derived from a physiologically acceptable acid or base. However, salts of acids or bases which are not physiologically acceptable may also find use, for example, in the preparation or purification of a physiologically acceptable compound. All salts, whether or not derived form a physiologically acceptable acid or base, are within the scope of the present invention.

"Alkyl" is C$_1$-C$_{18}$ hydrocarbon containing normal, secondary, tertiary or cyclic carbon atoms. Examples are methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$.

"Alkenyl" is C$_2$-C$_{18}$ hydrocarbon containing normal, secondary, tertiary or cyclic carbon atoms with at least one site of unsaturation, i.e. a carbon-carbon, sp$^2$ double bond. Examples include, but are not limited to, ethylene or vinyl (—CH=CH$_2$), allyl (—CH$_2$ CH=CH$_2$), cyclopentenyl (—C$_5$H$_7$), and 5-hexenyl (—CH$_2$CH$_2$CH$_2$CH$_2$CH=CH$_2$).

"Alkynyl" is C$_2$-C$_{18}$ hydrocarbon containing normal, secondary, tertiary or cyclic carbon atoms with at least one site of unsaturation, i.e. a carbon-carbon, sp triple bond. Examples include, but are not limited to, acetylenic (—C≡CH) and propargyl (—CH$_2$C≡CH), "Alkylene" refers to a saturated, branched or straight chain or cyclic hydrocarbon radical of 1-18 carbon atoms, and having two monovalent radical centers derived by the removal of two hydrogen atoms from the same or two different carbon atoms of a parent alkane. Typical alkylene radicals include, but are not limited to, methylene (—CH$_2$—) 1,2-ethyl (—CH$_2$CH$_2$—), 1,3-propyl (—CH$_2$CH$_2$CH$_2$—), 1,4-butyl (—CH$_2$CH$_2$CH$_2$—), and the like.

"Alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene. Typical alkenylene radicals include, but are not limited to, 1,2-ethylene (—CH=CH—).

"Alkynylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkyne. Typical alkynylene radicals include, but are not limited to, acetylene (—C≡C—), propargyl (—CH$_2$C≡C—), and 4-pentynyl (—CH$_2$CH$_2$CH$_2$C≡CH—).

"Aryl" means a monovalent aromatic hydrocarbon radical of 6-20 carbon atoms derived by the removal of one hydrogen atom from a single carbon atom of a parent aromatic ring system. Typical aryl groups include, but are not limited to, radicals derived from benzene, substituted benzene, naphthalene, anthracene, biphenyl, and the like.

"Arylalkyl" refers to an acyclic alkyl radical in which one of the hydrogen atoms bonded to a carbon atom, typically a terminal or sp$^3$ carbon atom, is replaced with an aryl radical. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl group comprises 6 to 20 carbon atoms, e.g., the alkyl moiety, including alkyl alkenyl or alkynyl groups, of the arylalkyl group is 1 to 6 carbon atoms and the aryl moiety is 5 to 14 carbon atoms.

"Substituted alkyl", "substituted aryl", and "substituted arylalkyl" mean alkyl, aryl, and arylalkyl respectively, in which one or more hydrogen atoms are each independently replaced with a non-hydrogen substituent. Typical substituents include, but are not limited to, —X, —R, —O$^-$, —OR, —SR, —S$^-$, —NR$_2$, —NR$_3$, =NR, —CX$_3$, —CN, —OCN, —SCN, —N=C=O, —NCS, —NO, —NO$_2$, =N$_2$, —N$_3$, NC(=O)R, —C(=O)R, —C(=O)NRR —S(=O)$_2$O$^-$, —S(=O)$_2$OH, —S(=O)$_2$R, —OS(=O)$_2$OR, —S(=O)$_2$NHR, —S(=O)R, —OP(=O)$_2$ORR, —P(=O)$_2$ORR —P(=O)(O$^-$)$_2$, —P(=O)(OH)$_2$, —C(=O)R, —C(=O)X, —C(S)R, —C(O)OR, —C(O)O$^-$, —C(S)OR, —C(O)SR, —C(S)SR, —C(O)NRR, —C(S)NRR, —C(NR)NRR, where each X is independently a halogen: F, Cl, Br, or I; and each R is independently —H, alkyl, aryl, heterocycle, protecting group or prodrug moiety. Alkylene, alkenylene, and alkynylene groups may also be similarly substituted.

"Heterocycle" as used herein includes by way of example and not limitation these heterocycles described in Paquette, Leo A.; *Principles of Modern Heterocyclic Chemistry* (W. A. Benjamin, New York, 1968), particularly Chapters 1, 3, 4, 6, 7, and 9; *"The Chemistry of Heterocyclic Compounds, A Series of Monographs"* (John Wiley & Sons, New York, 1950 to present), in particular Volumes 13, 14, 16, 19, and 28; and *J. Am. Chem. Soc.* (1960) 82:5566. In one specific embodiment of the invention "heterocycle" includes a "carbocycle" as defined herein, wherein one or more (e.g. 1, 2, 3, or 4) carbon atoms have been replaced with a heteroatom (e.g. O, N, or S).

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Carbocycle" refers to a saturated, unsaturated or aromatic ring having 3 to 7 carbon atoms as a monocycle, 7 to 12 carbon atoms as a bicycle, and up to about 20 carbon atoms as a polycycle. Monocyclic carbocycles have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atom arranged as a bicyclo [5,6] or [6,6] system. Examples of monocyclic carbocycles include cyclopropyl(cPropyl), cyclobutyl(cButyl), cyclopentyl(cPentyl), 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl, spiryl and naphthyl.

"Linker" or "link" refers to a chemical moiety comprising a covalent bond or a chain or group of atoms that covalently attaches a phosphonate group to a drug. Linkers include moieties such as: repeating units of alkyloxy (e.g., polyethyleneoxy, PEG, polymethyleneoxy) and alkylamino (e.g., polyethyleneamino, Jeffamine™); and diacid ester and amides including succinate, succinamide, diglycolate, malonate, and caproamide.

As used herein the term "Aba" refers to a divalent moiety of 2-aminobutanoic acid,

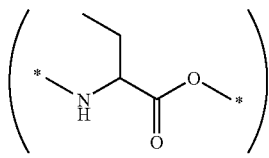

where the points of attachment are designated by the "*".

As used herein the term "Ala" refers to a divalent moiety of alanine,

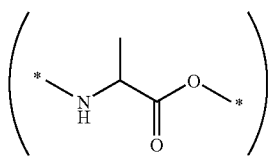

where the points of attachment are designated by the "*".

As used herein the term "Phe" refers to a divalent moiety of alanine,

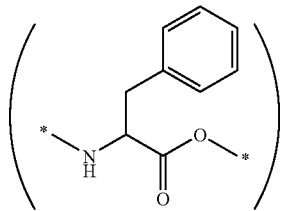

where the points of attachment are designated by the "*".

As used herein the term "Ala" refers to a divalent moiety of alanine,

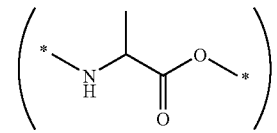

where the points of attachment are designated by the "*".

As used herein the term "POC" refers to the divalent moiety of hydroxymethyl isopropyl carbonate,

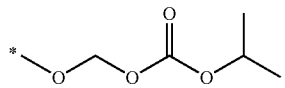

where the point of attachment is designated by the "*".

Substituent groups $Y^{1A}$ and $Y^{1B}$ can be described using nomenclature that incorporates the aforementioned divalent amino acid moieties and alkyl moieties, such as in Table 80-3.

For example, the compound of the formula,

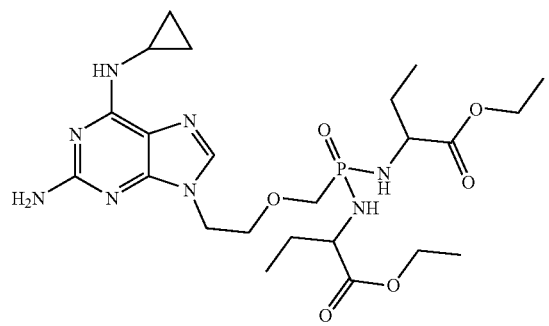

can be described using the nomenclature of Formula I, where $Y^{1A}$ and $Y^{1B}$ are $-N(R^X)$, where $R^X$ is $R^2$, where $R^2$ is $R^4$ substituted with $R^{3d}$, where $R^4$ is ethyl substituted with $R^{3d}$ further where $R^{3d}$ is $-C(R^{3b})OW^3$, where $R^{3b}$ is $=O$, where $W^3$ is $W^5$, where $W^5$ is a carbocycle, where $R^4$ is propyl substituted with $R^{3d}$, where $R^{3d}$ is $-C(R^{3b})OR^4$, where $R^{3b}$ is $=O$, and where $R^4$ is ethyl. Alternatively, said compound can be described, as in Table 80-3, as Formula I, where $Y^{1A}$ and $Y^{1B}$ are "Aba-Et", which describes the moiety (where the "*" indicates the point of attachment),

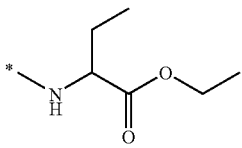

which is "Aba" linked to "Et" (ethyl).

For example, the compound of the formula,

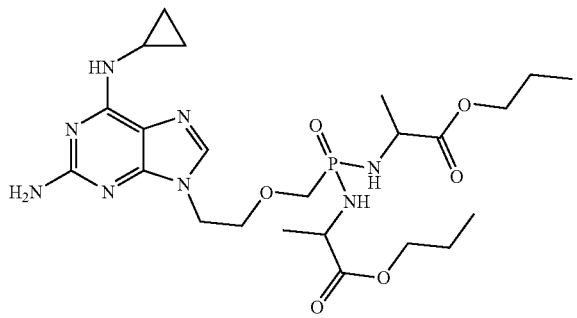

can be described using the nomenclature of Formula I, where $Y^{1A}$ and $Y^{1B}$ are —N($R^X$), where $R^X$ is $R^2$, where $R^2$ is $R^4$ substituted with $R^{3d}$, where $R^4$ is ethyl substituted with $R^{3d}$, where $R^{3d}$ is —C($R^{3b}$)$OR^4$, where $R^{3b}$ is =O, and where $R^4$ is n-propyl. Alternatively, said compound can be described, as in Table 80-3, as Formula I, where $Y^{1A}$ and $Y^{1B}$ are "Ala-nPr", which describes the moiety (where the "*" indicates the point of attachment),

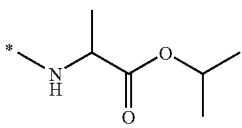

which is "Ala" linked to "nPr" (n-propyl).

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

The term "treatment" or "treating," to the extent it relates to a disease or condition includes preventing the disease or condition from occurring, inhibiting the disease or condition, eliminating the disease or condition, and/or relieving one or more symptoms of the disease or condition.

The term "antiproliferative" refers to activities used to, or tending to inhibit cell growth, such as antiproliferative effects on tumor cells, or antiproliferative effects on virally infected cells.

The terms "apoptosis" refers to one of the main types of programmed cell death. As such, it is a process of deliberate suicide by an unwanted cell in a multicellular organism. In contrast to necrosis, which is a form of cell death that results from acute tissue injury, apoptosis is carried out in an ordered process that generally confers advantages during an organism's life cycle. Apoptosis is a type of cell death in which the cell uses specialized cellular machinery to kill itself; a cell suicide mechanism that enables metazoans to control cell number and eliminate cells that threaten the animal's survival. Apoptosis can occur, for instance, when a cell is damaged beyond repair, or infected with a virus. The stimuli for apoptosis can come from the cell itself, from its surrounding tissue or from a cell that is part of the immune system, it can be chemical, biological or physical. The related term "apoptitic" refers to the process of apoptosis.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

Protecting Groups

In the context of the present invention, protecting groups include prodrug moieties and chemical protecting groups.

Protecting groups are available, commonly known and used, and are optionally used to prevent side reactions with the protected group during synthetic procedures, i.e. routes or methods to prepare the compounds of the invention. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis. The PG groups do not need to be, and generally are not, the same if the compound is substituted with multiple PG. In general, PG will be used to protect functional groups such as carboxyl, hydroxyl, thio, or amino groups and to thus prevent side reactions or to otherwise facilitate the synthetic efficiency. The order of deprotection to yield free, deprotected groups is dependent upon the intended direction of the synthesis and the reaction conditions to be encountered, and may occur in any order as determined by the artisan.

Various functional groups of the compounds of the invention may be protected. For example, protecting groups for —OH groups (whether hydroxyl, carboxylic acid, phosphonic acid, or other functions) include "ether- or ester-forming groups". Ether- or ester-forming groups are capable of functioning as chemical protecting groups in the synthetic schemes set forth herein. However, some hydroxyl and thio protecting groups are neither ether- nor ester-forming groups, as will be understood by those skilled in the art, and are included with amides, discussed below.

A very large number of hydroxyl protecting groups and amide-forming groups and corresponding chemical cleavage reactions are described in *Protective Groups in Organic Synthesis,* Theodora W. Greene (John Wiley & Sons, Inc., New York, 1991, ISBN 0-471-62301-6) ("Greene"). See also Kocienski, Philip J.; *Protecting Groups* (Georg Thieme Verlag Stuttgart, New York, 1994), which is incorporated by reference in its entirety herein. In particular Chapter 1, Protecting Groups: An Overview, pages 1-20, Chapter 2, Hydroxyl Protecting Groups, pages 21-94, Chapter 3, Diol Protecting Groups, pages 95-117, Chapter 4, Carboxyl Protecting Groups, pages 118-154, Chapter 5, Carbonyl Protecting Groups, pages 155-184. For protecting groups for carboxylic acid, phosphonic acid, phosphonate, sulfonic acid and other protecting groups for acids see Greene as set forth below. Such groups include by way of example and not limitation, esters, amides, hydrazides, and the like.

Ether- and Ester-Forming Protecting Groups

Ester-forming groups include: (1) phosphonate ester-forming groups, such as phosphonamidate esters, phosphorothioate esters, phosphonate esters, and phosphon-bis-amidates; (2) carboxyl ester-forming groups, and (3) sulphur ester-forming groups, such as sulphonate, sulfate, and sulfinate.

The phosphonate moieties of the compounds of the invention may or may not be prodrug moieties, i.e. they may or may be susceptible to hydrolytic or enzymatic cleavage or modification. Certain phosphonate moieties are stable under most or nearly all metabolic conditions. For example, a dialkylphosphonate, where the alkyl groups are two or more carbons, may have appreciable stability in vivo due to a slow rate of hydrolysis.

Salts and Hydrates

The compositions of this invention optionally comprise salts of the compounds herein, especially pharmaceutically acceptable non-toxic salts containing, for example, $Na^+$, $Li^+$, $K^+$, $Ca^{++}$ and $Mg^{++}$. Such salts may include those derived by combination of appropriate cations such as alkali and alkaline earth metal ions or ammonium and quaternary amino ions with an acid anion moiety. Monovalent salts are preferred if a water soluble salt is desired.

Metal salts typically are prepared by reacting a compound of this invention with a metal hydroxide. Examples of metal salts which are prepared in this way are salts containing $Li^+$, $Na^+$, and $K^+$. A less soluble metal salt can be precipitated from the solution of a more soluble salt by addition of the suitable metal compound.

In addition, salts may be formed from acid addition of certain organic and inorganic acids, e.g., HCl, HBr, $H_2SO_4$, or organic sulfonic acids, to basic centers, or to acidic groups. Finally, it is to be understood that the compositions herein comprise compounds of the invention in their un-ionized, as well as zwitterionic form, and combinations with stoichiometric amounts of water as in hydrates.

Also included within the scope of this invention are the salts of the parental compounds with one or more amino acids. Any of the amino acids described above are suitable, especially the naturally-occurring amino acids found as protein components, although the amino acid typically is one bearing a side chain with a basic or acidic group, e.g., lysine, arginine or glutamic acid, or a neutral group such as glycine, serine, threonine, alanine, isoleucine, or leucine.

Methods of Inhibition of HPV

Another aspect of the invention relates to methods of inhibiting the activity of HPV comprising the step of treating a sample suspected of containing HPV with a compound of the invention.

Compositions of the invention act as inhibitors of HPV, as intermediates for such inhibitors or have other utilities as described below.

The treating step of the invention comprises adding the composition of the invention to the sample or it comprises adding a precursor of the composition to the sample. The addition step comprises any method of administration as described above.

If desired, the activity of HPV after application of the composition can be observed by any method including direct and indirect methods of detecting HPV activity. Quantitative, qualitative, and semi quantitative methods of determining HPV activity are all contemplated. Typically one of the screening methods described above are applied, however, any other method such as observation of the physiological properties of a living organism are also applicable.

Screens for HPV Inhibitors

Compounds and compositions of the invention are screened for therapeutic utility by measuring the $EC_{50}$, that is the concentration of compound that achieves 50% inhibition of cell growth. The ratio of $EC_{50}$ in HPV-uninfected and infected cells provides a measure of the selectivity of the compound for the virus infected cells. The protocols used to obtain these measures are taught in the Examples.

Pharmaceutical Formulations and Routes of Administration.

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the "Handbook of Pharmaceutical Excipients" (1986). Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11, but is ordinarily about 7 to 10.

One or more compounds of the invention (herein referred to in this context as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with the condition of the recipient. An advantage of the compounds of this invention is that they are orally bioavailable and can be dosed orally.

While it is possible for the active ingredients to be administered alone it may be preferable to present them as pharmaceutical formulations. The formulations, both for veterinary and for human use, of the invention comprise at least one active ingredient, as above defined, together with one or more acceptable carriers therefore and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the invention suitable for oral administration are prepared as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient there from.

For infections of the eye or other external tissues e.g. mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of influenza A or B infections as described below.

Formulations suitable for vaginal administration may be presented as pessaries, tampons, creams, gels, pastes, foams or spray formulations containing in addition to the active ingredient, such carriers are as known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier therefore.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention are used to provide controlled release pharmaceutical formulations containing as active ingredient one or more compounds of the invention ("controlled release formulations") in which the release of the active ingredient are controlled and regulated to allow less frequency dosing or to improve the pharmacokinetic or toxicity profile of a given active ingredient.

Effective dose of active ingredient depends at least on the nature of the condition being treated, toxicity, whether the compound is being used prophylactically (lower doses) or against an active influenza infection, the method of delivery, and the pharmaceutical formulation, and will be determined by the clinician using conventional dose escalation studies. It can be expected to be from about 0.0001 to about 100 mg/kg body weight per day; typically, from about 0.01 to about 10 mg/kg body weight per day; more typically, from about 0.01 to about 5 mg/kg body weight per day; most typically, from about 0.05 to about 0.5 mg/kg body weight per day. For example, for inhalation the daily candidate dose for an adult human of approximately 70 kg body weight will range from 1 mg to 1000 mg, preferably between 5 mg and 500 mg, and may take the form of single or multiple doses.

Active ingredients of the invention are also used in combination with other active ingredients. Such combinations are selected based on the condition to be treated, cross-reactivities of ingredients and pharmaco-properties of the combination. For example, when treating viral infections of the respiratory system, in particular influenza infection, the compositions of the invention are combined with antivirals (such as amantidine, rimantadine and ribavirin), mucolytics, expectorants, bronchialdilators, antibiotics, antipyretics, or analgesics. Ordinarily, antibiotics, antipyretics, and analgesics are administered together with the compounds of this invention.

Metabolites of the Compounds of the Invention

The present invention also provides the in vivo metabolic products of the compounds described herein, to the extent such products are novel and unobvious over the prior art. Such products may result for example from the oxidation, reduction, hydrolysis, amidation, esterification and the like of the administered compound, primarily due to enzymatic processes. Accordingly, the invention includes novel and unobvious compounds produced by a process comprising contacting a compound of this invention with a mammal for a period of time sufficient to yield a metabolic product thereof. Such products typically are identified by preparing a radiolabeled (e.g. $C^{14}$ or $H^3$) compound of the invention, administering it parenterally in a detectable dose (e.g. greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g. by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the invention even if they possess no neuraminidase inhibitory activity of their own.

Additional Uses for the Compounds of this Invention.

The compounds of this invention, or the biologically active substances produced from these compounds by hydrolysis or metabolism in vivo, are used as immunogens or for conjugation to proteins, whereby they serve as components of immunogenic compositions to prepare antibodies capable of binding specifically to the protein, to the compounds or to their metabolic products which retain immunologically recognized epitopes (sites of antibody binding). The immunogenic compositions therefore are useful as intermediates in the preparation of antibodies for use in diagnostic, quality control, or the like, methods or in assays for the compounds or their novel metabolic products. The compounds are useful for raising antibodies against otherwise non-immunogenic polypeptides, in that the compounds serve as haptenic sites stimulating an immune response that cross-reacts with the unmodified conjugated protein.

The hydrolysis products of interest include products of the hydrolysis of the protected acidic and basic groups discussed above. As noted above, the acidic or basic amides comprising immunogenic polypeptides such as albumin or keyhole limpet hemocyanin generally are useful as immunogens. The metabolic products described above may retain a substantial degree of immunological cross reactivity with the compounds of the invention. Thus, the antibodies of this invention will be capable of binding to the unprotected compounds of the invention without binding to the protected compounds; alternatively the metabolic products, will be capable of binding to the protected compounds and/or the metabolic products without binding to the protected compounds of the invention, or will be capable of binding specifically to any one or all three. The antibodies desirably will not substantially cross-react with naturally-occurring materials. Substantial cross-reactivity is reactivity under specific assay conditions for specific analytes sufficient to interfere with the assay results.

The immunogens of this invention contain the compound of this invention presenting the desired epitope in association with an immunogenic substance. Within the context of the invention such association means covalent bonding to form an immunogenic conjugate (when applicable) or a mixture of non-covalently bonded materials, or a combination of the above. Immunogenic substances include adjuvants such as Freund's adjuvant, immunogenic proteins such as viral, bacterial, yeast, plant and animal polypeptides, in particular keyhole limpet hemocyanin, serum albumin, bovine thyroglobulin or soybean trypsin inhibitor, and immunogenic polysaccharides. Typically, the compound having the structure of the desired epitope is covalently conjugated to an immunogenic polypeptide or polysaccharide by the use of a polyfunctional (ordinarily bifunctional) cross-linking agent. Methods for the manufacture of hapten immunogens are conventional per se, and any of the methods used heretofore for conjugating haptens to immunogenic polypeptides or the like are suitably employed here as well, taking into account the functional groups on the precursors or hydrolytic products which are available for cross-linking and the likelihood of producing antibodies specific to the epitope in question as opposed to the immunogenic substance.

Typically the polypeptide is conjugated to a site on the compound of the invention distant from the epitope to be recognized.

The conjugates are prepared in conventional fashion. For example, the cross-linking agents N-hydroxysuccinimide, succinic anhydride or alkN=C=Nalk are useful in preparing the conjugates of this invention. The conjugates comprise a compound of the invention attached by a bond or a linking group of 1-100, typically, 1-25, more typically 1-10 carbon atoms to the immunogenic substance. The conjugates are separated from starting materials and by products using chromatography or the like, and then are sterile filtered and vialed for storage.

Animals are typically immunized against the immunogenic conjugates or derivatives and antisera or monoclonal antibodies prepared in conventional fashion.

The compounds of this invention are useful as linkers or spacers in preparing affinity absorption matrices, immobilized enzymes for process control, or immunoassay reagents. The compounds herein contain a multiplicity of functional groups that are suitable as sites for cross-linking desired substances. For example, it is conventional to link affinity reagents such as hormones, peptides, antibodies, drugs, and the like to insoluble substrates. These insoluhlized reagents are employed in known fashion to absorb binding partners for the affinity reagents from manufactured preparations, diagnostic samples and other impure mixtures. Similarly, immobilized enzymes are used to perform catalytic conversions with facile recovery of enzyme. Bifunctional compounds are commonly used to link analytes to detectable groups in preparing diagnostic reagents.

Screening assays preferably use cells from particular tissues that are susceptible to HPV infection. Assays known in the art are suitable for determining in vivo bioavailability including intestinal lumen stability, cell permeation, liver homogenate stability and plasma stability assays. However, even if the ester, amide or other protected derivatives are not converted in vivo to the free carboxyl, amino or hydroxyl groups, they remain useful as chemical intermediates.

Utility for the present invention was taught using antiproliferation assays. Antiproliferation assays measure effect of compounds on proliferation of cultured cells. Cells are cultured for 7 days in the presence of various concentrations of compounds. On the $7^{th}$ day, cells are stained with dye, and intensity of staining (proportional to cell number) is measured by spectrophotometer. Data are plotted against compound concentrations, fitted to the sigmoid dose response curve, from which the compound concentration that reduces cell proliferation rate by 50% (50% effective concentration or $EC_{50}$) is determined. Active compounds in antiproliferation assays may be cytostatic (inhibit cell division) and/or cytocidal (kill cells). By performing antiproliferation assays in HPV positive cancer cells and normal cells, we identify compounds that inhibit proliferation of HPV positive cancer cells more efficiently than cells from normal human tissues.

Exemplary Methods of Making the Compounds of the Invention.

The invention also relates to methods of making the compositions of the invention. The compositions are prepared by any of the applicable techniques of organic synthesis. Many such techniques are well known in the art. However, many of the known techniques are elaborated in "Compendium of Organic Synthetic Methods" (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, jr., 1980; Vol. 5, Leroy G. Wade, Jr., 1984; and Vol. 6, Michael B. Smith; as well as March, J., "Advanced Organic Chemistry, Third Edition", (John Wiley & Sons, New York, 1985), "Comprehensive Organic Synthesis. Selectivity, Strategy & Efficiency in Modern Organic Chemistry. In 9 Volumes", Barry M. Trost, Editor-in-Chief (Pergamon Press, New York, 1993 printing).

A number of exemplary methods for the preparation of the compositions of the invention are provided below. These methods are intended to illustrate the nature of such preparations are not intended to limit the scope of applicable methods.

Generally, the reaction conditions such as temperature, reaction time, solvents, workup procedures, and the like, will be those common in the art for the particular reaction to be performed. The cited reference material, together with material cited therein, contains detailed descriptions of such conditions. Typically the temperatures will be −100° C. to 200° C., solvents will be aprotic or protic, and reaction times will be 10 seconds to 10 days. Workup typically consists of quenching any unreacted reagents followed by partition between a water/organic layer system (extraction) and separating the layer containing the product.

Oxidation and reduction reactions are typically carried out at temperatures near room temperature (about 20° C.), although for metal hydride reductions frequently the temperature is reduced to 0C to −100° C., solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures (0C to −100° C.) are also common. Solvents can be either protic (common in equilibrating reactions) or aprotic (common in kinetically controlled reactions).

Standard synthetic techniques such as azeotropic removal of reaction by-products and use of anhydrous reaction conditions (e.g. inert gas environments) are common in the art and will be applied when applicable.

Exemplary methods of preparing the compounds of the invention are shown in the schemes below. Detailed descriptions of the methods are found in the Experimental section below, and are referenced to the specific schemes.

Schemes

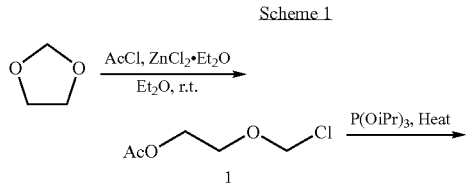

Scheme 1

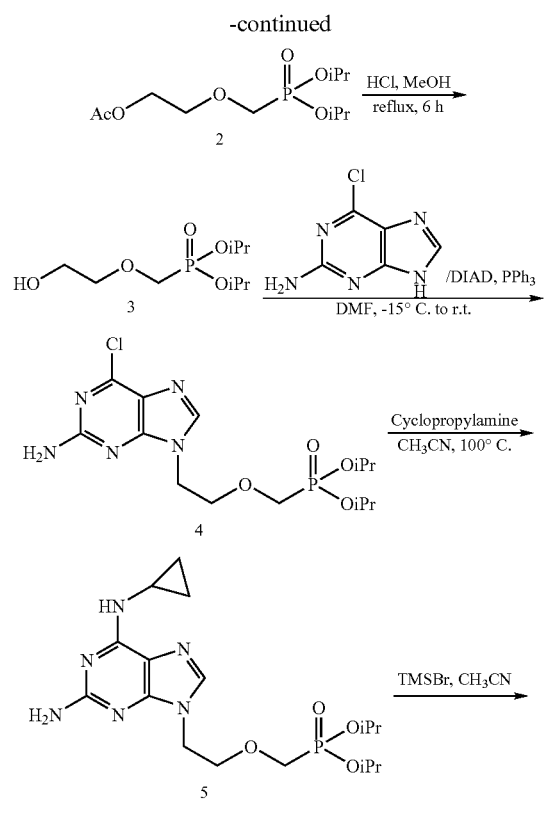
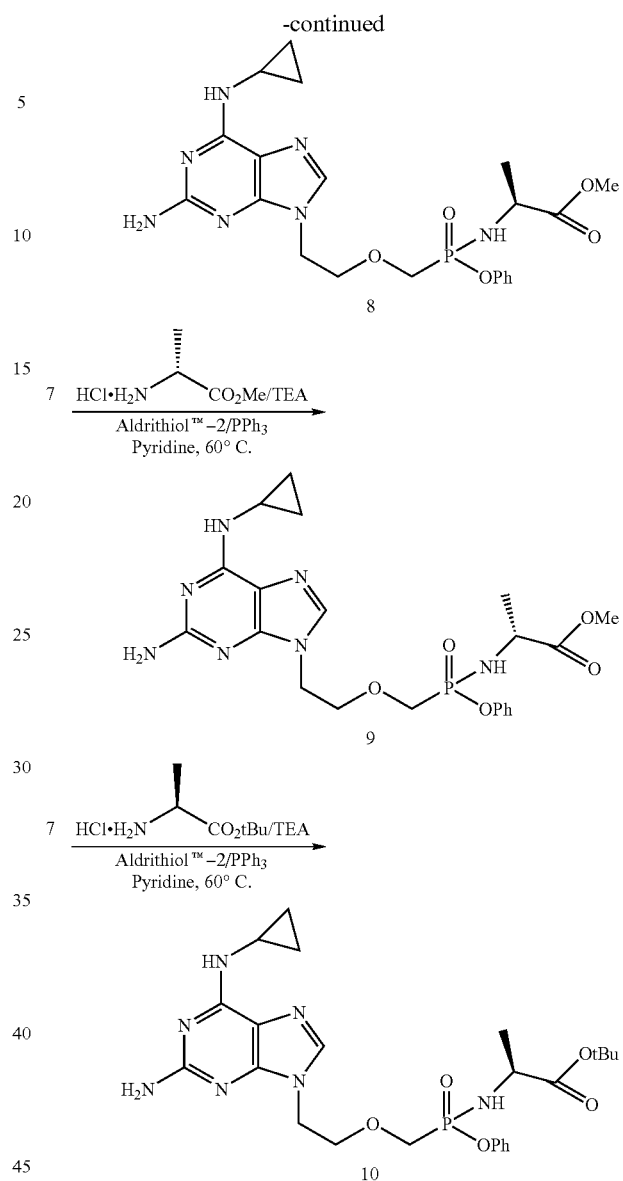
Scheme 2
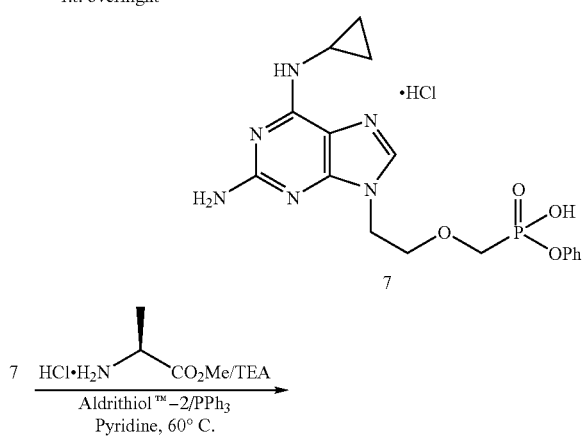
Scheme 3
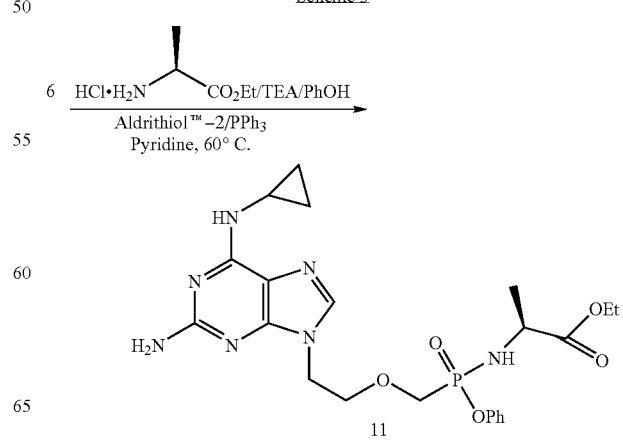

-continued
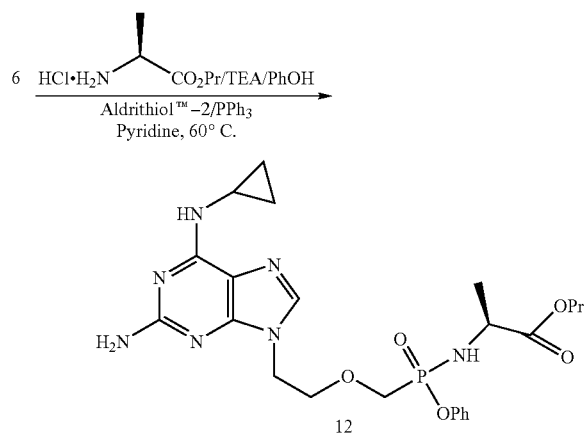
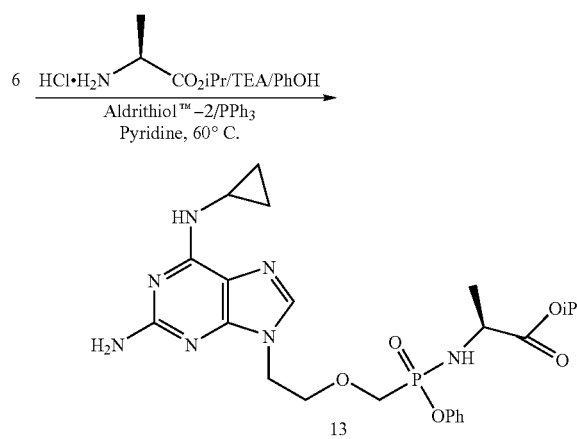
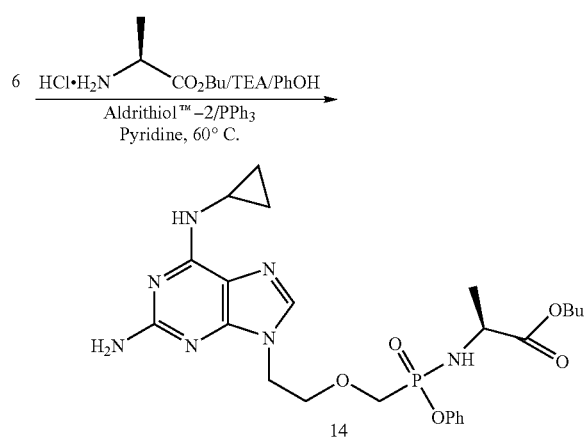
Scheme 4
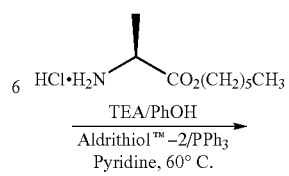
-continued
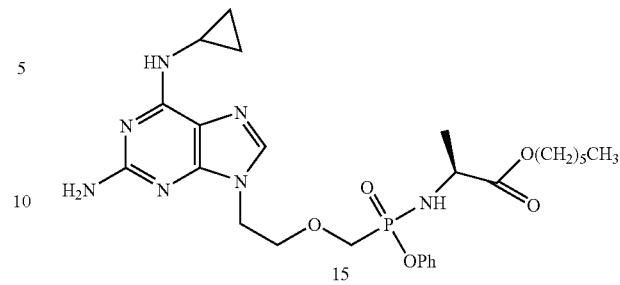
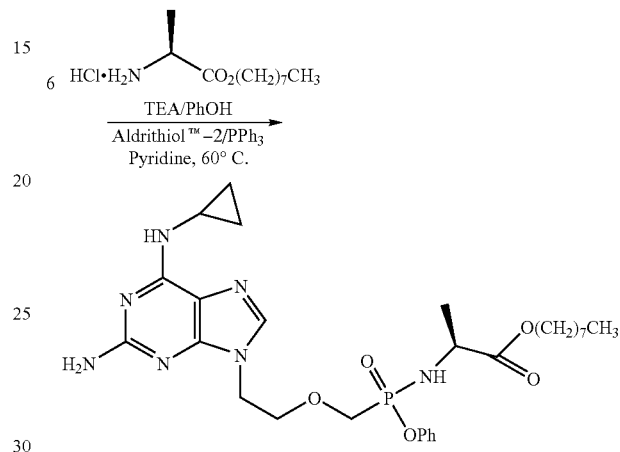
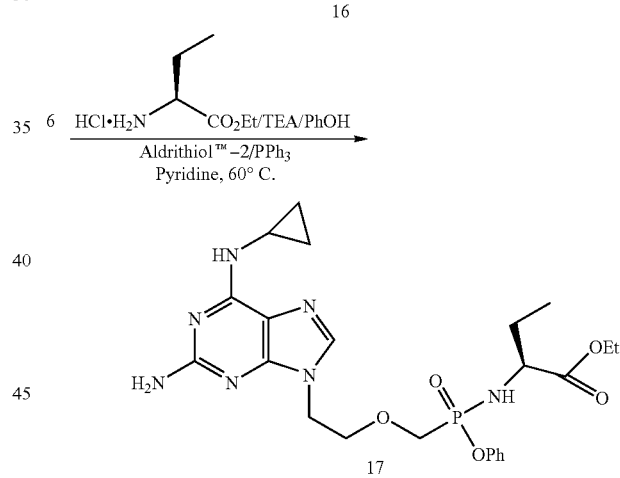
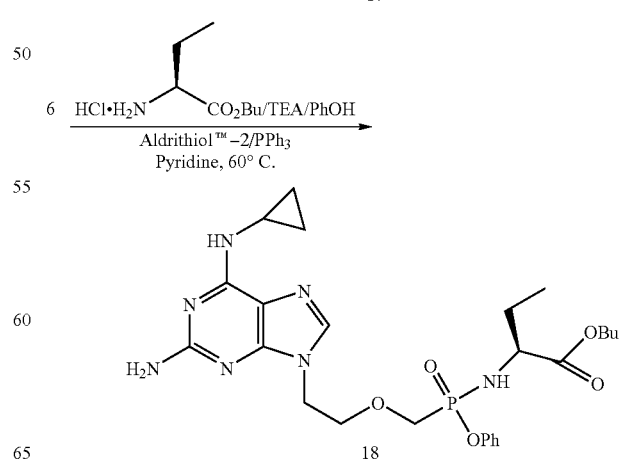

Scheme 5
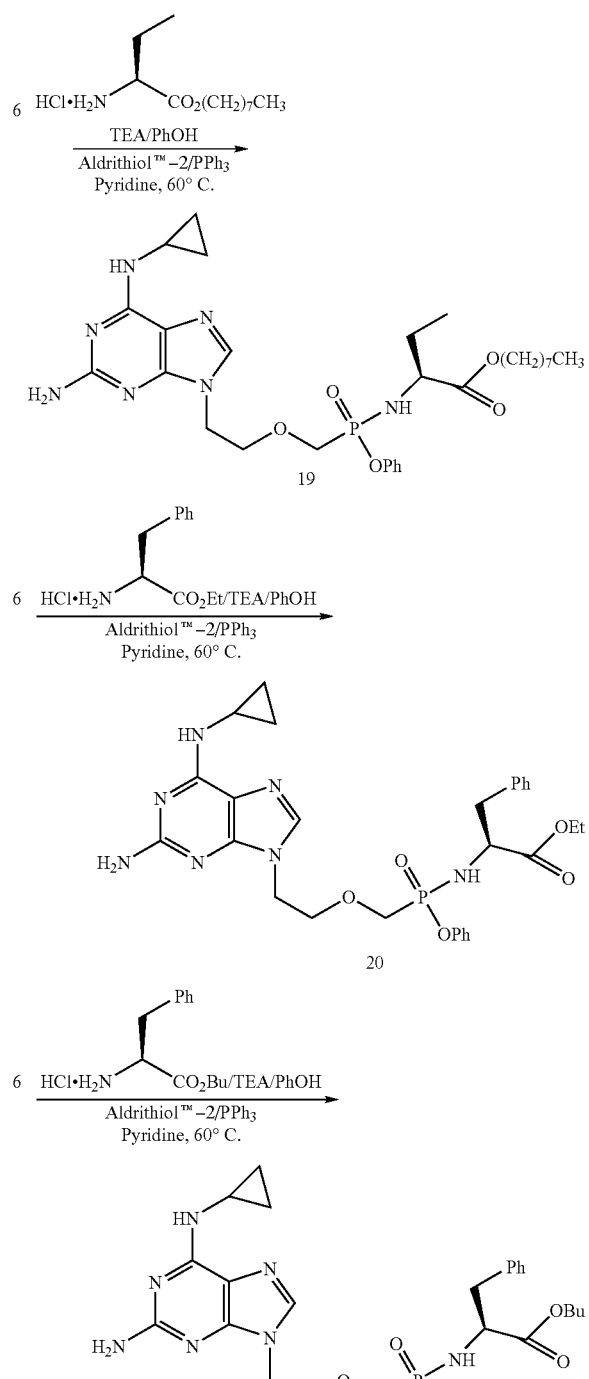
Scheme 6
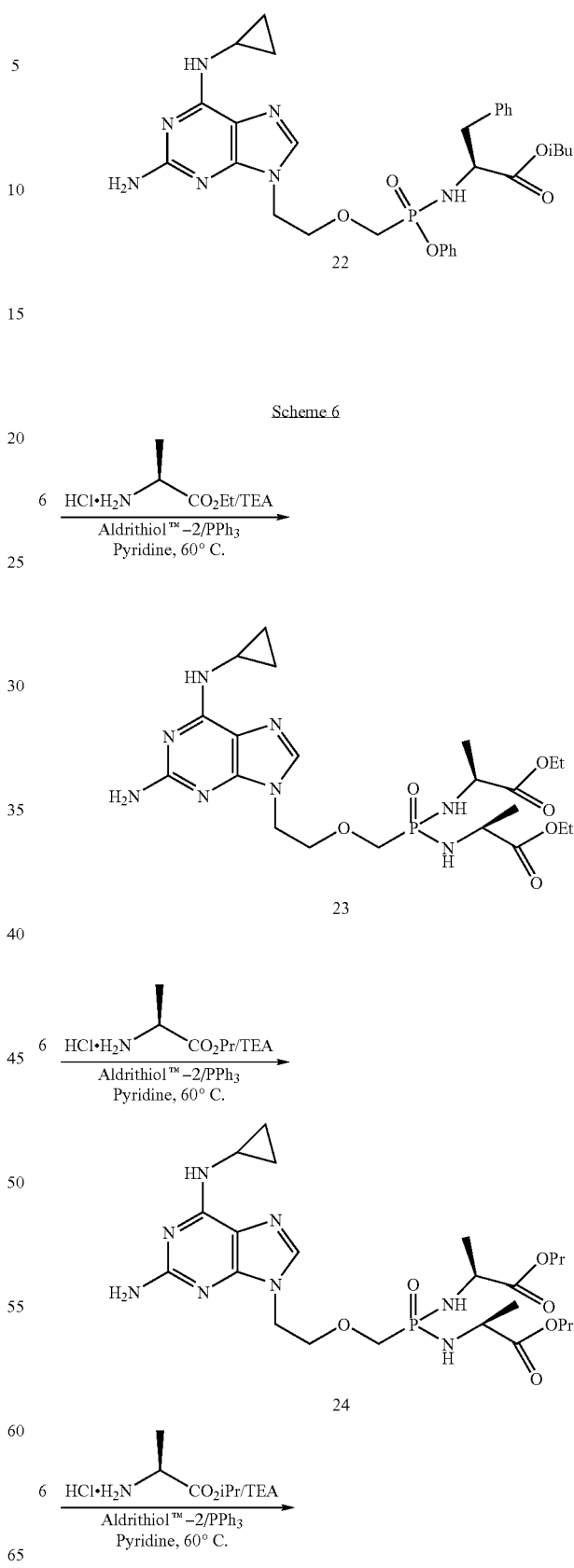

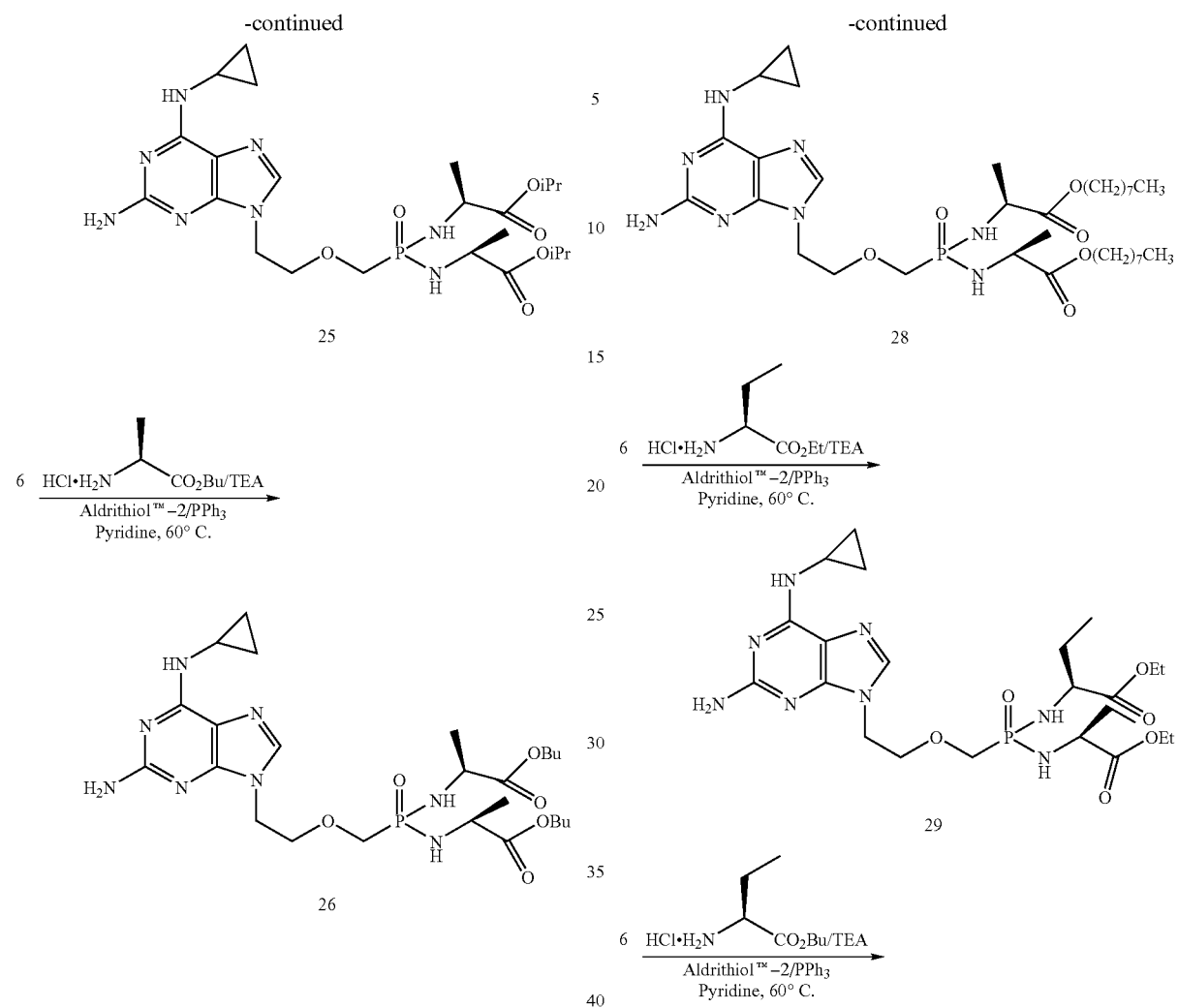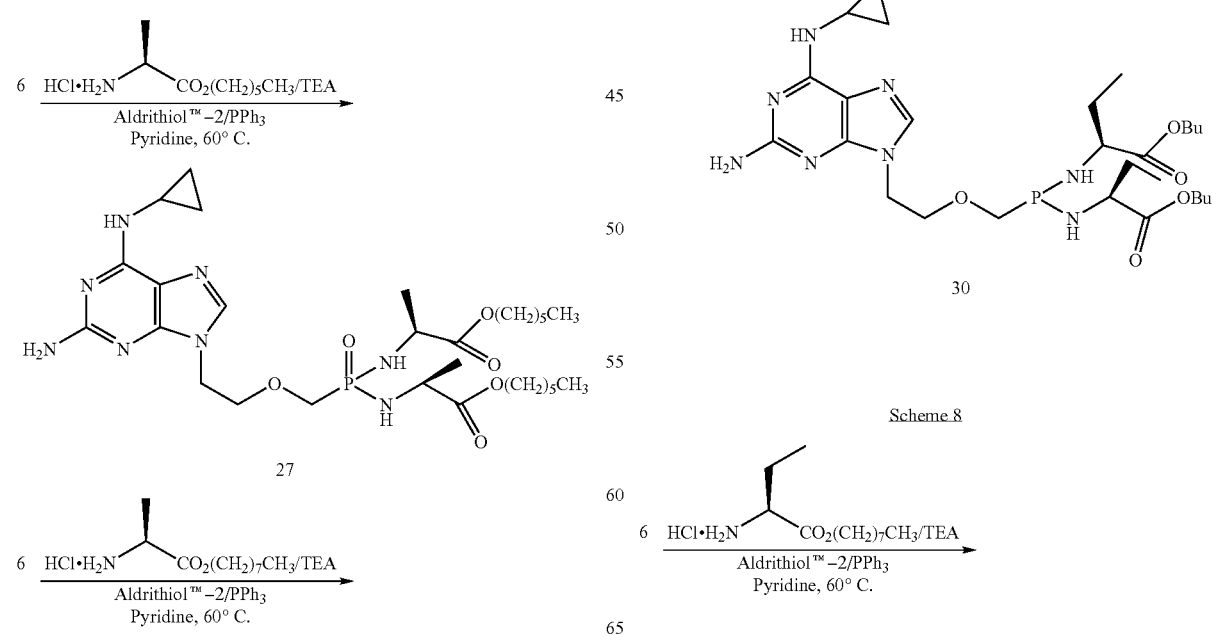

-continued
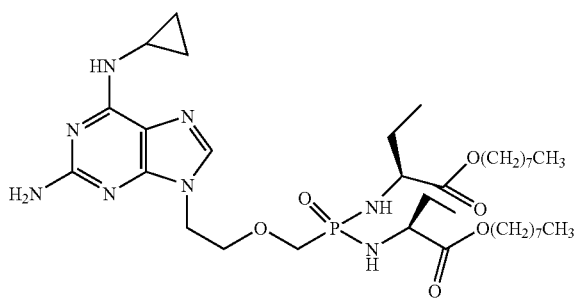
31
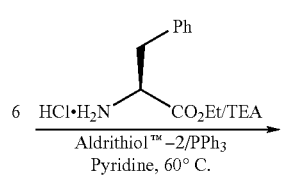
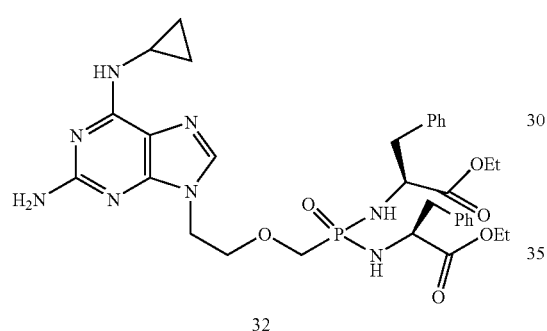
32
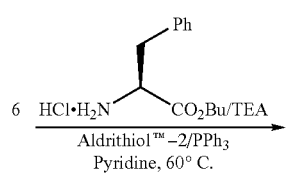
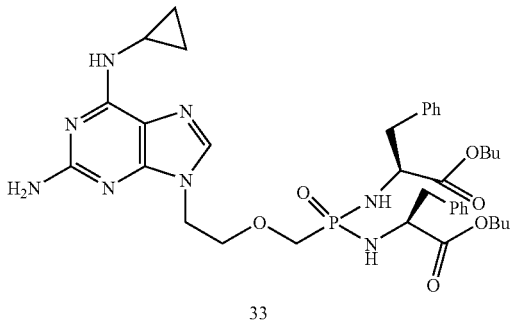
33
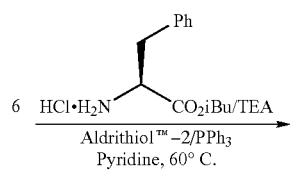
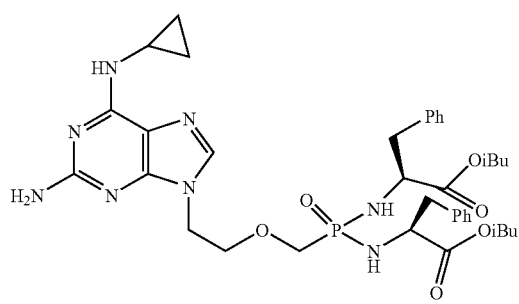
34
Scheme 9
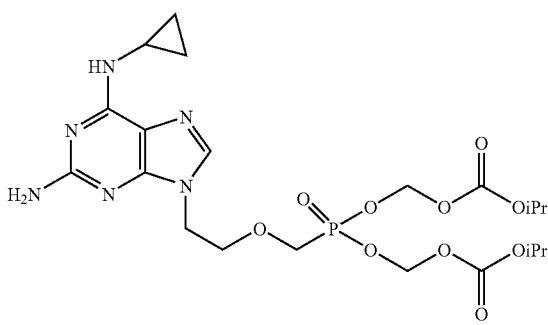
35
Scheme 10
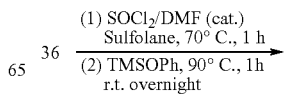
36
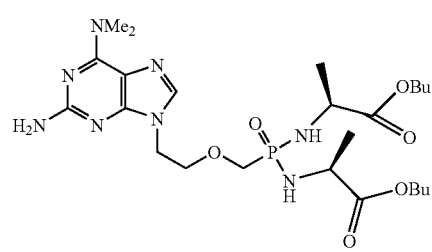
37
36 (1) SOCl$_2$/DMF (cat.) Sulfolane, 70° C., 1 h
(2) TMSOPh, 90° C., 1h
r.t. overnight

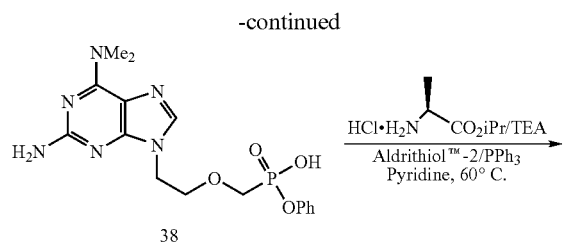
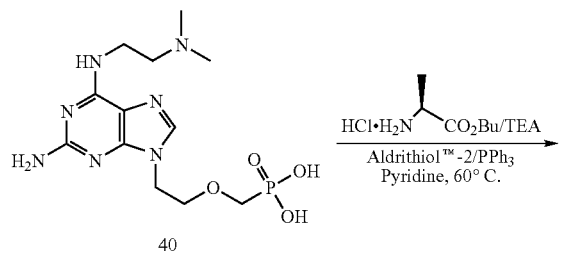
Scheme 11
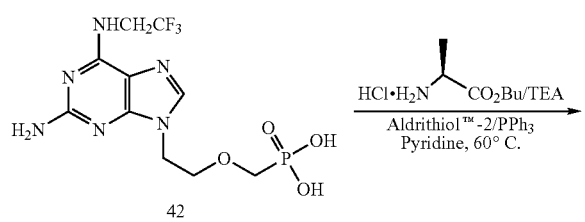
Scheme 12
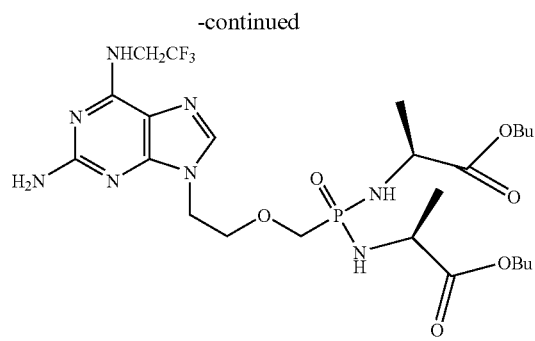
Scheme 13
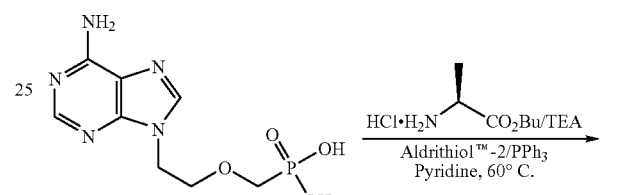
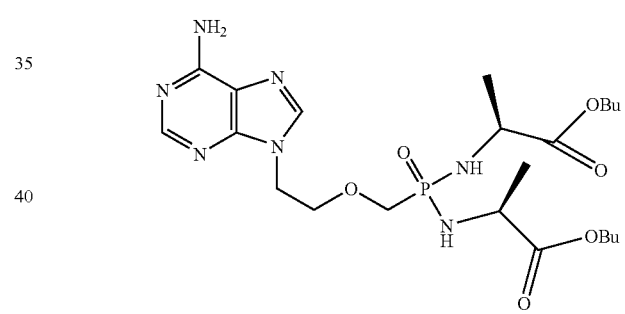
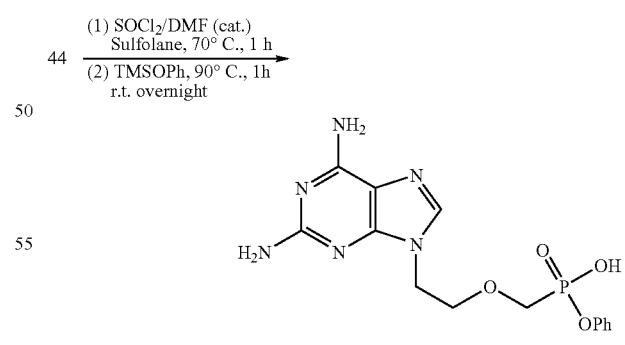
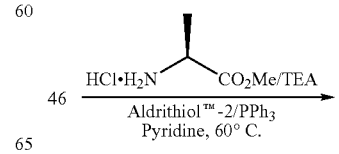

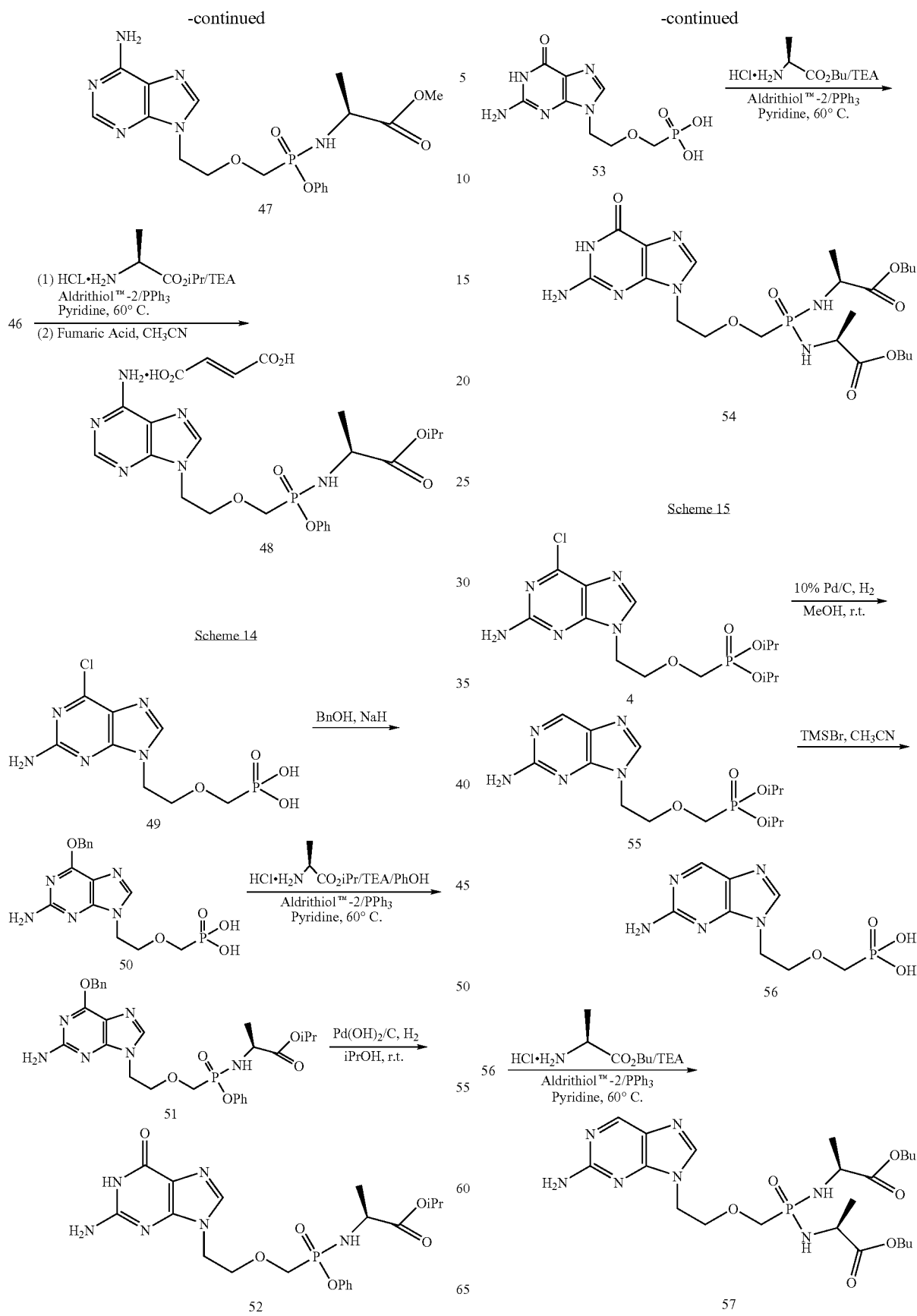

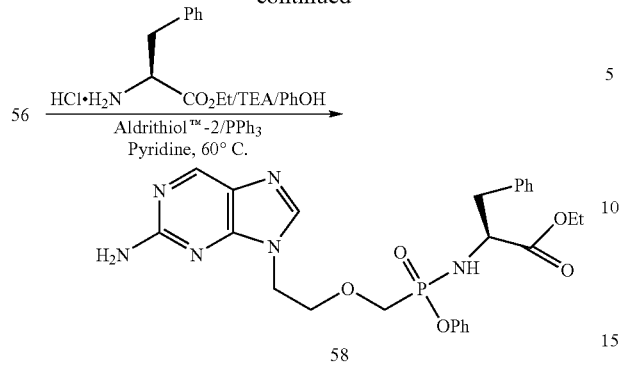
Scheme 16
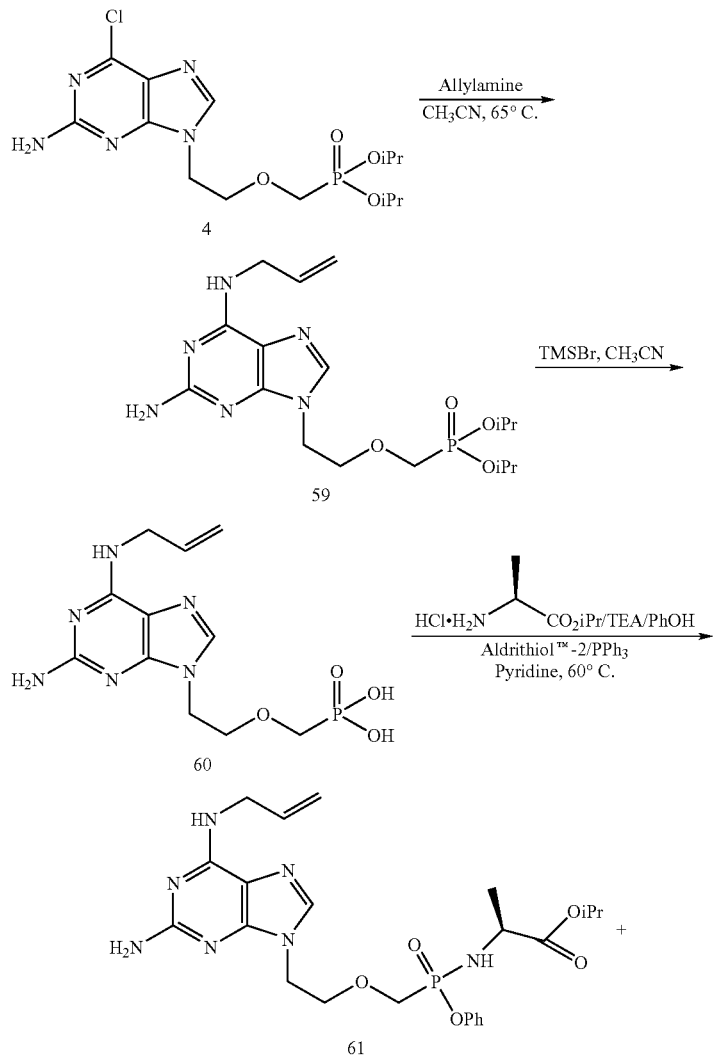

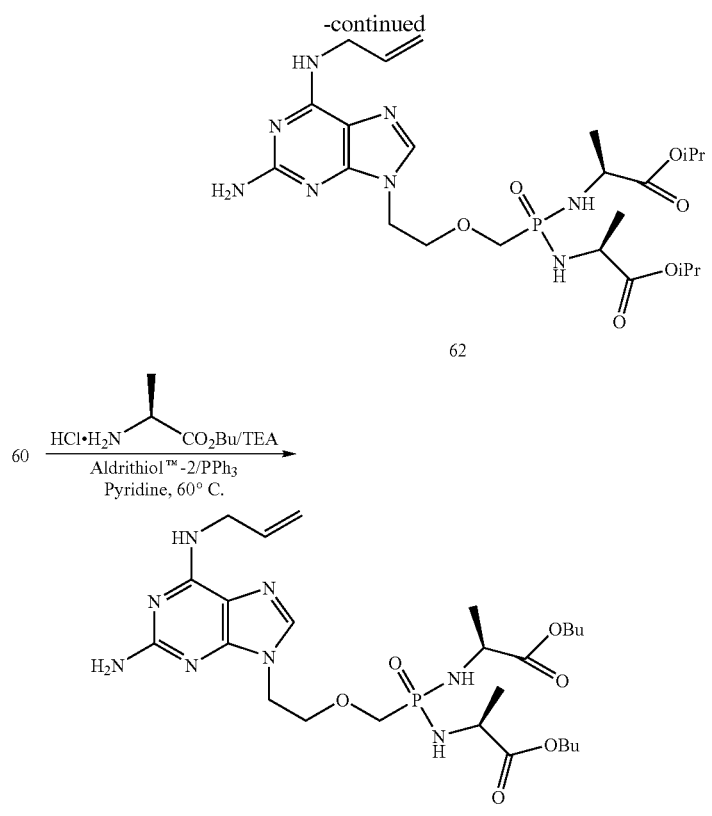
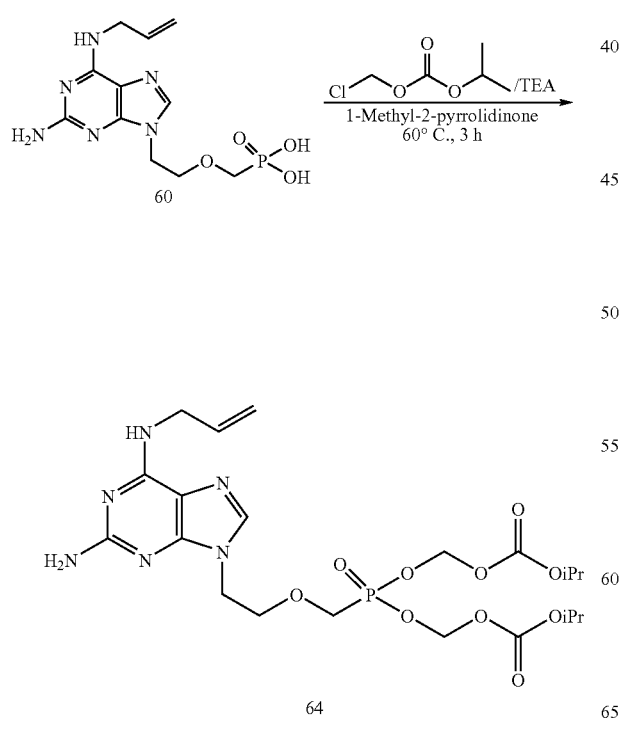
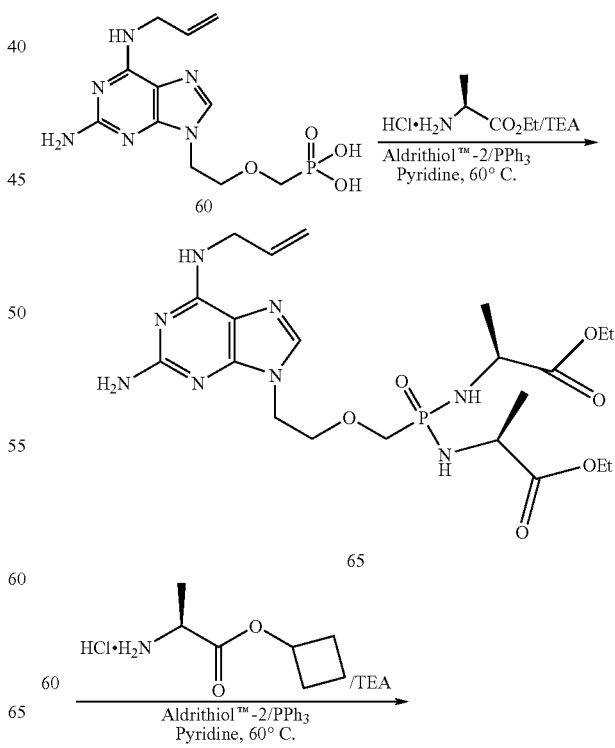

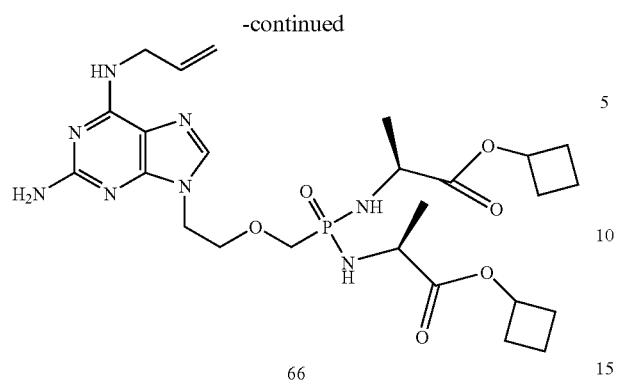
66
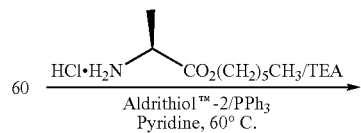
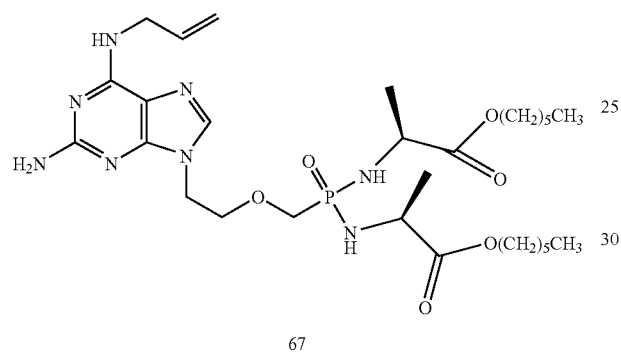
67
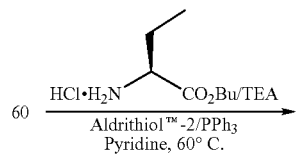
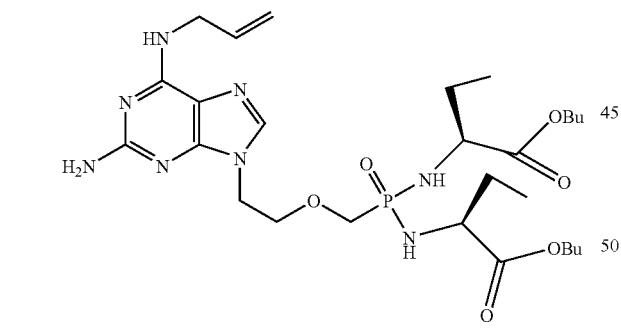
68
Scheme 19
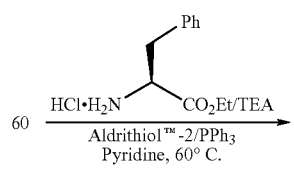
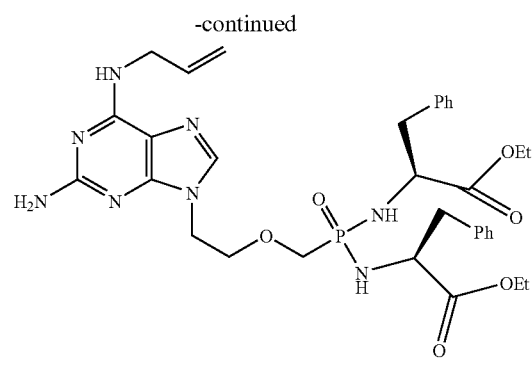
69
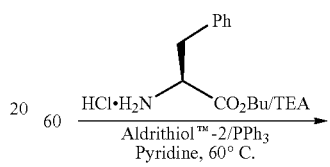
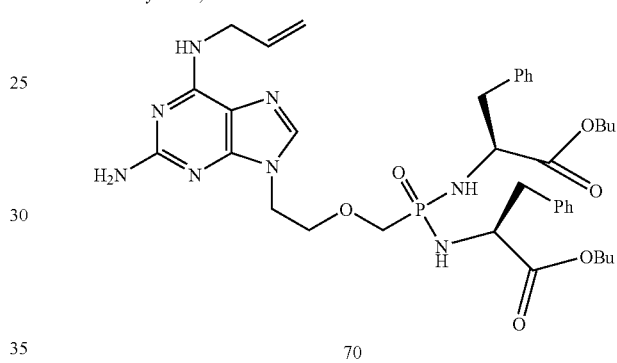
70
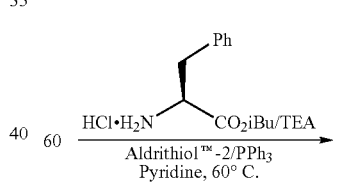
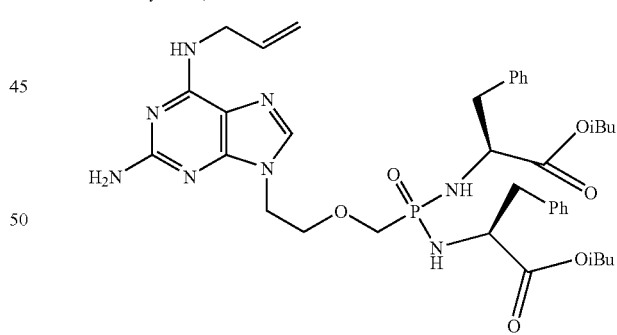
71
Scheme 20
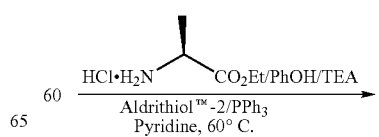

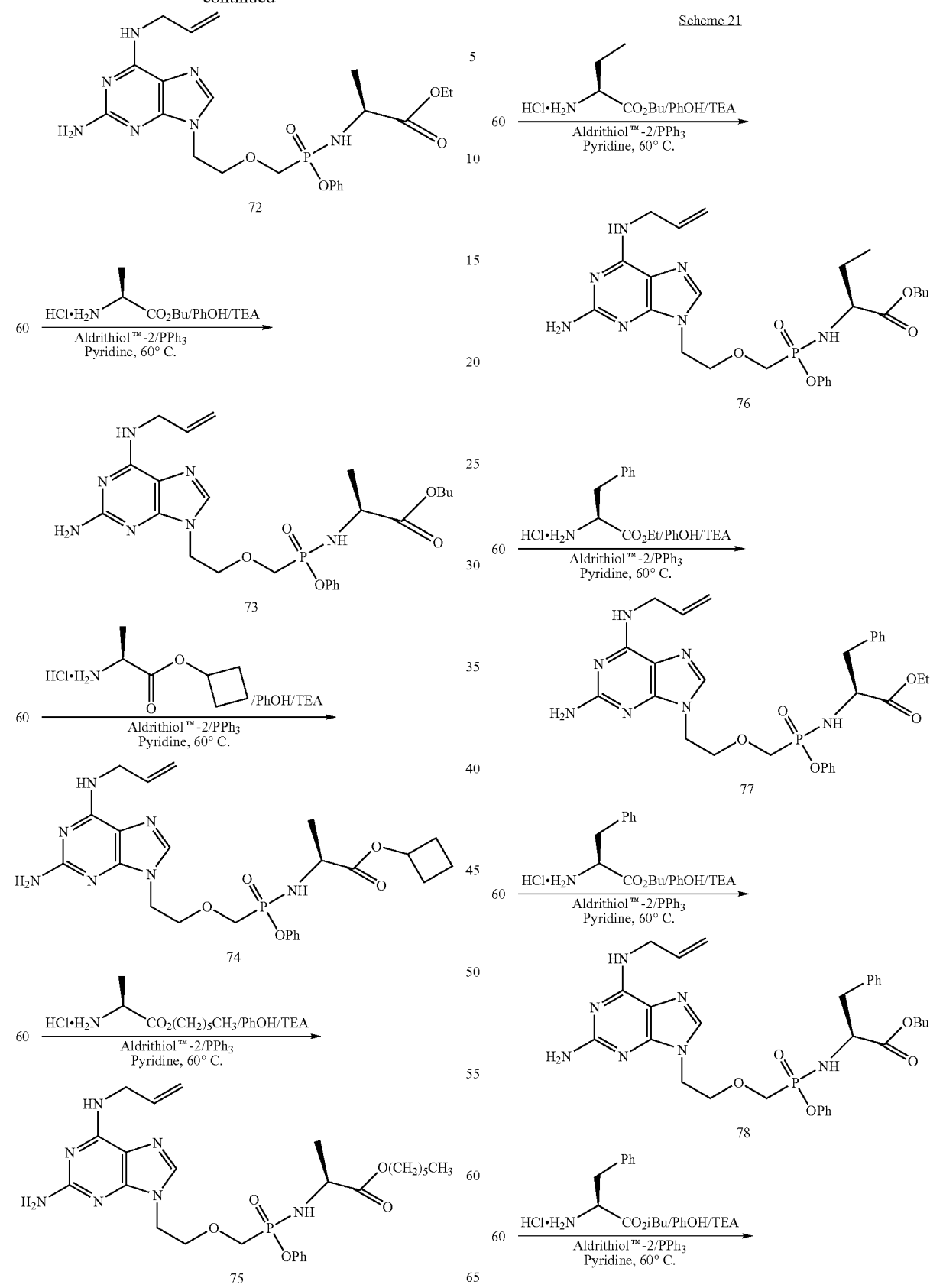

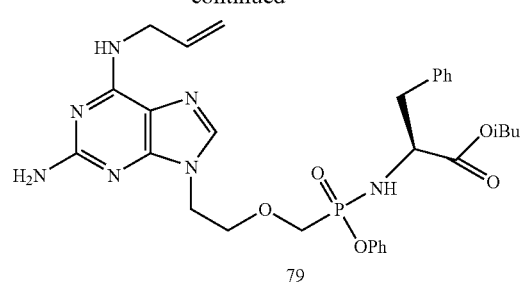
79
Scheme 22
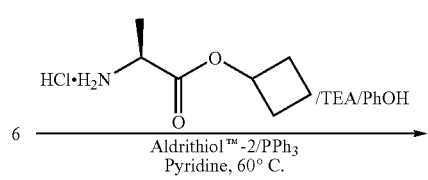
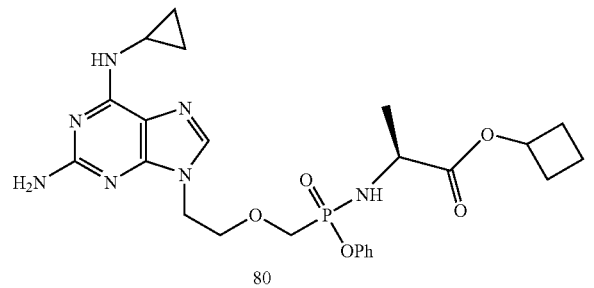
80
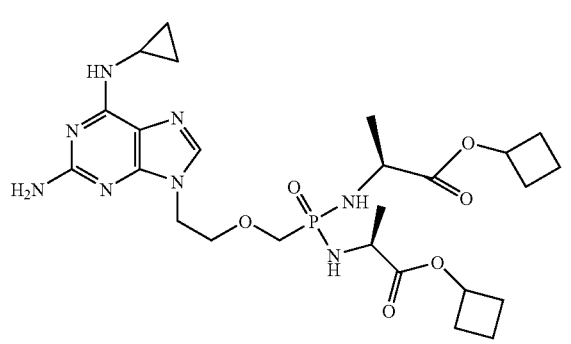
81
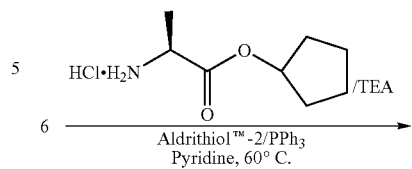
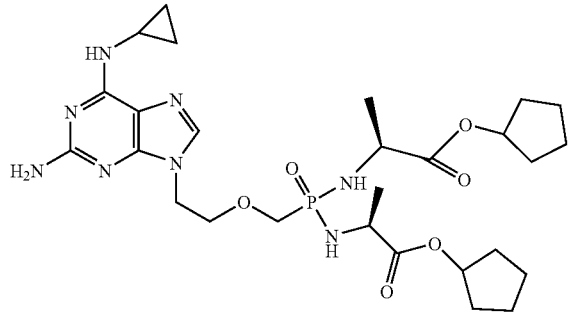
82
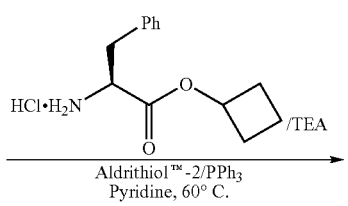
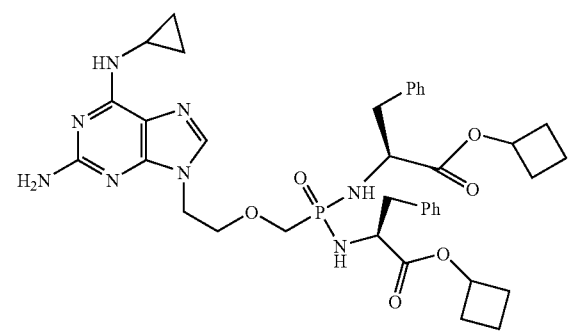
83

Scheme 23

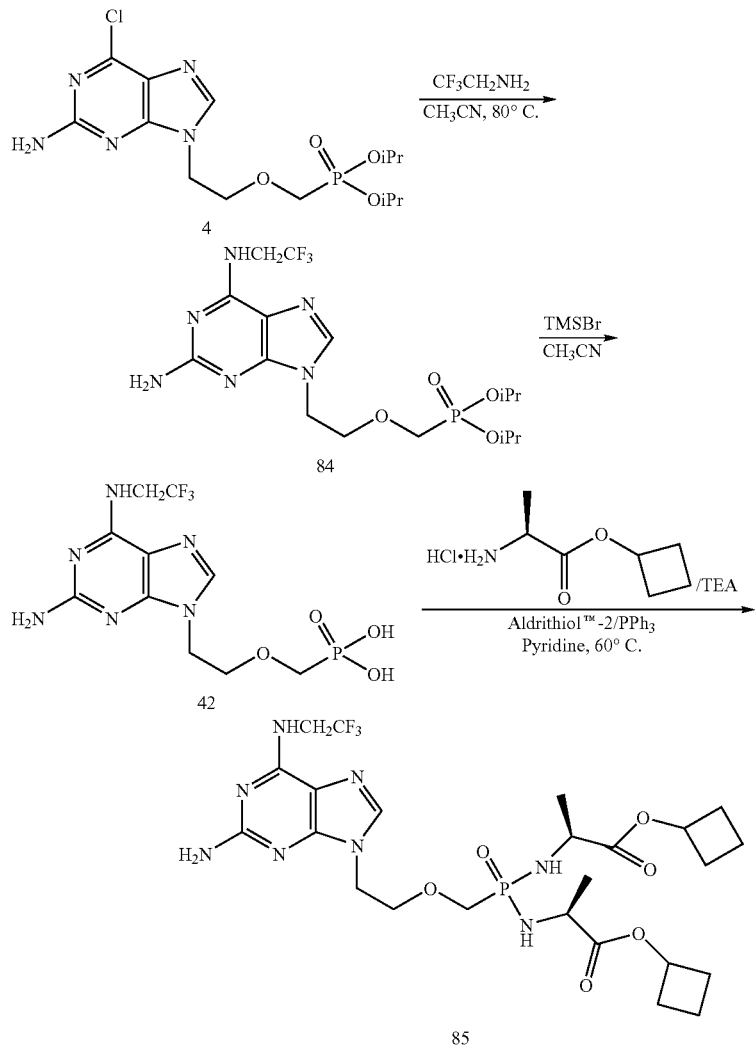

Each of the products of the following processes is optionally separated, isolated, and/or purified prior to its use in subsequent processes.

The terms "treated", "treating", "treatment", and the like, when used in the context of a chemical process, protocol, or preparation mean contacting, mixing, reacting, allowing to react, bringing into contact, and other terms common in the art for indicating that one or more chemical entities is treated in such a manner, as to convert it to one or more other chemical entities. This means that "treating compound one with compound two" is synonymous with "allowing compound one to react with compound two", "contacting compound one with compound two", "reacting compound one with compound two", and other expressions common in the art of organic synthesis for reasonably indicating that compound one was "treated", "reacted", "allowed to react", etc., with compound two.

In the context of a chemical process, protocol, or preparation, "treating" indicates the reasonable and usual manner in which organic chemicals are allowed to react. Normal concentrations (0.01M to 10M, typically 0.1M to 1M), temperatures (−100° C. to 250° C., typically −78° C. to 150° C., more typically −78° C. to 100° C., still more typically 0° C. to 100° C.), reaction vessels (typically glass, plastic, metal), solvents, pressures, atmospheres (typically air for oxygen and water insensitive reactions or nitrogen or argon for oxygen or water sensitive reactions), etc., are intended unless otherwise indicated. The knowledge of similar reactions known in the art of organic synthesis is used in selecting the conditions and apparatus for "treating" in a given process. In particular, one of ordinary skill in the art of organic synthesis selects conditions and apparatus reasonably expected to successfully carry out the chemical reactions of the described processes based on the knowledge in the art.

Modifications of each of the above scheme(s) leads to various analogs of the specific exemplary materials produced above. The above cited citations describing suitable methods of organic synthesis are applicable to such modifications.

In each of the above exemplary schemes it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example, size exclusion or ion exchange chromatography, high, medium, or low pressure liquid chromatography, small scale and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved, for example, boiling point, and molecular weight in distillation and sublimation, presence or absence of polar functional groups in chromatography, stability of materials in acidic and basic media in multiphase extraction, and the like. One skilled in the art will apply techniques most likely to achieve the desired separation.

All literature and patent citations above are hereby expressly incorporated by reference at the locations of their citation. Specifically cited sections or pages of the above cited works are incorporated by reference with specificity. The invention has been described in detail sufficient to allow one of ordinary skill in the art to make and use the subject matter of the following claims. It is apparent that certain modifications of the methods and compositions of the following claims can be made within the scope and spirit of the invention. The following Examples are provided to exemplify the present invention, and in no means can be construed to limit the present invention.

EXAMPLES

General

Some Examples have been performed multiple times. In repeated Examples, reaction conditions such as time, temperature, concentration and the like, and yields were within normal experimental ranges. In repeated Examples where significant modifications were made, these have been noted where the results varied significantly from those described. In Examples where different starting materials were used, these are noted. When the repeated Examples refer to a "corresponding" analog of a compound, such as a "corresponding ethyl ester", this intends that an otherwise present group, in this case typically a methyl ester, is taken to be the same group modified as indicated.

Examples 1 to 35 refer to Schemes 1 to 9 above.

Example 1

Acetoxyethyloxymethylchloride 1: A 5 L three-neck flask was fitted with mechanical stirrer, thermometer, 500 mL additional funnel and argon purged. 1,3-Dioxalane (140 mL, 2.00 mol) in anhydrous $Et_2O$ (800 mL) and 1.0 M $ZnCl_2/Et_2O$ (7.5 mL, 0.007 mol) were added. A solution of acetyl chloride (157 mL, 2.20 mol) in $Et_2O$ (200 mL) was added dropwise through an additional funnel over 20 min. A cold water bath was used to maintain temperature between 19-27° C. throughout. Continue stirring without external cooling for 4 h, reaction self heating at 20-25° C. for about 1 h. A clear, colorless solution retained under argon overnight. Stood for 3 days and formed an orange solution. Strip $Et_2O$ on rotavap (water aspirator) until no more distilled at 35° C. bath. A quantitative yield of product 318 g (theoretical yield 306 g) was obtained.

Example 2

Diisopropyl Phosphonate 2: A 500 mL three-neck flask was charged with the crude chloromethylether 1 (317 g, 2.00 mol). Triisopropylphosphite (494 mL) was added dropwise through an additional funnel while heating in a 125° C. oil bath and stirring vigorously. Collect 2-chloropropane distillate via short-path head in a dry ice cooled receiver, argon blanket, collected 140 g distillate (theoretical 157 g). Phosphite blanched reaction to yellow, continue heating another 2 h at 125° C. oil bath, then arrange for vacuum distillation using a vacuum pump. Distilled a yellow front cut (140 g, head to 135° C., bottom to 190° C.), then changed to clean receiver. Main fraction was collected at head temperature of 178-187° C. (mostly 185-187° C.) with vacuum unknown at bath temperature of 222-228° C. 258 g of the product 2 was given (47% yield from 1,3-dioxolane).

Example 3

Alcohol 3: A solution of 2 (125 g, 0.443 mol) in absolute MeOH (440 mL) was treated with concentrated HCl (11.2 mL, 0.112 mol) and heated to reflux for 6 h under Argon. Strip MeOH on rotavap (water aspirator) to 55° C. leaving 115 g of a clear oil which was co-evaporated with toluene (2×200 mL). The crude product was dried under vacuum to give an oil (102 g, 96%).

Example 4

Diisopropyl Phosphonate 4: A solution of triphenylphosphine (25.57 g, 97.5 mmol) and alcohol 3 (18 g, 75 mmol) in DMF (120 mL) was treated with 6-chloropurine (12.72 g, 75 mmoL) and cooled to −15° C. A solution of diisopropyl azodicarboxylate (16.68 g, 82.5 mmol) in DMF (50 mL) was added dropwise through an additional funnel over 80 min. The reaction mixture was kept at −15° C. for 2 h and then warmed to room temperature and stirred for an additional 2 h. A cloudy reaction mixture turned to be a bright yellow solution. The reaction solvent was evaporated under reduced pressure, co-evaporated with toluene (3×), and dried under vacuum overnight prior to purification. The crude product was purified by column chromatography on silica gel (5% $MeOH/CH_2Cl_2$) to give the diisopropyl phosphonate (18.52 g, 63%) as a white solid: $^1H$ NMR (CDCl3) δ 7.95 (s, 1H), 4.70 (m, 2H), 4.31 (m, 2H), 3.93 (m, 2H), 3.73 (m, 2H), 1.29 (m, 12H); $^{31}P$ NMR ($CDCl_3$) δ 18.42.

Example 5

Diisopropyl Phosphonate 5: A mixture of 4 (11.00 g, 28.08 mmol) and cyclopropylamine (4.86 g, 85.16 mmol) in $CH_3CN$ (80 mL) was placed in a reaction bomb and heated to 100° C. for 4 h. The reaction mixture was cooled to room temperature and concentrated under reduced pressure. The product was partitioned between 15% $MeOH/CH_2Cl_2$ (3×) and brine, dried with $Na_2SO_4$, filtered, and concentrated. The crude product was purified by column chromatography on silica gel (5% MeOH/CH$_2$Cl$_2$) to give 5 (10.42 g, 90%) as a pale yellow foam: $^1$H NMR (CDCl$_3$) δ 7.59 (s, 1H), 5.83 (broad, s, 1H), 4.88 (broad, s, 2H), 4.70 (m, 2H), 4.21 (m, 2H), 3.88 (m, 2H), 3.72 (d, J=8.4 Hz, 2H), 3.03 (broad s, 1H), 1.28 (m, 12H), 0.84 (m, 2H), 0.60 (m, 2H); $^{31}$P NMR (CDCl$_3$) δ 18.63.

Example 6 cPrPMEDAP 6: A solution of 5 (11.00 g, 26.67 mmol) in anhydrous CH$_3$CN (120 mL) was treated with bromotrimethylsilane (21.1 mL, 160.02 mmol). The reaction was protected from light by wrapping the flask with aluminum foil. The reaction mixture was stirred at room temperature overnight. The volatiles were evaporated under reduced pressure. The residue was dissolved in H$_2$O (250 mL) and pH was adjusted to 9 with ammonium hydroxide. The reaction mixture was concentrated and a yellow solid was obtained. The solid was dissolved in H$_2$O (30 mL) and pH was adjusted to 2 with 10% HCl. Fine solid was collected and dried under vacuum to give 6 (7.88 g, 90%) as a white solid.

Example 7

Monophosphonic Acid Hydrochloride 7: A mixture of acid 6 (3.00 g, 9.15 mmol) and DMF (0.1 mL) in sulfolane (9.2 mL) was heated to 70° C. Thionylchloride (1.66 mL, 22.76 mmol) was added dropwise over a period of 1 h. The temperature was increased to 90° C. and TMSOPh (1.74 mL, 9.61 mmol) was added and stirred for 1 h. The reaction mixture was cooled to room temperature overnight. The reaction mixture was added dropwise to well-stirred, ice-cold acetone (100 mL). The product was precipitated out. The solid was filtered under Ar, washed with cold acetone (100 mL), dried under vacuum to give the monophosphonic acid hydrochloride (3.70 g, 92%) as a solid.

Example 8

Monophosphonamidate 8: A mixture of monophosphonic acid 7 (0.22 g, 0.50 mmol), L-alanine methyl ester hydrochloride (0.14 g, 1.00 mmol), and triethylamine (0.21 mL, 1.50 mmol) in pyridine (3 mL) was heated to 60° C. for 5 min. A freshly prepared bright yellow solution of aldrithiol (0.39 g, 1.75 mmol) and triphenylphosphine (0.46 g, 1.75 mmol) in pyridine (2 mL) was added to the above reaction mixture. The reaction was stirred at 60° C. overnight, cooled to room temperature, and concentrated. The product was partitioned between EtOAc and saturated NaHCO$_3$. The organic phase was washed with brine, dried with Na$_2$SO$_4$, filtered, and evaporated under reduced pressure. The crude product was purified by column chromatography on silica gel (7% MeOH/CH$_2$Cl$_2$) to give the monophosphonamidate (97 mg, 39%, 1:1 diastereomeric mixture) as an off-white foam.

Example 9

Monophosphonamidate 9: A mixture of monophosphonic acid 7 (0.88 g, 2.00 mmol), D-alanine methyl ester hydrochloride (0.84 g, 6.00 mmol), and triethylamine (0.84 mL, 6.00 mmol) in pyridine (8 mL) was heated to 60° C. for 5 min. A freshly prepared bright yellow solution of aldrithiol (1.56 g, 7.00 mmol) and triphenylphosphine (1.84 g, 7.00 mmol) in pyridine (8 mL) was added to the above reaction mixture. The reaction was stirred at 60° C. overnight, cooled to room temperature, and concentrated. The product was partitioned between EtOAc and saturated NaHCO$_3$. The organic phase was washed with brine, dried with Na$_2$SO$_4$, filtered, and evaporated under reduced pressure. The crude product was purified by column chromatography on silica gel (7% MeOH/CH$_2$Cl$_2$) to give the monophosphonamidate (0.40 g, 41%, 1:1 diastereomeric mixture) as an off-white foam.

Example 10

Monophosphonamidate 10: A mixture of monophosphonic acid 7 (0.88 g, 2.00 mmol), L-alanine tert-butyl ester hydrochloride (1.31 g, 6.00 mmol), and triethylamine (0.84 mL, 6.00 mmol) in pyridine (8 mL) was heated to 60° C. for 5 min. A freshly prepared bright yellow solution of aldrithiol (1.54 g, 7.00 mmol) and triphenylphosphine (1.84 g, 7.00 mmol) in pyridine (8 mL) was added to the above reaction mixture. The reaction was stirred at 60° C. overnight, cooled to room temperature, and concentrated. The product was partitioned between EtOAc and saturated NaHCO$_3$. The organic phase was washed with brine, dried with Na$_2$SO$_4$, filtered, and evaporated under reduced pressure. The crude product was purified by column chromatography on silica gel (7% MeOH/CH$_2$Cl$_2$) to give the monophosphonamidate (0.38 g, 36%, 1:1 diastereomeric mixture) as a light orange foam.

Example 11

Monophosphonamidate 11: A mixture of phosphonic acid 6 (0.10 g, 0.30 mmol), L-alanine ethyl ester hydrochloride (94 mg, 0.60 mmol), phenol (0.14 g, 1.52 mmol) and triethylamine (0.51 mL, 3.60 mmol) in pyridine (1.0 mL) was heated to 60° C. for 5 min. A freshly prepared bright yellow solution of aldrithiol (0.47 g, 2.13 mmol) and triphenylphosphine (0.56 g, 2.13 mmol) in pyridine (1.0 mL) was added to the above reaction mixture. The reaction was stirred at 60° C. overnight, cooled to room temperature, and concentrated. The product was partitioned between EtOAc and saturated NaHCO$_3$. The organic phase was washed with brine, dried with Na$_2$SO$_4$, filtered, and evaporated under reduced pressure. The crude product was purified by column chromatography on silica gel (7% MeOH/CH$_2$Cl$_2$) to give the monophosphonamidate (74 mg, 48%, 1:1 diastereomeric mixture) as a pale yellow foam: $^1$H NMR (CDCl$_3$) δ 7.61 (d, J=4.2 Hz, 1H), 7.26-7.08 (m, 5H), 4.23 (m, 2H), 4.13 (m, 2H), 4.09 (m, 1H), 3.92-3.85 (m, 4H), 3.03 (broad, s, 1H), 1.30-1.26 (m, 3H), 1.24 (m, 3H), 0.88 (m, 2H), 0.63 (m, 2H); $^{31}$P NMR (CDCl$_3$) δ 21.94, 20.68.

Example 12

Monophosphonamidate 12: A mixture of phosphonic acid 6 (1.50 g, 4.56 mmol), L-alanine n-propyl ester hydrochloride (1.59 g, 9.49 mmol), phenol (2.25 g, 22.80 mmol) and triethylamine (10.50 mL, 54.72 mmol) in pyridine (8.0 mL) was heated to 60° C. for 5 min. A freshly prepared bright yellow solution of aldrithiol (6.54 g, 31.92 mmol) and triphenylphosphine (7.32 g, 31.92 mmol) in pyridine (8.0 mL) was added to the above reaction mixture. The reaction was stirred at 60° C. overnight, cooled to room temperature, and concentrated. The product was partitioned between EtOAc and saturated NaHCO$_3$. The organic phase was washed with brine, dried with Na$_2$SO$_4$, filtered, and evaporated under reduced pressure. The crude product was purified by column chromatography on silica gel (7% MeOH/CH$_2$Cl$_2$) to give the monophosphonamidate (0.43 g, 18%, Compound E, 1:1 diastereomeric mixture) as a pale yellow foam: $^1$H NMR (CDCl$_3$) δ 7.61 (d, J=5.1 Hz, 1H), 7.27-7.09 (m, 5H), 4.27-

4.20 (m, 2H), 4.16-4.00 (m, 3H), 3.93-3.82 (m, 4H), 3.04 (broad, s, 1H), 1.63 (m, 2H), 1.30 (dd, 3H), 0.92 (m, 3H), 0.89 (m, 2H), 0.63 (m, 2H); $^{31}$P NMR (CDCl$_3$) δ 21.89, 20.66.

Example 13

Monophosphonamidate 13: A mixture of phosphonic acid 6 (0.10 g, 0.30 mmol), L-alanine isopropyl ester hydrochloride (0.10 g, 0.60 mmol), phenol (0.14 g, 1.52 mmol) and triethylamine (0.51 mL, 3.60 mmol) in pyridine (1.0 mL) was heated to 60° C. for 5 min. A freshly prepared bright yellow solution of aldrithiol (0.47 g, 2.13 mmol) and triphenylphosphine (0.56 g, 2.13 mmol) in pyridine (1.0 mL) was added to the above reaction mixture. The reaction was stirred at 60° C. overnight, cooled to room temperature, and concentrated. The product was partitioned between EtOAc and saturated NaHCO$_3$. The organic phase was washed with brine, dried with Na$_2$SO$_4$, filtered, and evaporated under reduced pressure. The crude product was purified by column chromatography on silica gel (7% MeOH/CH$_2$Cl$_2$) to give the monophosphonamidate (87 mg, 55%, 1:1 diastereomeric mixture) as a yellow foam: $^1$H NMR (CDCl$_3$) δ 7.60 (d, J=2.1 Hz, 1H), 7.26-7.09 (m, 5H), 4.98 (m, 1H), 4.23 (m, 2H), 4.06 (m, 1H), 3.91-3.83 (m, 4H), 3.04 (broad, s, 1H), 1.29-1.21 (m, 9H), 0.89 (m, 2H), 0.63 (m, 2H); $^{31}$P NMR (CDCl$_3$) δ 21.85, 20.68.

Example 14

Monophosphonamidate 14: A mixture of phosphonic acid 6 (0.10 g, 0.30 mmol), L-alanine n-butyl ester hydrochloride (0.11 g, 0.60 mmol), phenol (0.14 g, 1.52 mmol) and triethylamine (0.51 mL, 3.60 mmol) in pyridine (1.0 mL) was heated to 60° C. for 5 min. A freshly prepared bright yellow solution of aldrithiol (0.47 g, 2.13 mmol) and triphenylphosphine (0.56 g, 2.13 mmol) in pyridine (1.0 mL) was added to the above reaction mixture. The reaction was stirred at 60° C. overnight, cooled to room temperature, and concentrated. The product was partitioned between EtOAc and saturated NaHCO$_3$. The organic phase was washed with brine, dried with Na$_2$SO$_4$, filtered, and evaporated under reduced pressure. The crude product was purified by column chromatography on silica gel (7% MeOH/CH$_2$Cl$_2$) to give the monophosphonamidate (80 mg, 50%, 1:1 diastereomeric mixture) as a pale yellow foam: $^1$H NMR (CDCl$_3$) δ 7.61 (d, J=4.20 Hz, 1H), 7.27-7.08 (m, 5H); 5.93 (broad, s, 2H), 4.23 (m, 2H), 4.10-4.08 (m, 3H), 3.91-3.84 (m, 4H), 3.03 (broad, s, 1H), 1.58 (m, 2H), 1.34-1.27 (m, 5H), 0.92-0.89 (m, 5H), 0.63 (m, 2H); $^{31}$P NMR (CDCl$_3$) δ 21.94, 20.68.

Example 15

Monophosphonamidate 15: A mixture of phosphonic acid 6 (0.10 g, 0.30 mmol), L-alanine n-hexyl ester hydrochloride (0.13 g, 0.60 mmol), phenol (0.14 g, 1.52 mmol) and triethylamine (0.51 mL, 3.60 mmol) in pyridine (1.0 mL) was heated to 60° C. for 5 min. A freshly prepared bright yellow solution of aldrithiol (0.47 g, 2.13 mmol) and triphenylphosphine (0.56 g, 2.13 mmol) in pyridine (1.0 mL) was added to the above reaction mixture. The reaction was stirred at 60° C. overnight, cooled to room temperature, and concentrated. The product was partitioned between EtOAc and saturated NaHCO$_3$. The organic phase was washed with brine, dried with Na$_2$SO$_4$, filtered, and evaporated under reduced pressure. The crude product was purified by chromatography on ISCO (2-propanol/CH$_2$Cl$_2$) to give the monophosphonamidate (0.10 g, 59%, 1:1 diastereomeric mixture) as a pale yellow foam: $^1$H NMR (CDCl$_3$) δ 7.59 (d, J=4.20 Hz, 1H), 7.26-7.08 (m, 5H), 4.22 (m, 2H), 4.11 (m, 1H), 4.06 (m, 2H), 3.91-3.84 (m, 4H), 3.01 (broad, s, 1H), 1.59 (m, 2H), 1.31-1.27 (m, 9H), 0.89 (m, 3H), 0.86 (m, 2H), 0.62 (m, 2H); $^{31}$P NMR (CDCl$_3$) δ 21.94, 20.68.

Example 16

Monophosphonamidate 16: A mixture of phosphonic acid 6 (0.10 g, 0.30 mmol), L-alanine n-octanyl ester hydrochloride (0.15 g, 0.60 mmol), phenol (0.14 g, 1.52 mmol) and triethylamine (0.51 mL, 3.60 mmol) in pyridine (1.0 mL) was heated to 60° C. for 5 min. A freshly prepared bright yellow solution of aldrithiol (0.47 g, 2.13 mmol) and triphenylphosphine (0.56 g, 2.13 mmol) in pyridine (1.0 mL) was added to the above reaction mixture. The reaction was stirred at 60° C. overnight, cooled to room temperature, and concentrated. The product was partitioned between EtOAc and saturated NaHCO$_3$. The organic phase was washed with brine, dried with Na$_2$SO$_4$, filtered, and evaporated under reduced pressure. The crude product was purified by chromatography on ISCO (2-propanol/CH$_2$Cl$_2$) to give the monophosphonamidate (0.13 g, 73%, 1:1 diastereomeric mixture) as a pale yellow foam: $^1$H NMR (CDCl$_3$) δ 7.59 (d, J=4.2 Hz, 1H), 7.25-7.07 (m, 5H), 4.22 (m, 2H), 4.10 (m, 1H), 4.07 (m, 2H), 3.90-3.84 (m, 4H), 3.02 (broad, s, 1H), 1.59 (m, 2H), 1.29-1.26 (m, 13H), 0.88 (m, 3H), 0.85 (m, 2H), 0.60 (m, 2H); $^{31}$P NMR (CDCl$_3$) δ 21.96, 20.69.

Example 17

Monophosphonamidate 17: A mixture of phosphonic acid 6 (70 mg, 0.21 mmol), L-2-aminobutyric acid ethyl ester hydrochloride (72 mg, 0.42 mmol), phenol (0.10 g, 1.05 mmol) and triethylamine (0.36 mL, 2.52 mmol) in pyridine (1.0 mL) was heated to 60° C. for 5 min. A freshly prepared bright yellow solution of aldrithiol (0.33 g, 1.47 mmol) and triphenylphosphine (0.39 g, 1.47 mmol) in pyridine (1.0 mL) was added to the above reaction mixture. The reaction was stirred at 60° C. overnight, cooled to room temperature, and concentrated. The product was partitioned between EtOAc and saturated NaHCO$_3$. The organic phase was washed with brine, dried with Na$_2$SO$_4$, filtered, and evaporated under reduced pressure. The crude product was purified by column chromatography on silica gel (7% MeOH/CH$_2$Cl$_2$) to give the monophosphonamidate (66 mg, 60%, 1:1 diastereomeric mixture) as a pale yellow foam: $^1$H NMR (CDCl$_3$) δ 7.61 (d, J=7.2 Hz, 1H), 7.26-7.08 (m, 5H), 5.91 (broad, s, 1H), 4.97 (broad, s, 2H), 4.22-4.12 (m, 4H), 4.01-3.81 (m, 5H), 3.03 (broad, s, 1H), 1.71-1.60 (m, 2H), 1.24 (m, 3H), 0.89 (m, 2H), 0.84-0.76 (m, 3H), 0.63 (m, 2H); $^{31}$P NMR (CDCl$_3$) δ 22.15, 20.93.

Example 18

Monophosphonamidate 18: A mixture of phosphonic acid 6 (1.00 g, 3.05 mmol), L-2-aminobutyric acid n-butyl ester hydrochloride (1.19 g, 6.09 mmol), phenol (1.43 g, 15.23 mmol) and triethylamine (5.10 mL, 36.60 mmol) in pyridine (5.0 mL) was heated to 60° C. for 5 min. A freshly prepared bright yellow solution of aldrithiol (4.70 g, 21.32 mmol) and triphenylphosphine (5.59 g, 21.32 mmol) in pyridine (5.0 mL) was added to the above reaction mixture. The reaction was stirred at 60° C. overnight, cooled to room temperature, and concentrated. The product was partitioned between EtOAc and saturated NaHCO$_3$. The organic phase was washed with brine, dried with Na$_2$SO$_4$, filtered, and evaporated under reduced pressure. The crude product was purified by column chromatography on silica gel (5% MeOH/CH$_2$Cl$_2$) to give the monophosphonamide (0.7 g, 42%, Compound G, 1:1 diastereomeric mixture) as an off-white foam: $^1$H NMR (CDCl$_3$) δ 7.60 (d, J=6.60 Hz, 1H), 7.27-7.04 (m, 5H), 5.89 (broad, s, 1H), 4.94 (broad, s, 2H), 4.22 (m, 2H), 4.07-3.99 (m, 3H), 3.91-3.84 (m, 4H), 3.03 (broad, s, 1H), 1.70-1.57 (m, 4H), 1.35 (m, 2H), 0.92-0.75 (m, 8H), 0.63 (m, 2H); $^{31}$P NMR (CDCl$_3$) δ 22.21, 20.95.

Example 19

Monophosphonamidate 19: A mixture of phosphonic acid 6 (0.10 g, 0.30 mmol), L-2-aminobutyric acid n-octanyl ester hydrochloride (0.15 g, 0.60 mmol), phenol (0.14 g, 1.52 mmol) and triethylamine (0.51 mL, 3.60 mmol) in pyridine (1.0 mL) was heated to 60° C. for 5 min. A freshly prepared bright yellow solution of aldrithiol (0.47 g, 2.13 mmol) and triphenylphosphine (0.56 g, 2.13 mmol) in pyridine (1.0 mL) was added to the above reaction mixture. The reaction was stirred at 60° C. overnight, cooled to room temperature, and concentrated. The product was partitioned between EtOAc and saturated NaHCO$_3$. The organic phase was washed with brine, dried with Na$_2$SO$_4$, filtered, and evaporated under reduced pressure. The crude product was purified by chromatography on ISCO (2-propanol /CH$_2$Cl$_2$) to give the monophosphonamidate (0.12 g, 64%, 1:1 diastereomeric mixture) as a pale yellow foam: $^1$H NMR (CDCl$_3$) δ 7.62 (d, J=6.60 Hz, 1H), 7.25-7.08 (m, 5H), 4.24-4.21 (m 2H), 4.09-4.04 (m, 2H), 4.00 (m, 1H), 3.91-3.83 (m, 4H), 3.01 (broad, s, 1H), 1.70-1.58 (m, 4H), 1.27 (m, 10H), 0.89-0.76 (m, 8H), 0.62 (m, 2H); $^{31}$P NMR (CDCl$_3$) δ 22.22, 20.92.

Example 20

Monophosphonamidate 20: A mixture of phosphonic acid 6 (1.5 g, 4.57 mmol), L-phenylalanine ethyl ester hydrochloride (2.10 g, 9.14 mmol), phenol (2.15 g, 22.85 mmol) and triethylamine (7.64 mL, 54.84 mmol) in pyridine (8.0 mL) was heated to 60° C. for 5 min. A freshly prepared bright yellow solution of aldrithiol (7.05 g, 31.99 mmol) and triphenylphosphine (8.39 g, 31.99 mmol) in pyridine (7.0 mL) was added to the above reaction mixture. The reaction was stirred at 60° C. overnight, cooled to room temperature, and concentrated. The product was partitioned between EtOAc and saturated NaHCO$_3$. The organic phase was washed with brine, dried with Na$_2$SO$_4$, filtered, and evaporated under reduced pressure. The crude product was purified by column chromatography on silica gel (5% MeOH/CH$_2$Cl$_2$) to give a pale yellow solid 1.32 g containing about 10% impurity. The yellow solid (1.32 g, 2.28 mmol) was dissolved in iPrOH (10 mL) and transferred to a hot iPrOH (30 mL) solution of fumaric acid (0.27 g, 2.28 mmol) and stirred at 80° C. for 30 min. The reaction mixture was gradually cooled to room temperature and the fumarate salt was collected at 0° C. The resulting fumarate salt was neutralized by partition from NaHCO$_3$ (2×) and EtOAc. The organic phase was washed with brine, H$_2$O, dried with Na$_2$SO$_4$, filtered, and concentrated. The product was dried under vacuum to give the monophosphonamidate (0.70 g, 26%, Compound A, 1:1 diastereomeric mixture) as a white foam: $^1$H NMR (CDCl$_3$) δ 7.54 (d, J=2.4 Hz, 1H), 7.27-6.98 (m, 10H), 4.35 (m, 1H), 4.16 (m, 2H), 4.08 (m, 2H), 3.84-3.61 (m, 3H), 3.33 (m, 1H), 3.02 (broad, s, 1H), 2.95-2.87 (m, 2H), 1.17 (m, 3H), 0.87 (m, 2H), 0.61 (m, 2H); $^{31}$P NMR (CDCl$_3$) δ 21.88, 21.07.

Example 21

Monophosphonamidate 21: A mixture of phosphonic acid 6 (70 mg, 0.21 mmol), L-phenylalanine n-butyl ester hydrochloride (0.11 g, 0.42 mmol), phenol (0.10 g, 1.05 mmol) and triethylamine (0.36 mL, 2.52 mmol) in pyridine (1.0 mL) was heated to 60° C. for 5 min. A freshly prepared bright yellow solution of aldrithiol (0.33 g, 1.47 mmol) and triphenylphosphine (0.39 g, 1.47 mmol) in pyridine (1.0 mL) was added to the above reaction mixture. The reaction was stirred at 60° C. overnight, cooled to room temperature, and concentrated. The product was partitioned between EtOAc and saturated NaHCO$_3$. The organic phase was washed with brine, dried with Na$_2$SO$_4$, filtered, and evaporated under reduced pressure. The crude product was purified by column chromatography on silica gel (7% MeOH/CH$_2$Cl$_2$) to give the monophosphonamidate (30 mg, 23%, 1:1 diastereomeric mixture) as a pale yellow foam: $^1$H NMR (CDCl$_3$) δ 7.55 (d, J=2.7 Hz, 1H), 7.25-6.98 (m, 10H), 4.36 (m, 1H), 4.17 (m, 2H), 4.02 (m, 2H), 3.83-3.35 (m, 4H), 3.02 (broad, s, 1H), 2.94-2.86 (m, 2H), 1.52 (m, 2H), 1.29 (m, 2H), 0.90 (m, 3H), 0.88 (m, 2H), 0.62 (m, 2H); $^{31}$P NMR (CDCl$_3$) δ 21.85, 21.05.

Example 22

Monophosphonamidate 22: A mixture of phosphonic acid 6 (70 mg, 0.21 mmol), L-phenylalanine isobutyl ester hydrochloride (0.11 g, 0.42 mmol), phenol (0.10 g, 1.05 mmol) and triethylamine (0.36 mL, 2.52 mmol) in pyridine (1.0 mL) was heated to 60° C. for 5 min. A freshly prepared bright yellow solution of aldrithiol (0.33 g, 1.47 mmol) and triphenylphosphine (0.39 g, 1.47 mmol) in pyridine (1.0 mL) was added to the above reaction mixture. The reaction was stirred at 60° C. overnight, cooled to room temperature, and concentrated. The product was partitioned between EtOAc and saturated NaHCO$_3$. The organic phase was washed with brine, dried with Na$_2$SO$_4$, filtered, and evaporated under reduced pressure. The crude product was purified by column chromatography on silica gel (7% MeOH/CH$_2$Cl$_2$) to give the monophosphonamidate (65 mg, 50%, 1:1 diastereomeric mixture) as a pale yellow foam: $^1$H NMR (CDCl$_3$) δ 7.56 (d, J=3.6 Hz, 1H), 7.26-6.98 (m, 10H), 4.40 (m, 1H), 4.17 (m, 2H), 3.82 (m, 2H), 3.75-3.62 (m, 3H), 3.35 (m, 1H), 3.04 (broad, s, 1H), 2.96-2.87 (m, 2H), 1.83 (m, 1H), 0.90 (m, 2H), 0.86 (m, 6H), 0.63 (m, 2H); $^{31}$P NMR (CDCl$_3$) δ 21.82, 21.03.

Example 23

Bisphosphonamidate 23: A mixture of phosphonic acid 6 (0.10 g, 0.30 mmol), L-alanine ethyl ester hydrochloride (0.28 g, 1.80 mmol), and triethylamine (0.51 mL, 3.60 mmol) in pyridine (1.0 mL) was heated to 60° C. for 5 min. A freshly prepared bright yellow solution of aldrithiol (0.47 g, 2.10 mmol) and triphenylphosphine (0.56 g, 2.10 mmol) in pyridine (1.0 mL) was added to the above reaction mixture. The reaction was stirred at 60° C. overnight, cooled to room temperature, and concentrated. The product was partitioned between EtOAc and saturated NaHCO$_3$. The organic phase was washed with brine, dried with Na$_2$SO$_4$, filtered, and evaporated under reduced pressure. The crude product was purified by column chromatography on silica gel (10% MeOH/CH$_2$Cl$_2$) to give the bisphosphonamidate (80 mg, 50%,) as a pale yellow foam: $^1$H NMR (CDCl$_3$) δ 7.63 (s, 1H), 5.88 (broad, s, 1H), 4.96 (broad, s, 2H), 4.24-4.16 (m, 6H), 4.00 (m, 2H), 3.86 (m, 2H), 3.72 (m, 2H), 3.01 (broad, s, 1H), 1.36 (m, 6H), 1.26 (m, 6H), 0.86 (m, 2H), 0.61 (m, 2H); $^{31}$P NMR (CDCl$_3$) δ 20.63.

Example 24

Bisphosphonamidate 24: A mixture of phosphonic acid 6 (1.00 g, 3.05 mmol), L-alanine n-propyl ester hydrochloride (3.06 g, 18.30 mmol), and triethylamine (5.10 mL, 36.50 mmol) in pyridine (5.0 mL) was heated to 60° C. for 5 min. A freshly prepared bright yellow solution of aldrithiol (4.70 g, 21.32 mmol) and triphenylphosphine (5.59 g, 21.32 mmol) in pyridine (5.0 mL) was added to the above reaction mixture. The reaction was stirred at 60° C. overnight, cooled to room temperature, and concentrated. The product was partitioned between EtOAc and saturated NaHCO$_3$. The organic phase was washed with brine, dried with Na$_2$SO$_4$, filtered, and evaporated under reduced pressure. The crude product was purified by column chromatography on silica gel (10% MeOH/CH$_2$Cl$_2$) to give the bisphosphonamidate (1.13 g, 71%, Compound F) as a pale yellow foam: $^1$H NMR (CDCl$_3$) δ 7.65 (s, 1H), 5.92 (broad, s, 1H), 5.03 (broad, s, 2H), 4.24 (m, 2H), 4.10-4.02 (m, 6H), 3.87 (m, 2H), 3.73 (m, 2H), 3.03 (broad, s, 1H), 1.65 (m, 4H), 1.37 (m, 6H), 0.93 (m, 6H), 0.88 (m, 2H), 0.63 (m, 2H); $^{31}$P NMR (CDCl$_3$) δ 20.61.

Example 25

Bisphosphonamidate 25: A mixture of phosphonic acid 6 (0.60 g, 1.83 mmol), L-alanine isopropyl ester hydrochloride (1.84 g, 10.98 mmol), and triethylamine (3.06 mL, 21.96 mmol) in pyridine (3.0 mL) was heated to 60° C. for 5 min. A freshly prepared bright yellow solution of aldrithiol (2.82 g, 12.80 mmol) and triphenylphosphine (3.36 g, 12.80 mmol) in pyridine (3.0 mL) was added to the above reaction mixture. The reaction was stirred at 60° C. overnight, cooled to room temperature, and concentrated. The product was partitioned between EtOAc and saturated NaHCO$_3$. The organic phase was washed with brine, dried with Na$_2$SO$_4$, filtered, and evaporated under reduced pressure. The crude product was purified by column chromatography on silica gel (10% MeOH/CH$_2$Cl$_2$) to give the bisphosphonamidate (0.53 g, 52%, Compound B) as a pale yellow foam: $^1$H NMR (CDCl$_3$) δ 7.65 (s, 1H), 5.00 (m, 2H), 4.24 (m, 2H), 3.97 (m, 2H), 3.87 (m, 2H), 3.71 (m, 2H), 3.01 (broad, s, 1H), 1.34 (m, 6H), 1.23 (m, 12H), 0.86 (m, 2H), 0.62 (m, 2H); $^{31}$P NMR (CDCl$_3$) δ 20.59.

Example 26

Bisphosphonamidate 26: A mixture of phosphonic acid 6 (0.10 g, 0.30 mmol), L-alanine n-butyl ester hydrochloride (0.33 g, 1.82 mmol), and triethylamine (0.51 mL, 3.60 mmol) in pyridine (1.0 mL) was heated to 60° C. for 5 min. A freshly prepared bright yellow solution of aldrithiol (0.47 g, 2.10 mmol) and triphenylphosphine (0.56 g, 2.10 mmol) in pyridine (1.0 mL) was added to the above reaction mixture. The reaction was stirred at 60° C. overnight, cooled to room temperature, and concentrated. The product was partitioned between EtOAc and saturated NaHCO$_3$. The organic phase was washed with brine, dried with Na$_2$SO$_4$, filtered, and evaporated under reduced pressure. The crude product was purified by column chromatography on silica gel (10% MeOH/CH$_2$Cl$_2$) to give the bisphosphonamidate (97 mg, 55%) as a pale yellow foam: $^1$H NMR (CDCl$_3$) δ 7.63 (s, 1H), 4.24 (m, 2H), 4.09 (m, 4H), 4.01 (m, 2H), 3.86 (m, 2H), 3.72 (m, 2H), 3.01 (broad, s, 1H), 1.61 (m, 4H), 1.37 (m, 10H), 0.93 (m, 6H), 0.88 (m, 2H), 0.61 (m, 2H); $^{31}$P NMR (CDCl$_3$) δ 20.59.

Example 27

Bisphosphonamidate 27: A mixture of phosphonic acid 6 (0.10 g, 0.30 mmol), L-alanine n-hexyl ester hydrochloride (0.38 g, 1.80 mmol), and triethylamine (0.51 mL, 3.60 mmol) in pyridine (1.0 mL) was heated to 60° C. for 5 min. A freshly prepared bright yellow solution of aldrithiol (0.47 g, 2.10 mmol) and triphenylphosphine (0.56 g, 2.10 mmol) in pyridine (1.0 mL) was added to the above reaction mixture. The reaction was stirred at 60° C. overnight, cooled to room temperature, and concentrated. The product was partitioned between EtOAc and saturated NaHCO$_3$. The organic phase was washed with brine, dried with Na$_2$SO$_4$, filtered, and evaporated under reduced pressure. The crude product was purified by chromatography on ISCO (2-propanol/CH$_2$Cl$_2$) to give the bisphosphonamidate (0.13 g, 65%) as a pale yellow foam: $^1$H NMR (CDCl$_3$) δ 7.62 (s, 1H), 4.23 (m, 2H), 4.09 (m, 4H), 4.01 (m, 2H), 3.86 (m, 2H), 3.72 (m, 2H), 2.99 (broad, s, 1H), 1.61 (m, 4H), 1.36-1.29 (m, 18H), 0.88 (m, 6H), 0.84 (m, 2H), 0.60 (m, 2H); $^{31}$P NMR (CDCl$_3$) δ 20.61.

Example 28

Bisphosphonamidate 28: A mixture of phosphonic acid 6 (0.10 g, 0.30 mmol), L-alanine n-octanyl ester hydrochloride (0.43 g, 1.80 mmol), and triethylamine (0.51 mL, 3.60 mmol) in pyridine (1.0 mL) was heated to 60° C. for 5 min. A freshly prepared bright yellow solution of aldrithiol (0.47 g, 2.10 mmol) and triphenylphosphine (0.56 g, 2.10 mmol) in pyridine (1.0 mL) was added to the above reaction mixture. The reaction was stirred at 60° C. overnight, cooled to room temperature, and concentrated. The product was partitioned between EtOAc and saturated NaHCO$_3$. The organic phase was washed with brine, dried with Na$_2$SO$_4$, filtered, and evaporated under reduced pressure. The crude product was purified by chromatography on ISCO (2-propanol/CH$_2$Cl$_2$) to give the bisphosphonamidate (0.13 g, 61%) as a pale yellow foam: $^1$H NMR (CDCl$_3$) δ 7.61 (s, 1H), 4.21 (m, 2H), 4.07-4.00 (m, 6H), 3.84-3.70 (m, 4H), 2.98 (broad, s, 1H), 1.60 (m, 4H), 1.34 (m, 6H), 1.27 (m, 20H), 0.87 (m, 6H), 0.83 (m, 2H), 0.58 (m, 2H); $^{31}$P NMR (CDCl$_3$) δ 20.63.

Example 29

Bisphosphonamidate 29: A mixture of phosphonic acid 6 (0.70 g, 2.13 mmol), L-2-aminobutyric acid ethyl ester hydrochloride (2.15 g, 12.80 mmol), and triethylamine (3.57 mL, 25.56 mmol) in pyridine (3.0 mL) was heated to 60° C. for 5 min. A freshly prepared bright yellow solution of aldrithiol (3.29 g, 14.91 mmol) and triphenylphosphine (3.92 g, 14.91 mmol) in pyridine (3.0 mL) was added to the above reaction mixture. The reaction was stirred at 60° C. overnight, cooled to room temperature, and concentrated. The product was partitioned between EtOAc and saturated NaHCO$_3$. The organic phase was washed with brine, dried with Na$_2$SO$_4$, filtered, and evaporated under reduced pressure. The crude product was purified by column chromatography on silica gel (10% MeOH/CH$_2$Cl$_2$) to give the bisphosphonamidate (0.71 g, 60%, Compound D) as a pale yellow foam: $^1$H NMR (CDCl$_3$) δ 7.64 (s, 1H), 4.24 (m, 2H), 4.16 (m, 4H), 3.89-3.87 (m, 4H), 3.72 (d, J=9.0 Hz, 2H), 3.01 (broad, s, 1H), 1.78-1.64 (m, 4H), 1.26 (m, 6H), 0.91 (m, 6H), 0.87 (m, 2H), 0.61 (m, 2H); $^{31}$P NMR (CDCl$_3$) δ 21.23.

Example 30

Bisphosphonamidate 30: A mixture of phosphonic acid 6 (0.70 g, 21.32 mmol), L-2-aminobutyric acid n-butyl ester hydrochloride (2.50 g, 12.80 mmol), and triethylamine (3.57 mL, 25.56 mmol) in pyridine (3.0 mL) was heated to 60° C. for 5 min. A freshly prepared bright yellow solution of aldrithiol (3.29 g, 14.91 mmol) and triphenylphosphine (3.92 g, 14.91 mmol) in pyridine (3.0 mL) was added to the above reaction mixture. The reaction was stirred at 60° C. overnight, cooled to room temperature, and concentrated. The product was partitioned between EtOAc and saturated NaHCO$_3$. The organic phase was washed with brine, dried with Na$_2$SO$_4$, filtered, and evaporated under reduced pressure. The crude product was purified by column chromatography on silica gel (10% MeOH/CH$_2$Cl$_2$) to give the bisphosphonamidate (0.40 g, 31%, Compound C) as a pale yellow foam: $^1$H NMR (CDCl$_3$) δ 7.64 (s, 1H), 4.24 (m, 2H), 4.11 (m, 4H), 3.91 (m, 2H), 3.87 (m, 2H), 3.71 (d, J=9.0 Hz, 2H), 3.03 (broad, s, 1H), 1.79-1.64 (m, 4H), 1.60 (m, 4H), 1.37 (m, 4H), 0.94 (m, 6H), 0.90 (m, 6H), 0.86 (m, 2H), 0.62 (m, 2H); $^{32}$P NMR (CDCl$_3$) δ 21.25.

Example 31

Bisphosphonamidate 31: A mixture of phosphonic acid 6 (0.10 g, 0.30 mmol), L-2-aminobutyric acid n-octanyl ester hydrochloride (0.33 g, 1.82 mmol), and triethylamine (0.51 mL, 3.60 mmol) in pyridine (1.0 mL) was heated to 60° C. for 5 min. A freshly prepared bright yellow solution of aldrithiol (0.47 g, 2.10 mmol) and triphenylphosphine (0.56 g, 2.10 mmol) in pyridine (1.0 mL) was added to the above reaction mixture. The reaction was stirred at 60° C. overnight, cooled to room temperature, and concentrated. The product was partitioned between EtOAc and saturated NaHCO$_3$. The organic phase was washed with brine, dried with Na$_2$SO$_4$, filtered, and evaporated under reduced pressure. The crude product was purified by chromatography on ISCO (2-propanol/CH$_2$Cl$_2$) to give the bisphosphonamidate (0.12 g, 55%) as a pale yellow foam: $^1$H NMR (CDCl$_3$) δ 7.64 (s, 1H), 4.24 (m, 2H), 4.13-4.05 (m, 4H), 3.91 (m, 2H), 3.87-3.72 (m, 4H), 3.01 (broad, s, 1H), 1.78-1.65 (m, 4H), 1.61-1.29 (m, 24H), 0.91 (m, 6H), 0.89 (m, 6H), 0.86 (m, 2H), 0.62 (m, 2H); $^{31}$P NMR (CDCl$_3$) δ 21.20.

Example 32

Bisphosphonamidate 32: A mixture of phosphonic acid 6 (0.60 g, 1.82 mmol), L-phenylalanine ethyl ester hydrochloride (2.51 g, 10.96 mmol), and triethylamine (3.06 mL, 21.84 mmol) in pyridine (3.0 mL) was heated to 60° C. for 5 min. A freshly prepared bright yellow solution of aldrithiol (2.82 g, 12.74 mmol) and triphenylphosphine (3.36 g, 12.74 mmol) in pyridine (3.0 mL) was added to the above reaction mixture. The reaction was stirred at 60° C. overnight, cooled to room temperature, and concentrated. The product was partitioned between EtOAc and saturated NaHCO$_3$. The organic phase was washed with brine, dried with Na$_2$SO$_4$, filtered, and evaporated under reduced pressure. The crude product was purified by chromatography on ISCO (2-propanol/CH$_2$Cl$_2$) to give the bisphosphonamidate (0.53 g, 43%) as a pale yellow foam: $^1$H NMR (CDCl$_3$) δ 7.48 (s, 1H), 7.22-7.06 (m, 10H), 4.20 (m, 1H), 4.12 (m, 4H), 4.09 (m, 2H), 4.04 (m, 1H), 3.63 (m, 2H), 3.33-3.21 (m, 2H), 3.04-2.78 (m, 5H), 1.20 (m, 6H), 0.83 (m, 2H), 0.58 (m, 2H); $^{31}$P NMR (CDCl$_3$) δ 20.38.

Example 33

Bisphosphonamidate 33: A mixture of phosphonic acid 6 (70 mg, 0.21 mmol), L-phenylalanine n-butyl ester hydrochloride (0.33 g, 1.26 mmol), and triethylamine (0.36 mL, 2.52 mmol) in pyridine (1.0 mL) was heated to 60° C. for 5 min. A freshly prepared bright yellow solution of aldrithiol (0.33 g, 1.47 mmol) and triphenylphosphine (0.39 g, 1.47 mmol) in pyridine (1.0 mL) was added to the above reaction mixture. The reaction was stirred at 60° C. overnight, cooled to room temperature, and concentrated. The product was partitioned between EtOAc and saturated NaHCO$_3$. The organic phase was washed with brine, dried with Na$_2$SO$_4$, filtered, and evaporated under reduced pressure. The crude product was purified by column chromatography on silica gel (10% MeOH/CH$_2$Cl$_2$) to give the bisphosphonamidate (0.11 g, 70%) as a pale yellow foam: $^1$H NMR (CDCl$_3$) δ 7.51 (s, 1H), 7.23-7.06 (m, 10H), 4.23 (m, 1H), 4.11-4.05 (m, 7H), 3.65 (m, 2H), 3.35-3.23 (m, 2H), 3.01 (m, 1H), 3.04-2.78 (m, 4H), 1.57 (m, 4H), 1.33 (m, 4H), 0.92 (m, 6H), 0.86 (m, 2H), 0.61 (m, 2H); $^{31}$P NMR (CDCl$_3$) δ 20.35.

Example 34

Bisphosphonamidate 34: A mixture of phosphonic acid 6 (70 mg, 0.21 mmol), L-phenylalanine isobutyl ester hydrochloride (0.33 g, 1.26 mmol), and triethylamine (0.36 mL, 2.52 mmol) in pyridine (1.0 mL) was heated to 60° C. for 5 min. A freshly prepared bright yellow solution of aldrithiol (0.33 g, 1.47 mmol) and triphenylphosphine (0.39 g, 1.47 mmol) in pyridine (1.0 mL) was added to the above reaction mixture. The reaction was stirred at 60° C. overnight, cooled to room temperature, and concentrated. The product was partitioned between EtOAc and saturated NaHCO$_3$. The organic phase was washed with brine, dried with Na$_2$SO$_4$, filtered, and evaporated under reduced pressure. The crude product was purified by column chromatography on silica gel (10% MeOH/CH$_2$Cl$_2$) to give the bisphosphonamidate (78 mg, 50%) as a pale yellow foam: $^1$H NMR (CDCl$_3$) δ 7.52 (s, 1H), 7.24-7.07 (m, 10H), 4.26 (m, 1H), 4.11 (m, 2H), 4.01 (m, 1H), 3.85 (m, 4H), 3.66 (m, 2H), 3.35-3.25 (m, 2H), 3.07-2.85 (m, 3H), 2.97-2.79 (m, 2H), 1.89 (m, 2H), 0.90 (m, 12H), 0.89 (m, 2H), 0.62 (m, 2H); $^{31}$P NMR (CDCl$_3$) δ 20.31.

Example 35

BisPOC of cPrPMEDAP 35: A mixture of phosphonic acid 6 (0.20 g, 0.61 mmol) and triethylamine (0.42 mL, 3.01 mmol) in 1-methyl-2-pyrrolidinone (2.0 mL) was heated to 60° C. for 30 min. POCCl (0.45 g, 2.92 mmol) was added. The reaction mixture was stirred at 60° C. for 3 h, cooled to room temperature, and concentrated. The product was partitioned between EtOAc and saturated NaHCO$_3$. The organic phase was washed with brine, dried with Na$_2$SO$_4$, filtered, and evaporated under reduced pressure. The crude product was purified by chromatography on ISCO (2-propanol/CH$_2$Cl$_2$) to give the bisPOC of cPrPMEDAP (0.13 g, 39%) as a solid: $^1$H NMR (CDCl$_3$) δ 7.58 (s, 1H), 5.66 (m, 4H), 4.92 (m, 2H), 4.22 (m, 2H), 3.90-3.88 (m, 4H), 3.01 (broad, s, 1H), 1.81 (m, 12H), 0.86 (m, 2H), 0.62 (m, 2H); $^{31}$P NMR (CDCl$_3$) δ 20.93.

Examples 36 to 38 refer to Scheme 10.

Example 36

Bisphosphonamidate 37: A mixture of phosphonic acid 36 (0.32 g, 1.00 mmol), L-alanine butyl ester hydrochloride (0.47 g, 2.60 mmol), and triethylamine (0.27 g, 2.60 mmol) in pyridine (5.0 mL) was heated to 60° C. for 5 min. A freshly prepared bright yellow solution of aldrithiol (0.77 g, 3.50 mmol) and triphenylphosphine (0.92 g, 3.50 mmol) in pyridine (2.0 mL) was added to the above reaction mixture. The reaction was stirred at 60° C. overnight, cooled to room temperature, and concentrated. The product was partitioned between EtOAc and saturated NaHCO$_3$. The organic phase was washed with brine, dried with Na$_2$SO$_4$, filtered, and evaporated under reduced pressure. The crude product was purified by column chromatography on silica gel (10% MeOH/CH$_2$Cl$_2$) to give the bisphosphonamidate (0.43 g, 75%) as a pale yellow foam.

Example 37

Monophosphonic Acid 38: A mixture of diacid 36 (1.30 g, 4.10 mmol) and DMF (0.1 mL) in sulfolane (35 mL) was heated to 70° C. Thionylchloride (0.54 mL, 7.38 mmol) was added dropwise over a period of 1 h. The temperature was increased to 90° C. and TMSOPh (0.75 g, 4.51 mmol) was added and stirred for 1 h. The reaction mixture was cooled to room temperature overnight. The reaction mixture was added dropwise to well-stirred, ice-cold acetone (100 mL). The product was precipitated out. The solid was filtered and dissolved in MeOH (40 mL) and pH was adjusted to 3 with 45% KOH. Solid was collected by filtration. The product was further purified by dissolving in MeOH, adjusting pH to 6 with 45% KOH, and crystallizing from ice-cold acetone to give the monophosphonic acid (0.20 g, 12%) as an off-white solid.

Example 38

Monophosphonamidate 39: A mixture of monophosphonic acid 38 (0.20 g, 0.50 mmol), L-alanine isopropyl ester hydrochloride (0.17 g, 1.00 mmol) and triethylamine (0.10 g, 1.00 mmol) in pyridine (2.0 mL) was heated to 60° C. for 5 min. A freshly prepared bright yellow solution of aldrithiol (0.39 g, 1.75 mmol) and triphenylphosphine (0.46 g, 1.75 mmol) in pyridine (2.0 mL) was added to the above reaction mixture. The reaction was stirred at 60° C. overnight, cooled to room temperature, and concentrated. The product was partitioned between EtOAc and saturated NaHCO$_3$. The organic phase was washed with brine, dried with Na$_2$SO$_4$, filtered, and evaporated under reduced pressure. The crude product was purified by column chromatography on silica gel (7% MeOH/CH$_2$Cl$_2$) to give the monophosphonamidate (0.14 g, 54%, 1:1 diastereomeric mixture) as a pale yellow foam.

Example 39 refers to Scheme 11

Example 39

Bisphosphonamidate 41: A mixture of phosphonic acid 40 (0.36 g, 1.00 mmol), L-alanine n-butyl ester hydrochloride (0.47 g, 2.60 mmol), and triethylamine (0.27 g, 2.60 mmol) in pyridine (5.0 mL) was heated to 60° C. for 5 min. A freshly prepared bright yellow solution of aldrithiol (0.77 g, 3.50 mmol) and triphenylphosphine (0.92 g, 3.50 mmol) in pyridine (2.0 mL) was added to the above reaction mixture. The reaction was stirred at 60° C. overnight, cooled to room temperature, and concentrated. The product was partitioned between EtOAc and saturated NaHCO$_3$. The organic phase was washed with brine, dried with Na$_2$SO$_4$, filtered, and evaporated under reduced pressure. The crude product was purified by column chromatography on silica gel (10% MeOH/CH$_2$Cl$_2$) to give the bisphosphonamidate (0.32 g, 35%) as a pale yellow foam.

Examples 40 to 56 refer to Schemes 12 to 16.

Example 40

Bisphosphonamidate 43: A mixture of phosphonic acid 42 (0.37 g, 1.00 mmol), L-alanine n-butyl ester hydrochloride (0.47 g, 2.60 mmol), and triethylamine (0.27 g, 2.60 mmol) in pyridine (5.0 mL) was heated to 60° C. for 5 min. A freshly prepared bright yellow solution of aldrithiol (0.77 g, 3.50 mmol) and triphenylphosphine (0.92 g, 3.50 mmol) in pyridine (2.0 mL) was added to the above reaction mixture. The reaction was stirred at 60° C. overnight, cooled to room temperature, and concentrated. The product was partitioned between EtOAc and saturated NaHCO$_3$. The organic phase was washed with brine, dried with Na$_2$SO$_4$, filtered, and evaporated under reduced pressure. The crude product was purified by column chromatography on silica gel (10% MeOH/CH$_2$Cl$_2$) to give the bisphosphonamidate (0.53 g, 85%) as a pale yellow foam.

Example 41

Bisphosphonamidate 45: A mixture of phosphonic acid 44 (0.55 g, 2.00 mmol), L-alanine butyl ester hydrochloride (0.94 g, 5.20 mmol), and triethylamine (0.54 g, 5.20 mmol) in pyridine (5.0 mL) was heated to 60° C. for 5 min. A freshly prepared bright yellow solution of aldrithiol (1.54 g, 7.00 mmol) and triphenylphosphine (1.84 g, 7.00 mmol) in pyridine (5.0 mL) was added to the above reaction mixture. The reaction was stirred at 60° C. overnight, cooled to room temperature, and concentrated. The product was partitioned between EtOAc and saturated NaHCO$_3$. The organic phase was washed with brine, dried with Na$_2$SO$_4$, filtered, and evaporated under reduced pressure. The crude product was purified by column chromatography on silica gel (10% MeOH/CH$_2$Cl$_2$) to give the bisphosphonamidate (0.48 g, 45%) as a pale yellow foam.

Example 42

Monophosphonic Acid 46: A mixture of diacid 44 (10.00 g, 36.30 mmol) and DMF (0.2 mL) in sulfolane (50 mL) was heated to 70° C. Thionylchloride (4.72 mL, 64.70 mmol) was added dropwise over a period of 1 h. The temperature was increased to 90° C. and TMSOPh (6.65 g, 40.00 mmol) was added and stirred for 1 h. The reaction mixture was cooled to room temperature overnight. The reaction mixture was added dropwise to well-stirred, ice-cold acetone (100 mL). The product was precipitated out. The solid was filtered and dissolved in MeOH (40 mL) and pH was adjusted to 3 with 45% KOH. Solid was collected by filtration and dried under vacuum to give the monophosphonic acid (12.40 g, 97%) as a solid.

Example 43

Monophosphonamidate 47: A mixture of monophosphonic acid 46 (1.00 g, 2.86 mmol), L-alanine methyl ester hydrochloride (0.80 g, 5.73 mmol) and triethylamine (0.58 g, 5.73 mmol) in pyridine (5.0 mL) was heated to 60° C. for 5 min. A freshly prepared bright yellow solution of aldrithiol (2.21 g, 10.00 mmol) and triphenylphosphine (2.63 g, 10.00 mmol) in pyridine (5.0 mL) was added to the above reaction mixture. The reaction was stirred at 60° C. overnight, cooled to room temperature, and concentrated. The product was partitioned between EtOAc and saturated NaHCO$_3$. The organic phase was washed with brine, dried with Na$_2$SO$_4$, filtered, and evaporated under reduced pressure. The crude product was purified by column chromatography on silica gel (7% MeOH/CH$_2$Cl$_2$) to give the monophosphonamidate (0.80 g, 64%, 1:1 diastereomeric mixture) as a pale yellow oil.

Example 44

Monophosphonamidate 48: A mixture of monophosphonic acid 46 (0.35 g, 1.00 mmol), L-alanine isopropyl ester hydrochloride (0.34 g, 2.00 mmol) and triethylamine (0.20 g, 2.00 mmol) in pyridine (2.0 mL) was heated to 60° C. for 5 min. A freshly prepared bright yellow solution of aldrithiol (0.77 g, 3.50 mmol) and triphenylphosphine (0.92 g, 3.50 mmol) in pyridine (2.0 mL) was added to the above reaction mixture. The reaction was stirred at 60° C. overnight, cooled to room temperature, and concentrated. The product was partitioned between EtOAc and saturated NaHCO$_3$. The organic phase was washed with brine, dried with Na$_2$SO$_4$, filtered, and evaporated under reduced pressure. The crude product was purified by column chromatography on silica gel (7% MeOH/CH$_2$Cl$_2$) to give the monophosphonamidate containing some impurity. The resulting compound was treated with fumaric acid (77 mg) in hot CH$_3$CN (10 mL) and cooled to room temperature. The product was precipitated out and dried under vacuum to give the fumarate salt of monophosphonamidate (0.13 g, 22%, 1:1 diastereomeric mixture) as a solid.

Example 45

Benzyl Ether of PMEG 50: A mixture of diacid 49 (0.62 g, 2.00 mmol) and benzyl alcohol (10 mL) was cooled to 0° C. with stirring. Sodium hydride (0.24 g, 10.00 mmol) was added portion wise and the reaction mixture was heated to 100° C. over 1 h. Additional benzyl alcohol (20 mL) and sodium hydride (0.12 g, 5.00 mmol) were added. The reaction was stirred at 140° C. for 1 h and cooled to room temperature. The volatiles were evaporated under reduced pressure, water (50 mL) was added, and the pH was adjusted to 11 with NaOH. The product was partitioned between toluene (3×) and H$_2$O. The aqueous phase was acidified with HCl to pH=3 and kept at 0° C. overnight. The product was collected and dried under vacuum to give the benzyl ether (0.18 g, 22%) as a tan solid.

Example 46

Monophosphonamidate 51: A mixture of phosphonic acid 50 (0.13 g, 0.34 mmol), L-alanine isopropyl ester hydrochloride (0.11 g, 0.68 mmol), phenol (0.16 g, 1.69 mmol) and triethylamine (0.28 mL, 2.03 mmol) in pyridine (2.0 mL) was heated to 60° C. for 5 min. A freshly prepared bright yellow solution of aldrithiol (0.52 g, 2.37 mmol) and triphenylphosphine (0.62 g, 2.37 mmol) in pyridine (2.0 mL) was added to the above reaction mixture. The reaction was stirred at 60° C. overnight, cooled to room temperature, and concentrated. The product was partitioned between EtOAc and saturated NaHCO$_3$. The organic phase was washed with brine, dried with Na$_2$SO$_4$, filtered, and evaporated under reduced pressure. The crude product was purified by column chromatography on silica gel (5% MeOH/CH$_2$Cl$_2$) to give the monophosphonamidate (50 mg, 26%, 1:1 diastereomeric mixture) as a thick oil.

Example 47

Monophosphonamidate 52: A mixture of monophosphonamidate 51 (50 mg, 0.09 mmol) and Pd(OH)$_2$/C (50 mg) in iPrOH (3 mL) was stirred at room temperature under 1 atm of H$_2$ (balloon) overnight. The reaction mixture was filtered through a plug of celite and the solvent was removed on rotavap under reduced pressure. The crude product was purified by column chromatography on silica gel (5-15% MeOH/CHCl$_3$) to give the monophosphonamidate (40 mg, 95%, 1:1 diastereomeric mixture) as an off-white foam.

Example 48

Bisphosphonamidate 54: A mixture of phosphonic acid 53 (0.10 g, 0.35 mmol), L-alanine butyl ester hydrochloride (0.38 g, 2.10 mmol), and triethylamine (0.58 mL, 4.20 mmol) in pyridine (1.0 mL) was heated to 60° C. for 5 min. A freshly prepared bright yellow solution of aldrithiol (0.53 g, 2.45 mmol) and triphenylphosphine (0.64 g, 2.45 mmol) in pyridine (1.0 mL) was added to the above reaction mixture. The reaction was stirred at 60° C. overnight, cooled to room temperature, and concentrated. The product was partitioned between EtOAc and saturated NaHCO$_3$. The organic phase was washed with brine, dried with Na$_2$SO$_4$, filtered, and evaporated under reduced pressure. The crude product was purified by column chromatography on silica gel (15% MeOH/CH$_1$Cl$_2$) to give the bisphosphonamidate (25 mg, 13%) as a pale yellow foam: $^1$H NMR (CD$_3$OD) δ 7.82 (s, 1H), 4.26 (m, 2H), 4.11 (m, 4H), 3.94 (m, 2H), 3.88 (m, 2H), 3.78 (m, 2H), 1.61 (m, 4H), 1.39 (m, 4H), 1.34 (m, 6H), 0.95 (m, 6H); $^{31}$P NMR (CDCl$_3$) δ 23.39.

Example 49

Diisopropyl Phosphonate 55: A mixture of 4 (3.00 g, 7.66 mmol) and 10% Pd/C (0.60 g) in MeOH (30 mL) was stirred at room temperature under 1 atm of H$_2$ (balloon) overnight. The reaction mixture was filtered through a plug of celite and the solvent was removed on rotavap. The crude product was purified by column chromatography on silica gel (5% MeOH/CHCl$_3$) to give the diisopropyl phosphonate (2.08 g, 76%) as a thick oil which was solidified upon standing: $^1$H NMR (CDCl$_3$) δ 8.72 (s, 1H), 7.94 (s, 1H), 4.73 (m, 2H), 4.33 (m, 2H), 3.97 (m, 2H), 3.73 (d, J=8.1 Hz, 2H), 1.31 (m, 12H); $^{31}$P NMR (CDCl$_3$) δ 18.47.

Example 50

Phosphonic Acid 56: Diisopropyl phosphonate 55 (0.10 g, 0.28 mmol) was dissolved in CH$_3$CN (1.5 mL) and cooled to 0° C. Bromotrimethylsilane (0.18 mL, 1.40 mmol) was added. The reaction mixture was stirred at 0° C. for 2 h and warmed to room temperature overnight. DMF (0.5 mL) was added to form a solution and stirred for 2 h. MeOH was added and stirred for 2 h. Volatiles were evaporated under reduced pressure. The remaining DMF solution was added slowly to ice-cold CH$_3$CN and the product precipitated out. The solid was collected and dried under vacuum to give the phosphonic acid (74 mg, 95%) as a white solid.

Example 51

Bisphosphonamidate 57: A mixture of phosphonic acid 56 (23 mg, 0.08 mmol), L-alanine n-butyl ester hydrochloride (91 mg, 0.50 mmol), and triethylamine (0.14 mL, 0.96 mmol) in pyridine (0.5 mL) was heated to 60° C. for 5 min. A freshly prepared bright yellow solution of aldrithiol (0.11 g, 0.56 mmol) and triphenylphosphine (0.12 g, 0.56 mmol) in pyridine (0.5 mL) was added to the above reaction mixture. The reaction was stirred at 60° C. overnight, cooled to room temperature, and concentrated. The product was partitioned between EtOAc and saturated NaHCO$_3$. The organic phase was washed with brine, dried with Na$_2$SO$_4$, filtered, and evaporated under reduced pressure. The crude product was purified by chromatography on ISCO (2-propanol/CH$_2$Cl$_2$) to give the bisphosphonamidate (17 mg, 38%) as a pale yellow foam: $^1$H NMR (CDCl$_3$) δ 8.65 (s, 1H), 7.94 (s, 1H), 5.20 (s, broad, 2H), 4.35 (m, 2H), 4.20-3.92 (m, 6H), 3.89 (m, 2H), 3.72 (m, 2H), 3.42-3.19 (m, 2H), 1.61 (m, 4H), 1.32 (m, 8H), 0.96 (m, 6H); $^{31}$P NMR (CDCl$_3$) δ 20.70.

Example 52

Monophosphonamidate 58: A mixture of phosphonic acid 56 (20 mg, 0.07 mmol), L-phenylalanine ethyl ester hydrochloride (33 mg, 0.14 mmol), phenol (33 mg, 0.35 mmol) and triethylamine (0.12 mL, 0.84 mmol) in pyridine (0.5 mL) was heated to 60° C. for 5 min. A freshly prepared bright yellow solution of aldrithiol (0.11 g, 0.56 mmol) and triphenylphosphine (0.12 g, 0.56 mmol) in pyridine (0.5 mL) was added to the above reaction mixture. The reaction was stirred at 60° C. overnight, cooled to room temperature, and concentrated. The product was partitioned between EtOAc and saturated NaHCO$_3$. The organic phase was washed with brine, dried with Na$_2$SO$_4$, filtered, and evaporated under reduced pressure. The crude product was purified by chromatography on ISCO (2-propanol/CH$_2$Cl$_2$) to give the monophosphonamidate (13 mg, 34%, 1:1 diastereomeric mixture) as an off-white foam: $^1$H NMR (CDCl$_3$) δ 8.69 (d, J=15.0 Hz, 1H), 7.84 (d, J=4.2 Hz, 1H), 7.25-6.97 (m, 10H), 4.35 (m, 1H), 4.23 (m, 2H), 4.08 (m, 2H), 3.85 (m, 1H), 3.72 (m, 1H), 3.73-3.62 (m, 1H), 3.38 (m, 1H), 2.95-2.86 (m, 2H), 1.17 (m, 3H); $^{31}$P NMR (CDCl$_3$) δ 21.67, 20.84.

Example 53

Diisopropyl Phosphonate 59: A mixture of compound 4 (1.00 g, 2.56 mmol) and allylamine (3 mL) in CH$_3$CN (3.0 mL) was placed in a scintillation vial and heated to 65° C. for 5 h. The reaction mixture was cooled to room temperature and concentrated under reduced pressure. The product was partitioned between EtOAc and brine, dried with Na$_2$SO$_4$, filtered, and concentrated. The product was dissolved in minimal CH$_3$CN and H$_2$O was added and lyophilized to give the diisopropyl phosphonate (1.00 g, 95%).

Example 54

Phosphonic Acid 60: Diisopropyl phosphonate 59 (1.00 g, 2.43 mmol) was dissolved in CH$_3$CN (1.5 mL) and cooled to 0° C. Bromotrimethylsilane (0.31 mL, 12.15 mmol) was added. The reaction mixture was stirred at 0° C. for 2 h and warmed to room temperature overnight. DMF (0.5 mL) was added to form a solution and stirred for 2 h. MeOH was added and stirred for 2 h. Volatiles were evaporated under reduced pressure. The remaining DMF solution was added slowly to ice-cold CH$_3$CN and the product precipitated out. The solid was collected and dried under vacuum to give the phosphonic acid (0.48 g, 60%) as a white solid.

Example 55

Monophosphonamidate 61 and Bisphosphonamidate 62: A mixture of diacid 60 (0.40 g, 1.20 mmol), L-alanine isopropyl ester hydrochloride (0.49 g, 2.40 mmol), phenol (0.68 g, 7.20 mmol), and triethylamine (1.0 mL, 7.20 mmol) in pyridine (3.0 mL) was heated to 60° C. for 5 min. A freshly prepared bright yellow solution of aldrithiol (1.84 g, 8.40 mmol) and triphenylphosphine (2.20 g, 8.40 mmol) in pyridine (3.0 mL) was added to the above reaction mixture. The reaction was stirred at 60° C. overnight, cooled to room temperature, and concentrated. The product was partitioned between EtOAc and saturated NaHCO$_3$. The organic phase was washed with brine, dried with Na$_2$SO$_4$, filtered, and evaporated under reduced pressure. The crude product was purified by column chromatography on silica gel (5-10% MeOH/CH$_2$Cl$_2$) to give monophosphonamidate 61 (0.52 g, 37%, 1:1 diastereomeric mixture) and bisphosphonamidate 62 (0.13 g, 20%).

Example 56

Bisphosphonamidate 63: A mixture of phosphonic acid 60 (0.33 g, 1.00 mmol), L-alanine butyl ester hydrochloride (0.47 g, 2.60 mmol), and triethylamine (0.27 g, 2.60 mmol) in pyridine (5.0 mL) was heated to 60° C. for 5 min. A freshly prepared bright yellow solution of aldrithiol (0.77 g, 3.50 mmol) and triphenylphosphine (0.92 g, 3.50 mmol) in pyridine (2.0 mL) was added to the above reaction mixture. The reaction was stirred at 60° C. overnight, cooled to room temperature, and concentrated. The product was partitioned between EtOAc and saturated NaHCO$_3$. The organic phase was washed with brine, dried with Na$_2$SO$_4$, filtered, and evaporated under reduced pressure. The crude product was purified by column chromatography on silica gel (10% MeOH/CH$_2$Cl$_2$) to give the bisphosphonamidate (0.32 g, 55%) as a pale yellow foam.

Example 57 relates to Scheme 17.

Example 57

BisPOC of 6-allylPMEDAP 64: A mixture of phosphonic acid 60 (0.20 g, 0.61 mmol) and triethylamine (0.42 mL, 3.01 mmol) in 1-methyl-2-pyrrolidinone (2.0 mL) was heated to 60° C. for 30 min. POCCl (0.45 g, 2.92 mmol) was added. The reaction mixture was stirred at 60° C. for 3 h, cooled to room temperature, and concentrated. The product was partitioned between EtOAc and saturated NaHCO$_3$. The organic phase was washed with brine, dried with Na$_2$SO$_4$, filtered, and evaporated under reduced pressure. The crude product was purified by chromatography on ISCO (2-propanol/CH$_2$Cl$_2$) to give the bisPOC of 6-allylPMEDAP 64 (0.11 g, 32%, GS 192727) as a solid: $^1$H NMR (CDCl$_3$) δ 7.60 (s, 1H), 6.00 (m, 1H), 5.66 (m, 4H), 5.30 (dd, 1H), 5.17 (dd, 1H), 4.92 (m, 2H), 4.80 (s, 2H), 4.22 (m, 4H), 3.95 (m, 4H), 1.35 (m, 12H); $^{31}$P NMR (CDCl$_3$) δ 20.94.

Examples 58 to 61 relate to Scheme 18.

Example 58

Bisphosphoamidate 65: A mixture of phosphonic acid 60 (35 mg, 0.11 mmol), L-alanine ethyl ester hydrochloride (0.1 g, 0.65 mmol), and triethylamine (0.2 mL, 1.43 mmol) in pyridine (0.5 mL) was heated to 60° C. for 5 min. A freshly prepared bright yellow solution of aldrithiol (0.16 g, 0.74 mmol) and triphenylphosphine (0.20 g, 0.75 mmol) in pyridine (0.5 mL) was added to the above reaction mixture. The reaction was stirred at 60° C. overnight, cooled to room temperature, and concentrated. The product was partitioned between EtOAc and saturated NaHCO$_3$. The organic phase was washed with brine, dried with Na$_2$SO$_4$, filtered, and evaporated under reduced pressure. The crude product was purified by chromatography on ISCO (2-propanol/CH$_2$Cl$_2$) to give the bisphosphoamidate (23 mg, 41%) as a pale yellow foam: $^1$H NMR (CDCl$_3$) δ 7.70 (s, 1H), 6.00 (m, 1H), 5.30

(dd, 1H), 5.17 (dd, 1H), 4.30 (m, 4H), 4.20-4.00 (m, 6H), 3.89 (m, 2H), 3.72 (m, 2H), 3.42 (m, 1H), 3.22 (m, 1H), 1.45-1.25 (m, 12H); $^{31}$P NMR (CDCl$_3$) δ 20.77.

Example 59

Bisphosphoamidate 66: A mixture of phosphonic acid 60 (0.10 g, 0.30 mmol), L-alanine cyclobutyl ester hydrochloride (0.33 g, 0.91 mmol), and triethylamine (0.50 mL, 3.59 mmol) in pyridine (2.0 mL) was heated to 60° C. for 5 min. A freshly prepared bright yellow solution of aldrithiol (0.47 g, 2.12 mmol) and triphenylphosphine (0.56 g, 2.14 mmol) in pyridine (1.0 mL) was added to the above reaction mixture. The reaction was stirred at 60° C. overnight, cooled to room temperature, and concentrated. The product was partitioned between EtOAc and saturated NaHCO$_3$. The organic phase was washed with brine, dried with Na$_2$SO$_4$, filtered, and evaporated under reduced pressure. The crude product was purified by chromatography on ISCO (2-propanol/CH$_2$Cl$_2$) to give the bisphosphoamidate (45 mg, 26%) as a pale yellow foam: $^1$H NMR (CDCl$_3$) δ 7.60 (s, 1H), 6.00 (m, 1H), 5.30 (dd, 1H), 5.18 (dd, 1H), 5.00 (m, 2H), 4.78 (s, 2H), 4.30 (m, 4H), 4.00 (m, 2H), 3.89 (m, 2H), 3.72 (m, 2H), 3.38 (m, 1H), 3.19 (m, 1H), 2.38 (m, 4H), 2.10 (m, 4H), 1.85-1.60 (m, 4H), 1.45 (m, 6H); $^{31}$P NMR (CDCl$_3$) δ 20.61.

Example 60

Bisphosphoamidate 67: A mixture of phosphonic acid 60 (0.10 g, 0.30 mmol), L-alanine n-hexyl ester hydrochloride (0.25 g, 1.21 mmol), and triethylamine (0.7 mL, 5.02 mmol) in pyridine (2.0 mL) was heated to 60° C. for 5 min. A freshly prepared bright yellow solution of aldrithiol (0.47 g, 2.12 mmol) and triphenylphosphine (0.56 g, 2.14 mmol) in pyridine (1.0 mL) was added to the above reaction mixture. The reaction was stirred at 60° C. overnight, cooled to room temperature, and concentrated. The product was partitioned between EtOAc and saturated NaHCO$_3$. The organic phase was washed with brine, dried with Na$_2$SO$_4$, filtered, and evaporated under reduced pressure. The crude product was purified by chromatography on ISCO (2-propanol/CH$_2$Cl$_2$) to give the bisphosphoamidate (80 mg, 41%) as a pale yellow foam: $^1$H NMR (CDCl$_3$) δ 7.65 (s, 1H), 6.00 (m, 1H), 5.30 (dd, 1H), 5.17 (dd, 1H), 4.80 (s, 2H), 4.25 (m, 4H), 4.20-4.00 (m, 6H), 3.85 (m, 2H), 3.72 (m, 2H), 3.42 (m, 1H), 3.20 (m, 1H), 1.70 (m, 4H), 1.32 (m, 18H), 0.96 (m, 6H); $^{31}$P NMR (CDCl$_3$) δ 20.61.

Example 61

Bisphosphoamidate 68: A mixture of phosphonic acid 60 (35 mg, 0.11 mmol), L-2-aminobutyric acid n-butyl ester hydrochloride (0.13 g, 0.64 mmol), and triethylamine (0.2 mL, 1.43 mmol) in pyridine (0.5 mL) was heated to 60° C. for 5 min. A freshly prepared bright yellow solution of aldrithiol (0.16 g, 0.74 mmol) and triphenylphosphine (0.20 g, 0.75 mmol) in pyridine (0.5 mL) was added to the above reaction mixture. The reaction was stirred at 60° C. overnight, cooled to room temperature, and concentrated. The product was partitioned between EtOAc and saturated NaHCO$_3$. The organic phase was washed with brine, dried with Na$_2$SO$_4$, filtered, and evaporated under reduced pressure. The crude product was purified by chromatography on ISCO (2-propanol/CH$_2$Cl$_2$) to give the bisphosphoamidate (32 mg, 49%) as a pale yellow foam: $^1$H NMR (CDCl$_3$) δ 7.68 (s, 1H), 6.00 (m, 1H), 5.70 (s, broad, 1H), 5.30 (dd, 1H), 5.18 (dd, 1H), 4.80 (s, 2H), 4.25 (m, 4H), 4.20-4.05 (m, 6H), 3.89 (m, 2H), 3.72 (m, 2H), 3.35 (m, 1H), 3.15 (m, 1H), 1.86-1.60 (m, 8H), 1.40 (m, 4H), 0.96 (m, 12H); $^{31}$P NMR (CDCl$_3$) δ21.25.

Examples 62 to 71 related to Scheme 19.

Example 62

Bisphosphoamidate 69: A mixture of phosphonic acid 60 (35 mg, 0.11 mmol), L-phenylalanine ethyl ester hydrochloride (0.15 g, 0.65 mmol), and triethylamine (0.2 mL, 1.43 mmol) in pyridine (0.5 mL) was heated to 60° C. for 5 min. A freshly prepared bright yellow solution of aldrithiol (0.16 g, 0.74 mmol) and triphenylphosphine (0.20 g, 0.75 mmol) in pyridine (0.5 mL) was added to the above reaction mixture. The reaction was stirred at 60° C. overnight, cooled to room temperature, and concentrated. The product was partitioned between EtOAc and saturated NaHCO$_3$. The organic phase was washed with brine, dried with Na$_2$SO$_4$, filtered, and evaporated under reduced pressure. The crude product was purified by chromatography on ISCO (2-propanol/CH$_2$Cl$_2$) to give the bisphosphoamidate (28 mg, 39%) as a pale yellow foam: $^1$H NMR (CDCl$_3$) δ 7.58 (s, 1H), 7.28-7.03 (m, 10H), 6.00 (m, 1H), 5.30 (dd, 1H), 5.17 (dd, 1H), 4.25-4.00 (m, 8H), 3.65 (m, 2H), 3.42-3.19 (m, 2H), 3.15-2.77 (m, 6H), 1.23 (m, 6H); $^{31}$P NMR (CDCl$_3$) δ 20.34.

Example 63

Bisphosphoamidate 70: A mixture of phosphonic acid 60 (35 mg, 0.11 mmol), L-phenylalanine n-butyl ester hydrochloride (0.15 g, 0.58 mmol), and triethylamine (0.2 mL, 1.43 mmol) in pyridine (0.5 mL) was heated to 60° C. for 5 min. A freshly prepared bright yellow solution of aldrithiol (0.16 g, 0.74 mmol) and triphenylphosphine (0.20 g, 0.75 mmol) in pyridine (0.5 mL) was added to the above reaction mixture. The reaction was stirred at 60° C. overnight, cooled to room temperature, and concentrated. The product was partitioned between EtOAc and saturated NaHCO$_3$. The organic phase was washed with brine, dried with Na$_2$SO$_4$, filtered, and evaporated under reduced pressure. The crude product was purified by chromatography on ISCO (2-propanol/CH$_2$Cl$_2$) to give the bisphosphoamidate (49 mg, 63%) as a pale yellow foam: $^1$H NMR (CDCl$_3$) δ 7.58 (s, 1H), 7.28-7.03 (m, 10H), 6.00 (m, 1H), 5.70 (s, broad, 1H), 5.30 (dd, 1H), 5.17 (dd, 1H), 4.78 (s, 2H), 4.25-4.03 (m, 8H), 3.65 (m, 2H), 3.42-3.19 (m, 2H), 3.17-2.78 (m, 6H), 1.61 (m, 4H), 1.32 (m, 4H), 0.96 (m, 6H); $^{31}$P NMR (CDCl$_3$) δ 20.35.

Example 64

Bisphosphoamidate 71: A mixture of phosphonic acid 60 (0.10 g, 0.30 mmol), L-phenylalanine isobutyl ester hydrochloride (0.31 g, 1.20 mmol), and triethylamine (0.7 mL, 5.02 mmol) in pyridine (2.0 mL) was heated to 60° C. for 5 min. A freshly prepared bright yellow solution of aldrithiol (0.44 g, 2.00 mmol) and triphenylphosphine (0.53 g, 2.00 mmol) in pyridine (1.0 mL) was added to the above reaction mixture. The reaction was stirred at 60° C. overnight, cooled to room temperature, and concentrated. The product was partitioned between EtOAc and saturated NaHCO$_3$. The organic phase was washed with brine, dried with Na$_2$SO$_4$, filtered, and evaporated under reduced pressure. The crude product was purified by chromatography on ISCO (2-propanol/CH$_2$Cl$_2$) to give the bisphosphoamidate (94 mg, 42%) as a pale yellow foam: $^1$H NMR (CDCl$_3$) δ 7.55 (s, 1H), 7.27-7.03 (m, 10H), 6.00 (m, 1H), 5.70 (s, broad, 1H), 5.25 (dd, 1H), 5.17 (dd, 1H), 4.78 (s, 2H), 4.25-4.08 (m, 4H), 3.87 (m, 4H), 3.65 (m, 2H), 3.42-3.19 (m, 2H), 3.17-2.78 (m, 6H), 1.97 (m, 2H), 0.96 (m, 12H); $^{31}$P NMR (CDCl$_3$) δ 20.31.

Example 65

Monophosphoamidate 72: A mixture of phosphonic acid 60 (35 mg, 0.11 mmol), L-alanine ethyl ester hydrochloride (32 mg, 0.20 mmol), phenol (50 mg, 0.53 mmol) and triethylamine (0.2 mL, 1.43 mmol) in pyridine (0.5 mL) was heated to 60° C. for 5 min. A freshly prepared bright yellow solution of aldrithiol (0.16 g, 0.74 mmol) and triphenylphosphine (0.20 g, 0.75 mmol) in pyridine (0.5 mL) was added to the above reaction mixture. The reaction was stirred at 60° C. overnight, cooled to room temperature, and concentrated. The product was partitioned between EtOAc and saturated NaHCO$_3$. The organic phase was washed with brine, dried with Na$_2$SO$_4$, filtered, and evaporated under reduced pressure. The crude product was purified by chromatography on ISCO (2-propanol/CH$_2$Cl$_2$) to give the monophosphoamidate (12 mg, 22%, 1:1 diastereomeric mixture) as an off-white foam: $^1$H NMR (CDCl$_3$) δ 7.62 (d, 1H), 7.30-7.04 (m, 5H), 6.00 (m, 1H), 5.30 (dd, 1H), 5.18 (dd, 1H), 4.30-4.05 (m, 7H), 3.90-3.80 (m, 4H), 1.23 (m, 6H); $^{31}$P NMR (CDCl$_3$) δ 21.89, 20.65.

Example 66

Monophosphoamidate 73: A mixture of phosphonic acid 60 (35 mg, 0.11 mmol), L-alanine n-butyl ester hydrochloride (39 mg, 0.21 mmol), phenol (50 mg, 0.53 mmol) and triethylamine (0.2 mL, 1.43 mmol) in pyridine (0.5 mL) was heated to 60° C. for 5 min. A freshly prepared bright yellow solution of aldrithiol (0.16 g, 0.74 mmol) and triphenylphosphine (0.20 g, 0.75 mmol) in pyridine (0.5 mL) was added to the above reaction mixture. The reaction was stirred at 60° C. overnight, cooled to room temperature, and concentrated. The product was partitioned between EtOAc and saturated NaHCO$_3$. The organic phase was washed with brine, dried with Na$_2$SO$_4$, filtered, and evaporated under reduced pressure. The crude product was purified by chromatography on ISCO (2-propanol/CH$_2$Cl$_2$) to give the monophosphoamidate (16 mg, 28%, 1:1 diastereomeric mixture) as an off-white foam: $^1$H NMR (CDCl$_3$) δ 7.61 (d, 1H), 7.32-7.06 (m, 5H), 6.00 (m,. 1H), 5.80 (s, broad, 1H), 5.30 (dd, 1H), 5.20 (dd, 1H), 4.80 (m, 2H), 4.30-4.05 (m, 7H), 3.90-3.80 (m, 4H), 3.90-3.60 (m, 2H), 1.60 (m, 2H), 1.32 (m, 5H), 0.96 (m, 3H); $^{31}$P NMR (CDCl$_3$) δ 21.96, 20.70.

Example 67

Monophosphoamidate 74: A mixture of phosphonic acid 60 (0.10 g, 0.30 mmol), L-alanine cyclobutyl ester hydrochloride (0.11 g, 0.61 mmol), phenol (0.13 g, 1.39 mmol) and triethylamine (0.5 mL, 3.59 mmol) in pyridine (2.0 mL) was heated to 60° C. for 5 min. A freshly prepared bright yellow solution of aldrithiol (0.47 g, 2.12 mmol) and triphenylphosphine (0.56 g, 2.14 mmol) in pyridine (1.0 mL) was added to the above reaction mixture. The reaction was stirred at 60° C. overnight, cooled to room temperature, and concentrated. The product was partitioned between EtOAc and saturated NaHCO$_3$. The organic phase was washed with brine, dried with Na$_2$SO$_4$, filtered, and evaporated under reduced pressure. The crude product was purified by chromatography on ISCO (2-propanol/CH$_2$Cl$_2$) to give the monophosphoamidate (28 mg, 17%, 1:1 diastereomeric mixture) as an off-white foam: $^1$H NMR (CDCl$_3$) δ 7.60 (d, 1H), 7.25-7.03 (m, 5H), 6.00 (m, 1H), 5.30 (dd, 1H), 5.18 (dd, 1H), 5.00 (m, 2H), 4.79 (d, 2H), 4.28-4.05 (m, 4H), 3.90 (m, 4H), 3.70 (m, 1H), 3.57 (m, 1H), 2.30 (m, 2H), 2.00-1.60 (m, 4H), 1.25 (m, 3H); $^{31}$P NMR (CDCl$_3$) δ 21.91, 20.64.

Example 68

Monophosphoamidate 75: A mixture of phosphonic acid 60 (0.10 g, 0.30 mmol), L-alanine n-hexyl ester hydrochloride (0.13 g, 0.61 mmol), phenol (0.14 g, 1.52 mmol) and triethylamine (0.7 mL, 5.02 mmol) in pyridine (2.0 mL) was heated to 60° C. for 5 min. A freshly prepared bright yellow solution of aldrithiol (0.47 g, 2.12 mmol) and triphenylphosphine (0.56 g, 2.14 mmol) in pyridine (1.0 mL) was added to the above reaction mixture. The reaction was stirred at 60° C. overnight, cooled to room temperature, and concentrated. The product was partitioned between EtOAc and saturated NaHCO$_3$. The organic phase was washed with brine, dried with Na$_2$SO$_4$, filtered, and evaporated under reduced pressure. The crude product was purified by chromatography on ISCO (2-propanol/CH$_2$Cl$_2$) to give the monophosphoamidate (28 mg, 16%, 1:1 diastereomeric mixture) as an off-white foam: $^1$H NMR (CDCl$_3$) δ 7.60 (d, 1H), 7.25-7.03 (m, 5H), 6.00 (m, 1H), 5.85 (s, 1H), 5.30 (dd, 1H), 5.17 (dd, 1H), 4.78 (d, 2H), 4.35-4.05 (m, 7H), 3.90 (m, 4H), 3.70 (m, 1H), 1.60 (m, 2H), 1.30 (m, 9H), 0.96 (m, 3H); $^{31}$P NMR (CDCl$_3$) δ 21.97, 20.69.

Examples 69 to 72 relate to Scheme 21.

Example 69

Monophosphoamidate 76: A mixture of phosphonic acid 60 (35 mg, 0.11 mmol), L-2-aminobutyric acid n-butyl ester hydrochloride (42 mg, 0.21 mmol), phenol (50 mg, 0.53 mmol) and triethylamine (0.2 mL, 1.43 mmol) in pyridine (0.5 mL) was heated to 60° C. for 5 min. A freshly prepared bright yellow solution of aldrithiol (0.16 g, 0.74 mmol) and triphenylphosphine (0.20 g, 0.75 mmol) in pyridine (0.5 mL) was added to the above reaction mixture. The reaction was stirred at 60° C. overnight, cooled to room temperature, and concentrated. The product was partitioned between EtOAc and saturated NaHCO$_3$. The organic phase was washed with brine, dried with Na$_2$SO$_4$, filtered, and evaporated under reduced pressure. The crude product was purified by chromatography on ISCO (2-propanol/CH$_2$Cl$_2$) to give the monophosphoamidate (17 mg, 29%, 1:1 diastereomeric mixture) as an off-white foam: $^1$H NMR (CDCl$_3$) δ 7.60 (d, 1H), 7.25-7.03 (m, 5H), 6.00 (m, 1H), 5.30 (dd, 1H), 5.17 (dd, 1H), 4.78 (d, 2H), 4.30-4.03 (m, 7H), 3.95-3.80 (m, 4H), 3.62 (m, 1H), 3.40 (m, 1H), 1.80-1.60 (m, 4H), 1.38 (m, 2H), 0.98-0.75 (m, 6H); $^{31}$P NMR (CDCl$_3$) δ 22.26, 20.95.

Example 70

Monophosphoamidate 77: A mixture of phosphonic acid 60 (35 mg, 0.11 mmol), L-phenylalanine ethyl ester hydrochloride (48 mg, 0.21 mmol), phenol (50 mg, 0.53 mmol) and triethylamine (0.2 mL, 1.43 mmol) in pyridine (0.5 mL) was heated to 60° C. for 5 min. A freshly prepared bright yellow solution of aldrithiol (0.16 g, 0.74 mmol) and triphenylphosphine (0.20 g, 0.75 mmol) in pyridine (0.5 mL) was added to the above reaction mixture. The reaction was stirred at 60° C. overnight, cooled to room temperature, and concentrated. The product was partitioned between EtOAc and saturated NaHCO$_3$. The organic phase was washed with brine, dried with Na$_2$SO$_4$, filtered, and evaporated under reduced pressure. The crude product was purified by chromatography on ISCO (2-propanol/CH$_2$Cl$_2$) to give the monophosphoamidate (14 mg, 23%, 1:1 diastereomeric mixture) as an off-white foam: $^1$H NMR (CDCl$_3$) δ 7.60 (d, 1H), 7.25-7.03 (m, 10H), 6.00 (m, 1H), 5.30 (dd, 1H), 5.17 (dd, 1H), 4.80 (m, 2H), 4.40-4.08 (m, 7H), 3.85-3.65 (m, 4H), 3.38-3.25 (m, 2H), 2.95-2.86 (m, 2H), 1.20 (m, 3H); $^{31}$P NMR (CDCl$_3$) δ 21.86, 21.06.

Example 71

Monophosphoamidate 78: A mixture of phosphonic acid 60 (35 mg, 0.11 mmol), L-phenylalanine n-butyl ester hydrochloride (55 mg, 0.21 mmol), phenol (50 mg, 0.53 mmol) and triethylamine (0.2 mL, 1.43 mmol) in pyridine (0.5 mL) was heated to 60° C. for 5 min. A freshly prepared bright yellow solution of aldrithiol (0.16 g, 0.74 mmol) and triphenylphosphine (0.20 g, 0.75 mmol) in pyridine (0.5 mL) was added to the above reaction mixture. The reaction was stirred at 60° C. overnight, cooled to room temperature, and concentrated. The product was partitioned between EtOAc and saturated NaHCO$_3$. The organic phase was washed with brine, dried with Na$_2$SO$_4$, filtered, and evaporated under reduced pressure. The crude product was purified by chromatography on ISCO (2-propanol/CH$_2$Cl$_2$) to give the monophosphoamidate (18 mg, 28%, 1:1 diastereomeric mixture) as an off-white foam: $^1$H NMR (CDCl$_3$) δ 7.60 (d, 1H), 7.25-6.97 (m, 10H), 6.00 (m, 1H), 5.80 (s, broad, 1H), 5.30 (dd, 1H), 5.17 (dd, 1H), 4.78 (d, 2H), 4.40-4.03 (m, 7H), 3.85-3.65 (m, 4H), 3.45-3.25 (m, 2H), 2.95-2.86 (m, 2H), 1.57 (m, 2H), 1.30 (m, 2H), 0.96 (m, 3H); $^{31}$P NMR (CDCl$_3$) δ 21.89, 21.09.

Example 72

Monophosphoamidate 79: A mixture of phosphonic acid 60 (0.10 g, 0.30 mmol), L-phenylalanine isobutyl ester hydrochloride (0.16 g, 0.61 mmol), phenol (0.14 g, 1.52 mmol) and triethylamine (0.7 mL, 5.02 mmol) in pyridine (2.0 mL) was heated to 60° C. for 5 min. A freshly prepared bright yellow solution of aldrithiol (0.47 g, 2.12 mmol) and triphenylphosphine (0.56 g, 2.14 mmol) in pyridine (1.0 mL) was added to the above reaction mixture. The reaction was stirred at 60° C. overnight, cooled to room temperature, and concentrated. The product was partitioned between EtOAc and saturated NaHCO$_3$. The organic phase was washed with brine, dried with Na$_2$SO$_4$, filtered, and evaporated under reduced pressure. The crude product was purified by chromatography on ISCO (2-propanol/CH$_2$Cl$_2$) to give the monophosphoamidate (19 mg, 10%, 1:1 diastereomeric mixture) as an off-white foam: $^1$H NMR (CDCl$_3$) δ 7.60 (d, 1H), 7.25-7.03 (m, 10H), 6.00 (m, 1H), 5.30 (dd, 1H), 5.17 (dd, 1H), 4.78 (d, 2H), 4.45 (m, 1H), 4.35-4.18 (m, 4H), 3.95-3.60 (m, 5H), 3.35 (m, 1H), 3.00-2.83 (m, 2H), 1.85 (m, 1H), 0.96 (m, 6H); $^{31}$P NMR (CDCl$_3$) δ 21.90, 21.07.

Examples 73 to 76 related to Scheme 22.

Example 73

Monophosphoamidate 80: A mixture of monophosphonic acid 6 (0.10 g, 0.30 mmol), L-alanine cyclobutyl ester hydrochloride (0.11 g, 0.61 mmol), phenol (0.13 g, 1.4 mmol), and triethylamine (0.51 mL, 3.67 mmol) in pyridine (2 mL) was heated to 60° C. for 5 min. A freshly prepared bright yellow solution of aldrithiol (0.47 g, 2.12 mmol) and triphenylphosphine (0.56 g, 2.14 mmol) in pyridine (1.0 mL) was added to the above reaction mixture. The reaction was stirred at 60° C. overnight, cooled to room temperature, and concentrated. The product was partitioned between EtOAc and saturated NaHCO$_3$. The organic phase was washed with brine, dried with Na$_2$SO$_4$, filtered, and evaporated under reduced pressure. The crude product was purified by chromatography on ISCO (2-propanol/CH$_2$Cl$_2$) followed by Gilson HPLC purification (CH$_3$CN/H$_2$O) to give the monophosphoamidate (33 mg, 20%, 1:1 diastereomeric mixture) as an off-white foam: $^1$H NMR (CDCl$_3$) δ 7.60 (s, 1H), 7.30-7.03 (m, 5H), 5.80 (s, broad, 1H), 5.00 (m, 1H), 4.80 (d, 2H), 4.28-4.05 (m, 3H), 3.90 (m, 4H), 3.03 (s, broad, 1H), 2.35 (m, 2H), 2.05 (m, 2H), 1.80 (m, 2H), 1.30 (m, 3H), 0.90 (m, 2H), 0.62 (m, 2H); $^{31}$P NMR (CDCl$_3$) δ 21.91, 20.61.

Example 74

Bisphosphoamidate 81: A mixture of phosphonic acid 6 (60 mg, 0.18 mmol), L-alanine cyclobutyl ester hydrochloride (0.13 g, 0.72 mmol), and triethylamine (0.31 mL, 2.16 mmol) in pyridine (1.0 mL) was heated to 60° C. for 5 min. A freshly prepared bright yellow solution of aldrithiol (0.28 g, 1.26 mmol) and triphenylphosphine (0.34 g, 1.26 mmol) in pyridine (0.5 mL) was added to the above reaction mixture. The reaction was stirred at 60° C. overnight, cooled to room temperature, and concentrated. The product was partitioned between EtOAc and saturated NaHCO$_3$. The organic phase was washed with brine, dried with Na$_2$SO$_4$, filtered, and evaporated under reduced pressure. The crude product was purified by chromatography on silica gel (5% MeOH/CH$_2$Cl$_2$) to give the bisphosphoamidate (30 mg, 28%) as a pale yellow foam: $^1$H NMR (CDCl$_3$) δ 7.60 (s, 1H), 5.70 (s, 1H), 5.00 (m, 2H), 4.90 (s, 2H), 4.25 (m, 2H), 4.00 (m, 2H), 3.90 (m, 2H), 3.78 (m, 2H), 3.40 (m, 1H), 3.21 (m, 1H), 3.03 (s, broad, 1H), 2.35 (m, 4H), 2.05 (m, 4H), 1.90-1.65 (m, 4H), 1.32 (m, 6H), 0.90 (m, 2H), 0.60 (m, 2H); $^{31}$P NMR (CDCl$_3$) δ 20.70.

Example 75

Bisphosphoamidate 82: A mixture of phosphonic acid 6 (60 mg, 0.18 mmol), L-alanine cyclopentyl ester hydrochloride (0.13 g, 0.72 mmol), and triethylamine (0.31 mL, 2.16 mmol) in pyridine (1.0 mL) was heated to 60° C. for 5 min. A freshly prepared bright yellow solution of aldrithiol (0.28 g, 1.26 mmol) and triphenylphosphine (0.34 g, 1.26 mmol) in pyridine (0.5 mL) was added to the above reaction mixture. The reaction was stirred at 60° C. overnight, cooled to room temperature, and concentrated. The product was partitioned between EtOAc and saturated NaHCO$_3$. The organic phase was washed with brine, dried with Na$_2$SO$_4$, filtered, and evaporated under reduced pressure. The crude product was purified by chromatography on silica gel (5% MeOH/CH$_2$Cl$_2$) to give the bisphosphoamidate (30 mg, 27%) as a pale yellow foam: $^1$H NMR (CDCl$_3$) δ 7.62 (s, 1H), 5.72 (s, 1H), 5.20 (m, 2H), 4.80 (s, 2H), 4.25 (m, 2H), 4.04-3.88 (m, 4H), 3.74 (m, 2H), 3.40 (m, 1H), 3.23 (m, 1H), 3.03 (s, broad, 1H), 1.95-1.58 (m, 16H), 1.37 (m, 6H), 0.90 (m, 2H), 0.60 (m, 2H); $^{31}$P NMR (CDCl$_3$) δ 20.64.

Example 76

Bisphosphoamidate 83: A mixture of phosphonic acid 6 (40 mg, 0.12 mmol), L-phenylalanine cyclobutyl ester hydrochloride (0.13 g, 0.48 mmol), and triethylamine (0.20 mL, 1.44 mmol) in pyridine (0.5 mL) was heated to 60° C. for 5 min. A freshly prepared bright yellow solution of aldrithiol (0.19 g, 0.85 mmol) and triphenylphosphine (0.22 g, 0.85 mmol) in pyridine (0.5 mL) was added to the above reaction mixture. The reaction was stirred at 60° C. overnight, cooled to room temperature, and concentrated. The product was partitioned between EtOAc and saturated NaHCO₃. The organic phase was washed with brine, dried with Na₂SO₄, filtered, and evaporated under reduced pressure. The crude product was purified by chromatography on silica gel (5% MeOH/CH₂Cl₂) to give the bisphosphoamidate (20 mg, 22%) as a pale yellow foam: $^1$H NMR (CDCl₃) δ 7.50 (s, 1H), 7.28-7.05 (m, 10H), 5.72 (s, 1H), 5.00 (m, 2H), 4.90 (s, 2H), 4.23-4.03 (m, 4H), 3.68 (m, 2H), 3.42-3.19 (m, 2H), 3.15-2.82 (m, 7H), 2.38 (m, 4H), 2.00 (m, 4H), 1.85-1.55 (m, 4H), 0.90 (m, 2H), 0.60 (m, 2H); $^{31}$P NMR (CDCl₃) δ 20.31.

Examples 77 and 78 relate to Scheme 23.

Example 77

Diisopropyl Phosphonate 84: A mixture of 4 (5.0 g, 12.82 mmol) and trifluoroethylamine (6.35 g, 64.10 mmol) in CH₃CN (40 mL) was placed in a reaction bomb and heated to 80° C. for 4 h. The reaction mixture was cooled to room temperature and concentrated under reduced pressure. The product was partitioned between 15% MeOH/CH₂Cl₂ (3×) and brine, dried with Na₂SO₄, filtered, and concentrated. The crude product was purified by chromatography on ISCO (2-propanol/CH₂Cl₂) followed by Gilson HPLC purification (CH₃CN/H₂O) to give 84 (3.26 g, 56%) as a pale yellow foam.

Example 78

Bisphosphoamidate 85: A mixture of phosphonic acid 42 (0.11 g, 0.29 mmol), L-alanine cyclobutyl ester hydrochloride (0.31 g, 1.75 mmol), and triethylamine (0.52 mL, 3.67 mmol) in pyridine (2.0 mL) was heated to 60° C. for 5 min. A freshly prepared bright yellow solution of aldrithiol (0.47 g, 2.12 mmol) and triphenylphosphine (0.56 g, 2.12 mmol) in pyridine (1.0 mL) was added to the above reaction mixture. The reaction was stirred at 60° C. overnight, cooled to room temperature, and concentrated. The product was partitioned between EtOAc and saturated NaHCO₃. The organic phase was washed with brine, dried with Na₂SO₄, filtered, and evaporated under reduced pressure. The crude product was purified by chromatography on ISCO (2-propanol/CH₂Cl₂) to give the bisphosphoamidate (97 mg, 54%) as a pale yellow foam: $^1$H NMR (CDCl₃) δ 7.65 (s, 1H), 5.90 (s, broad, 1H), 5.00 (m, 2H), 4.80 (s, 2H), 4.35-4.20 (m, 4H), 4.00 (m, 2H), 3.87 (m, 2H), 3.70 (d, 2H), 3.38 (m, 1H), 3.20 (m, 1H), 2.30 (m, 4H), 2.00 (m, 4H), 1.90-1.60 (m, 4H), 1.35 (m, 6H); $^{31}$P NMR (CDCl₃) δ 20.61.

Example 79

This example teaches assays used to demonstrate antiproliferation activity.

Cell Types Used for Anti-Proliferation Assays

Human cancer cell lines used in anti-proliferation assays included six cervical carcinoma cell lines with three types of HPV (HPV-16, HPV-18, HPV-39), one HPV negative cervical carcinoma cell line, and two keratinocyte-like carcinoma from tongue. Normal human cells tested included skin keratinocytes, cervical keratinocytes, and lung fibroblasts. Skin keratinocytes and cervical keratinocytes were obtained from Cambrex (East Rutherford, N.J.) and all other cells were obtained from American Type Culture Collection (Manassas, Va.). Table 79-1 summarizes characteristics of each cell type and culture conditions. Anti-proliferation assay procedure 1. Cell Culture Cells were detached from culture flasks using trypsin, counted, and plated in 96-well culture plates (250-1000 cells per well, depending on cell type). On the next day (defined as day 0), after cells attached to the bottom of plates, 5-fold serial dilutions of compounds were added in duplicate. No compound and 10 μM colchicine (cell division inhibitor) was added to control wells, which would represent 100% proliferation and 0% proliferation, respectively.

2. Staining of Cells with Sulforhodamine B

Seven days after addition of compounds, culture plates were treated with 10% trichloroacetic acid at 4° C. for 1 hr, then washed with water. This procedure allows cell-derived proteins to bind to the bottom surface of plates. Proteins were stained with 0.4% Sulforhodamine B in 1% acetic acid for 10 minutes, followed by extensive washing with 1% acetic acid. Remaining dye bound to the bottom of plates was dissolved in 10 mM Trizma base. This generated purple color that was quantified by measuring the absorbance at 510 nm wavelength, using spectrophotometer.

3. Data Analysis

From the experimental data, sigmoidal dose-response curve was generated and 50% effective concentration ($EC_{50}$) was calculated using GraphPad Prism version 4.01 for Windows (GraphPad Software, San Diego Calif. USA).

TABLE 79-1

Cell types used in antiproliferation assays

| Name | HPV status | Origin | Culture media* |
|---|---|---|---|
| HPV positive carcinoma cell lines | | | |
| SiHa | HPV-16 (1-2 copies per cell) | Squamous cell carcinoma in cervix | A1, A2 |
| Ca Ski | HPV-16 (600 copies per cell) | Epidermoid carcinoma, metastased to small intestine from cervix | A1, A2 |
| MS751 | HPV-18 (also contains a partial HPV-45 genome) | Epidermoid carcinoma, metastased to lymph node from cervix | A1, A2 |
| HeLa | HPV-18 | Epithelial adenocarcinoma in cervix | A1, A2 |
| C-4 I | HPV-18 | Carcinoma in cervix | A1, A2 |
| ME-180 | HPV-39 | Epidermoid carcinoma, metastased to omentum from cervix | A1, A2 |
| HPV negative carcinoma cell lines | | | |
| HT-3 | None | Carcinoma, metastased to lymph node from cervix | A1, A2 |
| SCC-4 | None | Squamous cell carcinoma in tongue | A1, A2 |
| SCC-9 | None | Squamous cell carcinoma in tongue | A1, A2 |
| Cells from normal human tissues | | | |
| HEL299 | None | Fibroblasts in embryonic lung | A1, A2 |
| PHK (skin keratinocytes) | None | Keratinocytes in adult foreskin | B1, B2 |
| CK (cervical keratincytes) | None | Keratinocytes in adult cervix | B1, B2 |

*Culture media
Cells were maintained in humidified incubators at 37° C. with 5% CO₂, in the following culture media.
A1: Medium for culture maintenance: Eagle MEM with Earle's BSS (Cambrex, East Rutherford, NJ), supplemented with 10% fetal bovine serum, 2 mM glutamine, 100 units/mL penicillin, and 100 μg/mL streptomycin.
A2: Medium for antiproliferation assays: Eagle MEM with Earle's BSS, supplemented with 5% fetal bovine serum, 2 mM glutamine, 100 units/mL penicillin, and 100 μg/mL streptomycin.
B1: Medium for culture maintenance: Keratinocyte-SFM (Invitrogen, Carlsbad, CA), supplemented with 0.01 mg/mL bovine pituitary extract, 0.001 μg/mL recombinant epidermal growth factor, 100 units/mL penicillin, and 100 μg/mL streptomycin.
B2: Medium for antiproliferation assays: 4:1 mixture of B1 and A2.

Results

1. Selective Antiproliferation Activity of the Amidate Prodrugs in HPV Positive SiHa Cells Compared with Normal Fibroblasts.

The goal was to discover a compound that inhibits growth of HPV-transformed lesion without affecting normal cells in epidermis and dermis (such as keratinocytes and fibroblasts). In vitro antiproliferation assays were setup using SiHa cells and HEL cells, which model HPV-transformed lesion and normal fibroblasts, respectively. SiHa cells are derived from squamous cell carcinoma in cervix caused by HPV-16 infection and HEL fibroblasts are derived from normal human embryonic lung (Table 79-1). As shown in Table 79-2, 50% effective concentration ($EC_{50}$) of the seven amidate prodrugs in SiHa cells ranged 0.13-3.2 nM, while $EC_{50}$ in HEL cells ranged 12-727 nM, indicating that these compounds inhibited proliferation of SiHa cells more efficiently than HEL cells. HEL/SiHa selectivity index (HEL $EC_{50}$ divided by SiHa $EC_{50}$) ranged from 72-559 (Table 79-2).

All seven amidate prodrugs produce the same metabolite, cprPMEDAP. cprPMEDAP is further metabolized to PMEG [Compton et al., 1999; Haste et al., 1999]. Antiproliferation $EC_{50}$ of these compounds in SiHa cells were much higher than those of the prodrugs (Table 79-2), indicating that attachment of amidate moieties improved potency. Furthermore, HEL/SiHa selectivity indices of cprPMEDAP and PMEG were 17 and 4.1, respectively (Table 79-2), indicating that the prodrugs have better selectivity than cprPMEDAP and cprPMEDAP has better selectivity than PMEG.

PMEG is known to be phosphorylated to PMEGpp that acts as a chain-terminating inhibitor of cellular DNA polymerase [Compton et al., 1999; Haste et al., 1999]. Four known DNA polymerase inhibitors (Cidofovir, Ara C, doxifluridine, and Aphidicolin) and other anticancer drugs with different mechanisms of action, including DNA topoisomerase inhibitors (Dacarbazine, Ellipticine), DNA alkylaters (Doxorubicin, Mitoxantrone, Bleomycin, Mechlorethanmine), and tublin inhibitors (Vincristine, Vinblastine, Etoposide, and Indanocine) were tested in SiHa and HEL cells (Table 79-2). Antiproliferation $EC_{50}$ of these compounds in SiHa cells varied, and some were equally or more potent than the seven amidate prodrugs. Nonetheless, all of them exhibited poor HEL/SiHa selectivity indices (0.01-3.98), compared with the seven amidate prodrugs.

Taken together, a unique set of compounds were taught, which shows sub-low nM antiproliferation $EC_{50}$ in HPV-16 positive SiHa carcinoma cells and greater than 50 fold selectivity when compared with HEL fibroblasts.

2. Selective Antiproliferation Activity of the Amidate Prodrugs in HPV Positive SiHa Cells Compared with Normal Keratinocytes In order to test effect of the compounds in normal cells from epidermis, anti-proliferation assays were performed using primary human keratinocytes, isolated from skin (PHK) and cervix (CK). Antiproliferation $EC_{50}$ values obtained with the seven prodrugs in PHK and CK were lower than those in HEL, indicating that keratinocytes are more susceptible than fibroblasts (Table 79-2 and 79-3). Nonetheless, PHK/SiHa and CK/SiHa selectivity indices of these prodrugs and cprPMEDAP were still better than the control compounds PMEG and a DNA polymerase inhibitor AraC (Table 79-3). Thus, the prodrugs preferentially inhibited proliferation of HPV-16 positive SiHa cells, compared with normal keratinocytes from skin and cervix.

3. Antiproliferation Activities in Other HPV Positive Cells

The seven prodrugs were then tested in five additional cell lines derived from HPV-induced cervical carcinoma (listed in Table 79-1) in antiproliferation assays and data are shown in Table 4 along with SiHa data. In SiHa, C-41, and MS751 cells, all compounds except Compound C showed sub-low nM antiproliferation $EC_{50}$. In CaSki, HeLa, and ME-180, however, all compounds were significantly less potent, with $EC_{50}$ ranging 7.8-410 nM. There seems to be no correlation between resistance and HPV type (16, 18 or 39), or resistance and metastatis (CaSki, MS751, and ME180 are derived from metastased site). The control compound AraC (DNA polymerase inhibitor) uniformly inhibited all cell lines with $EC_{50}$ values ranging 94-257 nM.

4. Antiproliferation Activities in HPV Negative Carcinoma Cells

To investigate the effect of the compounds on HPV negative carcinoma cell lines, three cell lines (HT-3, SCC4, SCC9, Table 79-1) were tested in antiproliferation assays. As shown in Table 79-4, all seven prodrugs were equally or more potent than the control compound AraC.

TABLE 79-2

Selective inhibition of HPV16+ SiHa cells compared with HEL fibroblasts

| Compound ID. | Note | Selectivity (HEL/SiHa) | Antiproliferation $EC_{50}$ (nM) SiHa cervical carcinoma (HPV16) | HEL lung fibroblast |
|---|---|---|---|---|
| A | | 72 | 0.6 | 43 |
| B | | 559 | 1.3 | 727 |
| C | | 115 | 0.20 | 23 |
| D | | 135 | 3.2 | 431 |
| E | | 164 | 0.50 | 82 |
| F | | 210 | 2.5 | 526 |
| G | | 92 | 0.13 | 12 |
| Controls | | | | |
| cprPMEDAP | Metabolite | 17 | 284 | 4821 |
| PMEG | Metabolite | 4.1 | 207 | 861 |
| AraC | DNA pol inh | 0.113 | 257 | 29 |
| Cidofovir | DNA pol inh | 0.3 | 84013 | 27952 |
| Doxifluridine | DNA pol inh | 0.449 | 8755 | 3927 |
| Aphidicolin (+) | DNA pol inh | 0.40 | 856 | 324 |
| Dacarba-zine | DNA topo inh | 3.98 | 7402 | 29481 |
| Ellipticine | DNA topo inh | 1.02 | 478 | 486 |
| Doxorubicin | DNA alkylater | 0.43 | 9.76 | 4.20 |
| Mitoxantrone | DNA alkylater | <0.37 | 8.67 | <3.2 |
| Mechlorethamine hydrochloride | DNA alkylater | 1.02 | 21863 | 22203 |
| Bleomycin | DNA alkylater | 0.01 | 3138 | 20.28 |
| Vincristine | Tublin inh | 1.55 | 1.24 | 1.92 |
| Vinblastine | Tublin inh | 0.39 | 0.68 | 0.27 |
| Etoposide | Tublin inh | 0.31 | 469 | 144 |
| Indanosine | Tublin inh | 0.27 | 588 | 159 |

TABLE 79-3

Selective inhibition of HPV16+ SiHa cells compared with primary keratinocytes

|  | Note | Selectivity (PHK/SiHa) | Selectivity (CK/SiHa) | Antiproliferation EC50 (nM) | | |
|---|---|---|---|---|---|---|
|  |  |  |  | SiHa cervical carcinoma (HPV16) | PHK skin Keratinocytes | CK cervical keratinocytes |
| Comp ID. |  |  |  |  |  |  |
| A |  | 58 | 11 | 0.6 | 35 | 7 |
| B |  | 75 | 42 | 1.3 | 98 | 54 |
| C |  | 4 | 7 | 0.20 | 0.8 | 1.4 |
| D |  | 12 | 7 | 3.2 | 39 | 22 |
| E |  | 10 | 11 | 0.50 | 5.2 | 5.4 |
| F |  | 31 | 3 | 2.5 | 78 | 7.1 |
| G |  | 22 | 15 | 0.13 | 2.9 | 1.9 |
| Controls |  |  |  |  |  |  |
| cprPMEDAP | metabolite | 13 | 2.4 | 284 | 3698 | 694 |
| PMEG | metabolite | 0.48 | 2.4 | 207 | 101 | 501 |
| AraC | DNA pol inh | 0.57 | 0.4 | 257 | 147 | 107 |

TABLE 79-4

Antiproliferation activities in other HPV positive and negative carcinoma cells

|  | Antiproliferation EC50 (nM) in HPV positive carcinoma cells | | | | | | Antiproliferation EC50 (nM) in HPV negative carcinoma cells | | |
|---|---|---|---|---|---|---|---|---|---|
|  | SiHa HPV16 | CaSki HPV16 | HeLa HPV18 | MS-751 HPV18 | C-4I HPV18 | ME-180 HPV39 | HT-3 cervix | SCC-4 tongue | SCC-9 tongue |
| Comp ID. |  |  |  |  |  |  |  |  |  |
| A | 0.6 | 29 | 16 | 1.7 | 6.5 | 27 | 14 | 17 | 40 |
| B | 1.3 | 246 | 410 | 18 | 27 | 254 | 104 | 53 | 150 |
| C | 0.20 | 3.87 | 6.6 | 0.54 | 1.0 | 7.8 | 9.5 | 2.1 | 2.5 |
| D | 3.2 | 301 | 398 | 16 | 24 | 288 | 127 | 44 | 147 |
| E | 0.50 | 38 | 19 | 2.40 | 3.1 | 27 | 17 | 8 | 13 |
| F | 2.5 | 124 | 127 | 4.2 | 6.0 | 41 | 24 | 10 | 28 |
| G | 0.13 | 28 | 12 | 0.9 | 3.1 | 8.2 | 6.0 | 2.1 | 7.9 |
| Controls |  |  |  |  |  |  |  |  |  |
| AraC | 257 | 94 | 174 | 144 | 123 | 101 | 214 | 74 | 68 |

Example 80

Antiproliferation Assay

Antiproliferation assays measure effect of compounds on proliferation of cultured cells. Active compounds in antiproliferation assays may be cytostatic (inhibit cell division) and/or cytocidal (kill cells). By performing antiproliferation assays using HPV positive carcinoma cells and normal cells, we identify compounds that selectively inhibit proliferation of HPV positive carcinoma cells compared with cells from normal human tissues. Table 80-1 summarizes characteristics of each cell type, including six cervical carcinoma cell lines transformed by HPV, normal human skin keratinocytes (PHK), and normal lung fibroblasts (HEL). Skin keratinocytes were obtained from Cambrex (East Rutherford, N.J.). All other cells were obtained from American Type Culture Collection (Manassas, Va.).

Cells were detached from culture flasks using trypsin, counted, and plated in 96-well culture plates (250-100 cells per well, depending on cell type). On the next day (defined as day 0), 5-fold serial dilutions of compounds were added in duplicate. Seven days after addition of compounds, culture plates were treated with 10% trichloroacetic acid at 4° C. for 1 hr and washed with water. This procedure allows cellular proteins to bind to the bottom surface of plates. Proteins were stained with 0.4% Sulforhodamine B in 1% acetic acid for 10 minutes, followed by extensive washing with 1% acetic acid. Remaining dye bound to the bottom of plates was solubilized in 10 mM Trizma base, generating purple color. Intensity of the color (proportional to cell number) was quantified by measuring the absorbance at 510 nm wavelength, using spectrophotometer. Cells without drug treatment (=100% proliferation) and cells treated with 10 μM colchicine (cell division inhibitor) (=0% proliferation) were used as controls, to determine % inhibition. % inhibition values were plotted against compound concentrations, fitted to a sigmoidal dose response curve, from which the compound concentration that reduced cell proliferation rate by 50% (=$EC_{50}$) was determined. GraphPad Prism version 4.00 for Windows (GraphPad Software, San Diego Calif. USA) was used for the curve fitting and $EC_{50}$ calculation.

Apoptosis Assay (Caspase 3 Induction Method)

Induction of caspases is one of the early events associated with apoptosis or programmed cell death. Caspase activity can be quantitatively detected using fluorescent substrate.

Compounds that directly act on the apoptotic pathway may induce caspase in a relatively short incubation period (<24 hrs). Compounds that disturb other cell physiology, which eventually causes apoptosis, may require longer incubation period (>48 hrs) for induction of caspase.

10,000 cells were plated in 96-well culture plates and incubated with 5-fold serial dilutions of compounds for 24, 48, and 72 hrs. Cells were lysed and activity of caspase in cell lysates were measured using fluorescent substrate, according to the manufacturer's instruction (Caspases assay kit, Roche, Indianapolis, Ind.).

Apoptosis Assay (Annexin V Staining Method)

Translocation of phosphatidylserine from the inner of the cell membrane to the outside is one of the the early/intermediate events associated with apoptosis or programmed cell death. Translocated phosphatidylserine can be detected by incubating cells with FITC-labelled Annexin V, which is a Ca++ dependent phospholipid-binding protein. When cells are stained with Annexin-FITC and propidium iodide (which stains dead cells), live cells are negative for both dyes, dead cells are positive for both, while apoptotic cells are positive only for Annexin-FITC.

HPV-16 SiHa cells were cultured with three different concentrations of compounds for 3 or 7 days and simultaneously stained with Annexin-FITC and propidium iodide. Staining of each individual cell was examined by flow cytometry.

Results

Selective Antiproliferation Activity

The purpose of this procedure was to identify compounds that inhibits growth of HPV-transformed lesion without affecting normal cells in epidermis and dermis (such as keratinocytes and fibroblasts). Therefore, compounds were tested in SiHa, PHK, and HEL cells, which model HPV-transformed cells, normal keratinocytes, and normal fibroblasts, respectively.

Representative compounds of the present invention, such as those listed in Table 80-2, showed detectable levels of antiproliferation activity in SiHa cells, with 50% effective concentration ($EC_{50}$) less than 25,000 nM. Active compounds were also tested in HEL cells. In all cases, $EC_{50}$ in HEL cells were higher than $EC_{50}$ in SiHa cells, indicating that the active compounds inhibited proliferation of SiHa cells more efficiently than HEL cells. Other nucleotide/nucleoside analogs, such as PMEG (2-phosphonomethoxyethyl guanine), Ara-C (cytarabine, CAS# 147-94-4), and gemcitabine (CAS# 95058-81-4) did not show such selectivity. Podofilox (CAS# 518-28-5), the active ingredient of the anti-wart drug Condylox, also showed no selectivity.

Representative prodrug compounds of the present invention, such as those listed in Table 80-3 show activities. In most cases, the prodrugs were more potent and in some cases, more selective than their respective parent compounds. The majority of phosphoamidate prodrugs were more active and selective than podofilox.

Taken together, compounds were identified that possess sub nM antiproliferation $EC_{50}$ in HPV-16 positive SiHa cells and greater than 50 fold selectivity when compared with PHK keratinocytes or with HEL fibroblasts.

Antiproliferation Activity in Other HPV+ Cell Lines

Selected compounds were also tested in five additional cell lines derived from HPV-induced cervical carcinoma (see Example 79 and Table 80-4). Each compound showed different levels of activities in the six HPV+ cell lines, regardless the type of HPV present. In general, compounds were more potent in SiHa (HPV-16), C-41 (HPV-18), and MS751 (HPV-18) cells than in CaSki (HPV-16), HeLa (HPV-18), and ME-180 (HPV-39) cells.

Induction of Apoptosis (Caspase 3 Induction Method)

A representative compound of the present invention was tested for induction of apoptosis in SiHa cells. When cells were incubated for 72 hrs (solid bars), significant dose responsive induction of caspase was observed, indicating that the compound induced apoptosis (FIG. 80-1). Induction of caspase was less obvious with 48 hr incubation (shaded bars) and was not observed with 24 hr incubation (data not shown).

Induction of Apoptosis (Annexin V Staining Method)

PMEG, N6-cyclopropyl PMEDAP, and a representative compound of the present invention were tested at three different concentrations, for induction of apoptosis in SiHa cells, using Annexin V-Propidium iodide double staining method. With all three compounds, a greater percentage of apoptotic cells were observed on day 7 than day 3. The aforementioned representative compound of the present invention was the most active in inducing apoptosis; on day 7, 63.8% of cells in the culture treated with 0.2 µg/m of this compound were apoptotic. In contrast, cultures treated with 0.2 µg/mL PMEG and 0.5 µg/mL N6-cyclopropyl PMEDAP only had 1.2% and 15.9% of apoptotic cells, respectively.

TABLE 80-1

Cell types used in antiproliferation assays

| Name | HPV status* | Origin | Culture media** |
|---|---|---|---|
| HPV positive carcinoma cell lines | | | |
| SiHa | HPV-16 | Squamous cell carcinoma in cervix | A1, A2 |
| Ca Ski | HPV-16 | Epidermoid carcinoma, metastased to small intestine from cervix | A1, A2 |
| MS751 | HPV-18 (also contains a partial HPV-45 genome) | Epidermoid carcinoma, metastased to lymph node from cervix | A1, A2 |
| HeLa | HPV-18 | Epithelial adenocarcinoma in cervix | A1, A2 |
| C-4 I | HPV-18 | Carcinoma in cervix | A1, A2 |
| ME-180 | HPV-39 | Epidermoid carcinoma, metastased to omentum from cervix | A1, A2 |
| Cells from normal human tissues | | | |
| HEL299 | none | Fibroblasts in embryonic lung | A1, A2 |
| PHK (skin keratinocytes) | none | Keratinocytes in adult foreskin | B1, B2 |

*The subtype of HPV DNA integrated in the cellular DNA.
**Culture media
Cells were maintained in humidified incubators at 37° C. with 5% $CO_2$, in the following culture media.
A1: Medium for culture maintenance: Eagle MEM with Earle's BSS (Cambrex, East Rutherford, NJ), supplemented with 10% fetal bovine serum, 2 mM glutamine, 100 units/mL penicillin, and 100 µg/mL streptomycin.
A2: Medium for antiproliferation assays: Eagle MEM with Earle's BSS, supplemented with 5% fetal bovine serum, 2 mM glutamine, 100 units/mL penicillin, and 100 µg/mL streptomycin.
B1: Medium for culture maintenance: Keratinocyte-SFM (Invitrogen, Carlsbad, CA), supplemented with 0.01 mg/mL bovine pituitary extract, 0.001 µg/mL recombinant epidermal growth factor, 100 units/mL penicillin, and 100 µg/mL streptomycin.
B2: Medium for antiproliferation assays: 4:1 mixture of B1 and A2.

TABLE 80-2

Antiproliferation activity of N6-substituted PMEDAP in HPV16+ SiHa cells and HEL fibroblasts

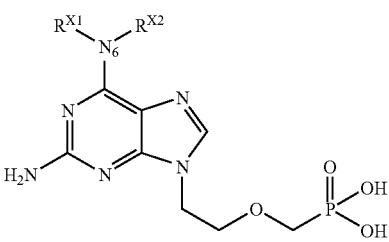

where $R^{X1}$ is hydrogen, and $R^{X2}$ is one of the following substituents, except in the indicated instances (*), where $R^{X1}$ and $R^{X2}$ together forms a N-heterocyclic ring.

methylamine
1-propylamine
1-butylamine
dimethylamine
methylethylamine
2-methylpropan-1-amine
allyl amine
2-propynyl amine
2-butylene amine
2-isobutylen amine
cyclopropylamine
cyclopropylmethanamine
1-cyclopropylethanamine
dicyclopropylamine
cyclobutylamine
cyclopentanamine
cyclohexaneamine
cycloheptanamine
cyclooctanamine
diethanolamine
2-ethanolamine
2-propanol amine
1-amine 2-propanol amine
2-methoxyethylamine
6-aminohexaneamine
3-aminopropylamine
2-dimethylaminoethylamine
6-hexanateamine
benzylamine
methylbenzylamine
4-aminobenzylamine
2-phenylethanamine
2-pyridinyl 1-methanamine
3-pyridinyl 1-methanamine
4-pyridinyl 1-methanamine
1-naphthylamine
*pyrrolidine (N6 makes pyrrolidine)
*piperidine (N6 makes piperidine)
*morpholine (N6 makes morpholine)
2,2,2-trifluoroethanamine

TABLE 80-3

Antiproliferation activity of phosphoamidate prodrugs of N6-substituted PMEDAP in HPV16+ SiHa cells, PHK keratinocytes, and in HEL fibroblasts

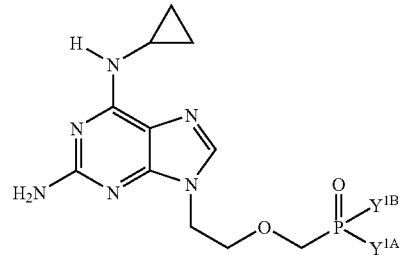

where $R^{X1}$ and $R^{X2}$ are substituted as depicted in the formula, and $Y^{1A}$ and $Y^{1B}$ are substituted as indicated,

| $Y^{1A}$ | $Y^{1B}$ |
|---|---|
| OH | OH |
| POC | POC |
| O-iPr | O-iPr |
| Ala-Et | Ala-Et |
| Ala-Pr | Ala-Pr |
| Ala-iPr | Ala-iPr |
| Ala-Bu | Ala-Bu |
| Ala-cBu | Ala-cBu |
| Ala-cPen | Ala-cPentyl |
| Ala-Hexyl | Ala-Hexyl |
| Ala-Octyl | Ala-Octyl |
| Aba-Et | Aba-Et |
| Aba-Bu | Aba-Bu |
| Aba-Octyl | Aba-Octyl |
| Phe-Et | Phe-Et |
| Phe-Bu | Phe-Bu |
| Phe-iBu | Phe-iBu |
| Phe-cBu | Phe-cBu |
| OPh | Ala-Me |
| OPh | Ala-El |
| OPh | Ala-Pr |
| OPh | Ala-iPr |
| OPh | Ala-Bu |
| OPh | Ala-tBu |
| OPh | Ala-Hexyl |
| OPh | Ala-Octyl |
| OPh | Aba-Et |
| OPh | Aba-Bu |
| OPh | Aba-cBu |
| OPh | Aba-Octyl |
| OPh | Phe-Et |
| OPh | Phe-Bu |
| OPh | Phe-iBu |
| OPh | D-Ala-Me |

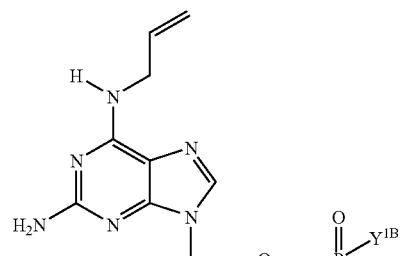

where $R^{X1}$ and $R^{X2}$ are substituted as depicted in the formula, and $Y^{1A}$ and $Y^{1B}$ are substituted as indicated,

| $Y^{1A}$ | $Y^{1B}$ |
|---|---|
| OH | OH |
| O-iPr | O-iPr |

TABLE 80-3-continued

Antiproliferation activity of phosphoamidate prodrugs of N6-
substituted PMEDAP in HPV16+ SiHa cells, PHK keratinocytes, and in
HEL fibroblasts

| POC | POC |
|---|---|
| Ala-Et | Ala-Et |
| Ala-Bu | Ala-Bu |
| Ala-cBu | Ala-cBu |
| Ala-Hexyl | Ala-Hexyl |
| Aba-Bu | Aba-Bu |
| Phe-Et | Phe-Et |
| Phe-Bu | Phe-Bu |
| Phe-iBu | Phe-iBu |
| OPh | Ala-Et |
| OPh | Ala-Bu |
| OPh | Ala-cBu |
| OPh | Ala-Hexyl |
| OPh | Aba-Bu |
| OPh | Phe-Et |
| OPh | Phe-Bu |
| OPh | Phe-iBu |

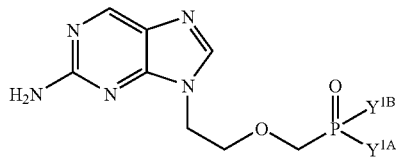

where $R^{X1}$ and $R^{X2}$ are substituted as depicted in the formula, and $Y^{1A}$ and $Y^{1B}$ are substituted as indicated,

| $Y^{1A}$ | $Y^{1B}$ |
|---|---|
| OH | OH |
| O-iPr | O-iPr |
| Ala-Bu | Ala-Bu |
| OPh | Phe-Et |

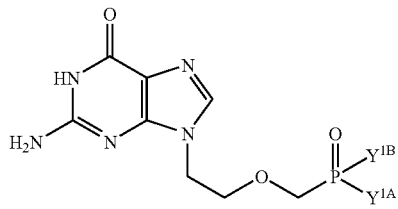

where $R^{X1}$ and $R^{X2}$ are substituted as depicted in the formula, and $Y^{1A}$ and $Y^{1B}$ are substituted as indicated,

| $Y^{1A}$ | $Y^{1B}$ |
|---|---|
| OH | OH |
| Ala-Bu | Ala-Bu |

TABLE 80-4

Antiproliferation activities of N6-cycloprolyl PMEDAP and its phosphoamidate prodrugs in six different HPV positive cells

| | Antiproliferation EC50 (nM) in HPV positive carcinoma cells | | | | | |
|---|---|---|---|---|---|---|
| Compound ID. | SiHa HPV16 | CaSki HPV16 | HeLa HPV18 | MS-751 HPV18 | C-4I HPV18 | ME-180 HPV39 |
| A | 0.6 | 29 | 16 | 1.7 | 6.5 | 27 |
| B | 1.3 | 246 | 410 | 18 | 27 | 254 |
| C | 0.2 | 3.9 | 6.6 | 0.5 | 1.0 | 7.8 |
| D | 3.2 | 301 | 398 | 16 | 24 | 288 |
| E | 0.5 | 38 | 19 | 2.4 | 3.1 | 27 |
| F | 2.5 | 124 | 127 | 4.2 | 6.0 | 41 |
| G | 0.13 | 28 | 12 | 0.9 | 3.1 | 8.2 |

TABLE 80-4-continued

Antiproliferation activities of N6-cycloprolyl PMEDAP and its phosphoamidate prodrugs in six different HPV positive cells

| | Antiproliferation EC50 (nM) in HPV positive carcinoma cells | | | | | |
|---|---|---|---|---|---|---|
| Compound ID. | SiHa HPV16 | CaSki HPV16 | HeLa HPV18 | MS-751 HPV18 | C-4I HPV18 | ME-180 HPV39 |
| H | 0.03 | 2.0 | 0.7 | 0.04 | 0.44 | 1.8 |
| (cprPMEDAP) | 284 | 14149 | 6926 | 3313 | 1332 | 8315 |

Example 81

Rabbit Skin Irritation Study of Compounds A and B

A study was conducted to evaluate the potential of two compounds of the present invention to produce irritation when administered via dermal application to male rabbits for seven consecutive days. A total of six males were assigned to the study as presented in the table below.

| Group Assignments | | |
|---|---|---|
| Group Number | Test Article[a] | Number of Animals (male) |
| 1 | Compound B[b] | 3 |
| 2 | Compound A[c] | 3 |

[a]Each animal received dermal treatments of vehicle (placebo gel), one positive control article, and three concentrations of the appropriate test article. Each animal received one test article at concentrations of 0.01, 0.03, and 0.1%.
[b]The positive control article used was 0.1% 9-(2-phosphonylmethoxyethyl) guanine (PMEG).
[c]The positive control article used was 1% Cidofovir ®.

The vehicle, positive control articles, and test articles were administered dermally once daily for seven days during the study. The test articles were administered at concentrations of 0.01, 0.03, and 0.1%. The positive control articles were administered at concentrations of 0.1% (PMEG) or 1% (Cidofovir®). The dose volume for all formulations was a fixed volume of 100 µL.

The test sites for each animal were shaved prior to the initial administration and as needed during the study. Two sites were clipped on the left dorsal side, and three were clipped on the right dorsal side. The outline of each dosing (approximately 1 square inch each) was marked with indelible ink. The total clipped area comprised no less than 10% of the total body surface of each animal. The vehicle and appropriate positive control and test article were administered to each animal within a dosing site of approximately 1 square inch. Vehicle was administered on the left rostral site (Dose Site 1), and the appropriate positive control article was administered to the left caudal site (Dose Site 2). The appropriate test article was administered as follows: 0.01% to the right rostral site (Dose Site 3), 0.03% to the right middle site (Dose Site 4), and 0.1% to the right caudal site (Dose Site 5). Collars were placed on the animals immediately following dosing for 1 to 2 hours.

The sites were evaluated for erythema and edema prior to dosing on Day 1 and daily thereafter, approximately 24 hours following each dose and prior to the next dose. Each site was assigned an irritation score based upon the Draize scale for scoring skin irritation (Draize J H, Woodard G, Calvery H O, Methods for the study of irritation and toxicity of substances applied topically to the skin and mucous membranes. J Pharmacol Exp Ther 1944;82:377-90).

Observations for mortality, morbidity, and the availability of food and water were conducted twice daily for all animals. Detailed clinical examinations were conducted prior to randomization, prior to dosing on Day 1, and daily thereafter. Body weights were measured and recorded the day after arrival, prior to randomization, and prior to dosing on Days 1, 3, and 7.

Euthanasia was by intravenous anesthesia overdose with sodium pentobarbital-based euthanasia solution and exsanguinations by severing the femoral vessels. The animals were examined carefully for external abnormalities including masses. The skin was reflected from a ventral midline incision and any abnormalities were identified and correlated with ante-mortem findings. The abdominal, thoracic, and cranial cavities were examined for abnormalities and the organs removed, examined, and, where required, placed in neutral buffered formalin. The dosing sites, kidneys, and any gross lesions of each animal were collected and preserved. Microscopic examination of fixed hematoxylin and eosin-stained paraffin sections were performed for each dosing site for all animals. The slides were examined by a veterinary pathologist. A four-step grading system was utilized to define gradable lesions for comparison between dose groups.

Conclusions

The two test articles did not produce notable clinical findings, dermal irritation, changes in body weight or macroscopic and microscopic observations at any dose concentrations. One of the positive controls was associated with clinical findings and slight to moderate macroscopic and microscopic observations.

Example 82

Rabbit Skin Irritation Study of Compounds B and H

A study was conducted to evaluate the potential of two compounds of the present invention to produce irritation when administered via dermal application to male for seven consecutive days. A total of 24 males were assigned to the study.

Study Design for Compound B

| Dose Site | Group 1 (n = 6)[a] | Group 1 Concentration[b] % | (mg/mL) | Group 2 (n = 6)[a] | Group 2 Concentration[b] % | (mg/mL) |
|---|---|---|---|---|---|---|
| 1 | Vehicle control | 0.0 | 0.0 | PMEG (positive control) | 0.1% | 1.0 |
| 2 | Low Dose | 0.03 | 0.3 | Low Dose | 0.03 | 0.3 |
| 3 | Mid Dose | 0.1 | 1.0 | Mid Dose | 0.1 | 1.0 |
| 4 | High Dose | 0.3 | 3.0 | High Dose | 0.3 | 3.0 |

[a] Each group consisted of six naïve rabbits.
[b] The vehicle for Dose Site 1, Group 1, and Dose Site 1, Group 2 (PMEG) was the vehicle gel. The vehicle for Group 1 treated sites was the vehicle gel, and the vehicle for Group 2 treated sites was the vehicle ointment.

Study Design for Compound H

| Dose Site | Group 3 (n = 6)[a] | Group 3 Concentration[b] % | (mg/mL) | Group 4 (n = 6)[a] | Group 4 Concentration[b] % | (mg/mL) |
|---|---|---|---|---|---|---|
| 1 | Vehicle control | 0.0 | 0.0 | PMEG (positive control) | 1.0% | 10.0 |
| 2 | Low Dose | 0.03 | 0.3 | Low Dose | 0.03 | 0.3 |
| 3 | Mid Dose | 0.1 | 1.0 | Mid Dose | 0.1 | 1.0 |
| 4 | High Dose | 0.3 | 3.0 | High Dose | 0.3 | 3.0 |

[a] Each group consisted of six naïve rabbits.
[b] The vehicle for Dose Site 1, Group 3 was the vehicle ointment, and the vehicle for Dose Site 1, Group 4 (cPrPMEDAP) was the vehicle gel. The vehicle for Group 3 treated sites was the vehicle gel, and vehicle for Group 4 treated sites was the vehicle ointment.

The test and control articles were administered dermally once per day for 7 consecutive days during the study. The dose levels for Compound B were 0.03, 0.1, and 0.3%. The dose levels for Compound H were 0.03, 0.1, and 0.3%. The dose level for PMEG (positive control) was 0.1%. The dose level for cPrPMEDAP (positive control) was 1.0%. The dose level for the vehicle control was 0.0% (this was dosed as both gel and ointment formulations). The dose volume for all sites was a constant 100 μL. Less than 24 hours prior to the first administration, the hair was clipped from the back of the animal. This clipped area comprised no less than 10% of the total body surface area. Care was taken to avoid abrading the skin.

The test, positive control, and vehicle control articles were administered within a dosing site of approximately 1"×1". Two dosing sites were placed along the left dorsal surface. The vehicle or positive control article was administered to the rostral site, and the low dose of the test article was administered to the caudal site. Two dosing sites were placed along the right dorsal surface. The mid-dose of the test article was administered to the rostral site, and the high dose of the test article was administered to the caudal site. Collars were placed on the animals for approximately two hours immediately following dosing. The duration of collaring was documented in the raw data.

Observations for mortality, morbidity, and the availability of food and water were conducted twice daily for all animals. The test sites were evaluated for erythema and edema prior to the first administration and at approximately 24 hours following each administration (prior to the next scheduled dosing) and daily during the 7-day recovery period. Observations for clinical signs were conducted daily during the study at the same time as the dermal observations. Body weights were measured and recorded the day after receipt, prior to randomization, prior to test article administration on Day 1, and on Days 7 and 14, and at necropsy (Days 8 and 15). Body weights taken at receipt and prior to random are not reported, but maintained in the study file. Blood samples (4-6 mL) will be collected from 6 animals/group at termination and 3 animals/group at recovery from the jugular or other suitable vein for evaluation of clinical pathology parameters.

Additional blood samples (approximately 1 mL) were taken from all animals from the jugular or other suitable vein for determination of the plasma concentrations of the test article at approximately 2 hours postdose on Day 7. Samples were placed in tubes containing potassium EDTA and stored on an ice block until centrifuged. Animals were not fasted before blood collection. Samples were stored at −70° until examination.

Complete necropsy examinations were performed under procedures approved by a veterinary pathologist on all animals. Euthanasia was by anesthesia overdose with sodium pentobarbital-based euthanasia solution via the ear vein/artery or other suitable vein and exsanguinations by severing the femoral vessels. The animals were examined carefully for external abnormalities including masses. The skin was reflected from a ventral midline incision and any abnormalities were identified and correlated with ante-mortem findings. The abdominal, thoracic, and cranial cavities were examined for abnormalities and the organs removed, examined, and, where required, placed in neutral buffered formalin. Microscopic examination of fixed hematoxylin and eosin-stained paraffin sections was performed on sections of tissues from the dosing sites (4 per animal), kidneys, and any gross lesions.

At the time of necropsy, Day 8 for main study animals and Day 15 for recovery animals, the four dosing sites per animal were identified. Approximately half of each dosing site was excised and then collected and preserved as mentioned above for histologic processing. While the other approximate half, of each dosing site was still intact on the animal, the following procedures are performed. The dosing sites were wiped with three gauzes of ethanol (95%) and allowed to dry completely. Tape (3M® packing tape or equivalent) was applied to each dosing site ten times. A clean piece of tape was used for reach application. The remaining portions of the dosing sites were then excised with scissors. The scissors were washed between each dose site and animal with acetone or ethanol. The order of dose site removal was vehicle or positive control site, low dose site, mid-dose site, and high dose site. A 1 cm$^2$ tissue was excised from each dose site. The tissue sample was weighted and recorded. The skin punches were minced with clean scissors in individual appropriately sized scintillation vials. Cold phosphate-buffered saline (5 mL) was added to the scintillation vial. The tissue was then homogenized with 20 second pulses using a mechanical homogenizer. The homogenates were quickly frozen at approximately −20° C.

Conclusions

Based on dermal irritation scores and microscopic findings, one of the test articles was non-irritating in the vehicle gel, but was a mild to moderate irritant in the vehicle ointment. The second test article was a very slight irritant in the vehicle gel and a mild irritant when formulated in the vehicle ointment.

Example 83

Preparation of Topical Gel Pharmaceutical Composition

This example illustrates the preparation of a representative topical gel composition containing an active compound of Formula I.

A topical gel composition is prepared having the following composition:

| Components | % w/w |
| --- | --- |
| Active compound | X* |
| pH 4.5 or 7 Buffer | 25 |
| Propylene Glycol, USP | 25 |
| Hydroxyethylcellulose, NF | 1.25 |
| Propylparaben, NF | 0.01 |
| Methylparaben, NF | 0.09 |
| Edetate Disodium, USP | 0.025 |
| Glycerin, USP | 10.00 |
| Citric Acid, USP | 0.50 |
| Sterile Water for Injection, USP | 38.125 |

*X = Compound ranging from 0.01% to 1.0%

Other compounds of Formula I, such as those prepared in accordance with the present Specification can be used as the active compound in the preparation of the gel formulations of this example.

The following ingredients have also been evaluated for suitability during the development of this formulation:
Isopropyl mysritate (solvent/cosolvent/penetration enhancer),
Polyethylene glycols, Triacetin (solvents),
Cetyl alcohol and Stearyl alcohol (Stiffening agents),
Carbomer (Viscosity enhancer), and
Tweens, Spans (emulsifiers).

Example 84

Preparation of Topical Ointment Pharmaceutical Composition

This example illustrates the preparation of a representative topical ointment composition containing an active compound of Formula I.

A topical ointment composition is prepared having the following composition:

| Components | % w/w |
| --- | --- |
| Active Compound | X* |
| Petrolatum, USP | 94.0 |
| Sorbitan Sesquioleate, NF | 0.5 |
| Propylene Glycol, USP | 4.5 |

*X = Compound ranging from 0.01% to 1.0%

Other compounds of Formula I, such as those prepared in accordance with the present Specification can be used as the active compound in the preparation of the ointment formulations of this example.

The following ingredients have also been evaluated for suitability during the development of this formulation:
Isopropyl mysritate (solvent/cosolvent/penetration enhancer),
Polyethylene glycols, Triacetin (solvents),
Cetyl alcohol and Stearyl alcohol (Stiffening agents),
Carbomer (Viscosity enhancer), and
Tweens, Spans (emulsifiers).

What is claimed is:

1. A compound of formula II

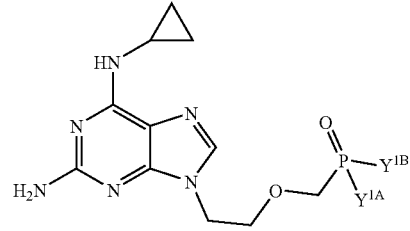

Formula II wherein $Y^{1A}$ and $Y^{1B}$ are independently

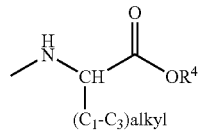

wherein $R^4$ is —$(C_1-C_8)$ alkyl, —$(C_2-C_8)$ alkenyl, or —$(C_2-C_8)$ alkynyl.

2. The compound of claim 1, wherein $R^4$ is —$(C_1-C_4)$ alkyl.

3. The compound of claim 1, wherein $Y^{1A}$ and $Y^{1B}$ are

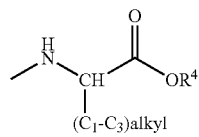

wherein $R^4$ is —$(C_1-C_8)$ alkyl.

4. The compound of claim 1, wherein $Y^{1A}$ and $Y^{1B}$ are independently

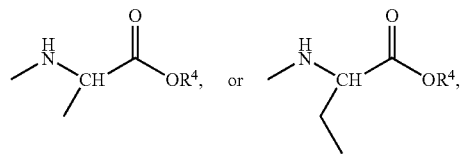

wherein $R^4$ is —$(C_1-C_8)$ alkyl, —$(C_2-C_8)$ alkenyl, or —$(C_2-C_8)$ alkynyl.

5. The compound of claim 4, wherein $R^4$ is —$(C_1-C_4)$ alkyl.

6. The compound according to claim 1 being selected from the group consisting of the following compounds:

(a)

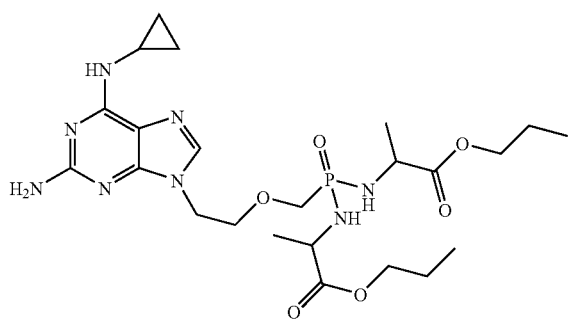

(b)

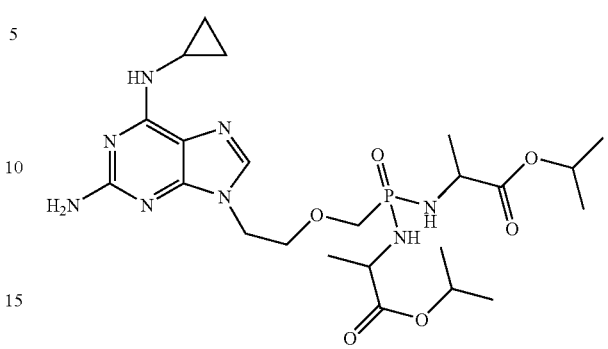

(c)

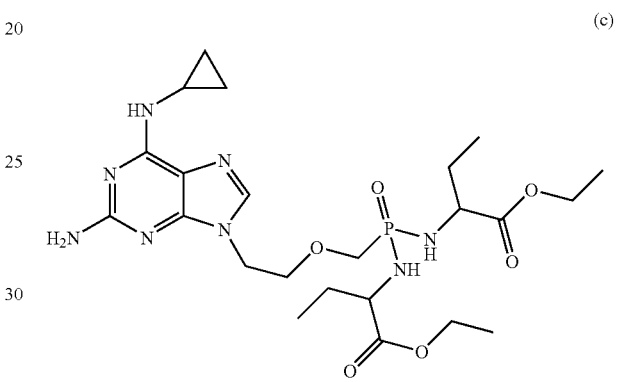

(d)

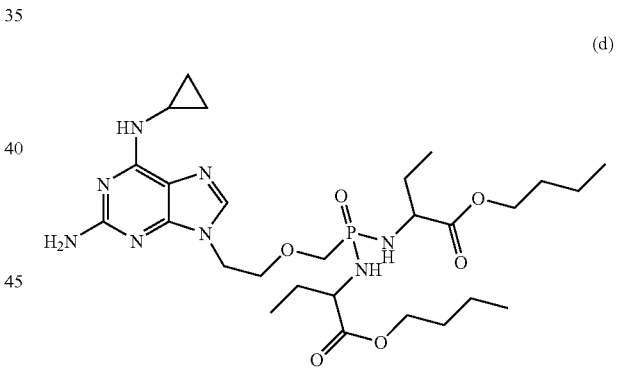

(e)

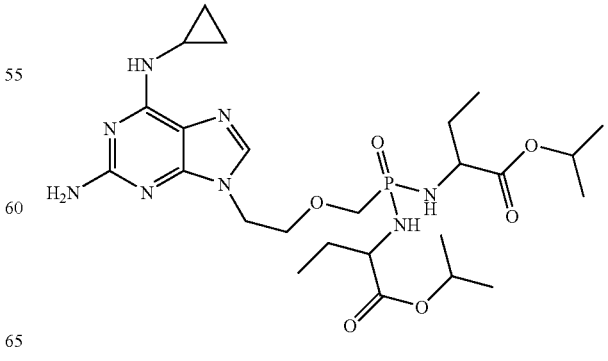

-continued

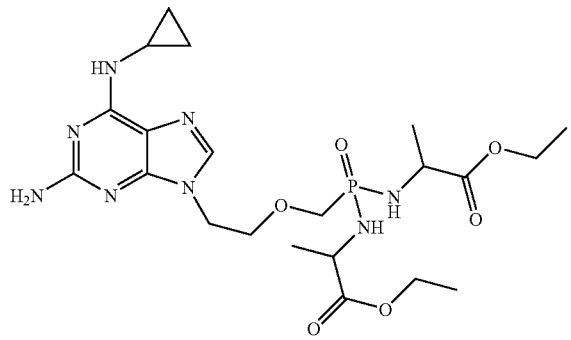

(f)

7. A pharmaceutical composition comprising an effective amount of a compound according to claim 1, or a pharmaceutically acceptable salt thereof, and one or more pharmaceutically acceptable carriers.

8. The pharmaceutical composition of claim 7, further comprising one or two or more therapeutically active agents selected from antiviral agents, antibiotics, antipyretics, or analgesics.

9. The pharmaceutical composition of claim 7, further comprising one or two or more therapeutically active agents selected from amantidine, rimantadine and ribavirin.

* * * * *

UNITED STATES PATENT AND TRADEMARK OFFICE
CERTIFICATE OF CORRECTION

Page 1 of 1

PATENT NO.         : 7,553,825 B2
APPLICATION NO.    : 11/026303
DATED              : June 30, 2009
INVENTOR(S)        : Cheng et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 486 days.

Signed and Sealed this
Seventeenth Day of May, 2011

David J. Kappos
*Director of the United States Patent and Trademark Office*